(12) United States Patent
Davido et al.

(10) Patent No.: US 7,785,605 B2
(45) Date of Patent: Aug. 31, 2010

(54) HERPES SIMPLEX VIRUS MUTANT ICP0 PROTEIN

(75) Inventors: David Davido, Lawrence, KS (US); Priscilla Schaffer, Tucson, AZ (US)

(73) Assignees: University of Kansas, Lawrence, KS (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 12/167,870

(22) Filed: Jul. 3, 2008

(65) Prior Publication Data

US 2009/0068215 A1    Mar. 12, 2009

Related U.S. Application Data

(60) Provisional application No. 60/948,048, filed on Jul. 5, 2007.

(51) Int. Cl.
*A61K 39/245* (2006.01)
(52) U.S. Cl. .................................................. 424/231.1
(58) Field of Classification Search ........................ None
See application file for complete search history.

(56) References Cited

U.S. PATENT DOCUMENTS 6,319,703 B1 * 11/2001 Speck ..................... 435/235.1

OTHER PUBLICATIONS

David J. Davido et al. "Phosphorylation site mutations affect Herpes Simplex Virus Type 1 ICP0 function," Journal of Virology, 2005, vol. 79(2), pp. 1232-1243.
Weizhong Cai et al. "Herpes Simplex Virus Type 1 ICP0 plays a critical role in the De Novo synthesis of infectious virus following transfection of viral DNA," Journal of Virology, 1989, vol. 63(11), pp. 4579-4589.
Haidong Gu et al. "Components of the REST/CoREST/histone deacetylase repressor complex are disrupted, modified, and translocated in HSV-1-infected cells," PNAS, 2005, vol. 102(21), pp. 7571-7576.
Yu Liang et al., "State and role of Src family kinase in replication of Herpes Simplex Virus 1," Journal of Virology, 2006, vol. 80(7), pp. 3349-3359.

* cited by examiner

*Primary Examiner*—Ali R. Salimi
(74) *Attorney, Agent, or Firm*—Workman Nydegger

(57) ABSTRACT

A mutant virus of herpes simplex virus type 1 (HSV-1) can include a mutant protein involved in replication so as to impair or inhibit replication of HSV-1. The mutant HSV-1 can have a mutation in at least one phosphorylation site of a protein involved in replication in order to inhibit phosphorylation of the site so as to prohibit or impair replication of HSV-1 and/or the clinical severity of HSV-1-mediated diseases. The mutant protein can be a mutant ICP0 that has reduced or inhibited posttranslational phosphorylation. The mutant HSV-1 and/or mutant ICP0 can be used in vaccines or other pharmaceutical preparations to treat, limit and/or prevent HSV-1 infection. The mutant HSV-1 and/or mutant ICP0 can also be used in screening and/or developing anti-HSV-1 agents.

25 Claims, 16 Drawing Sheets

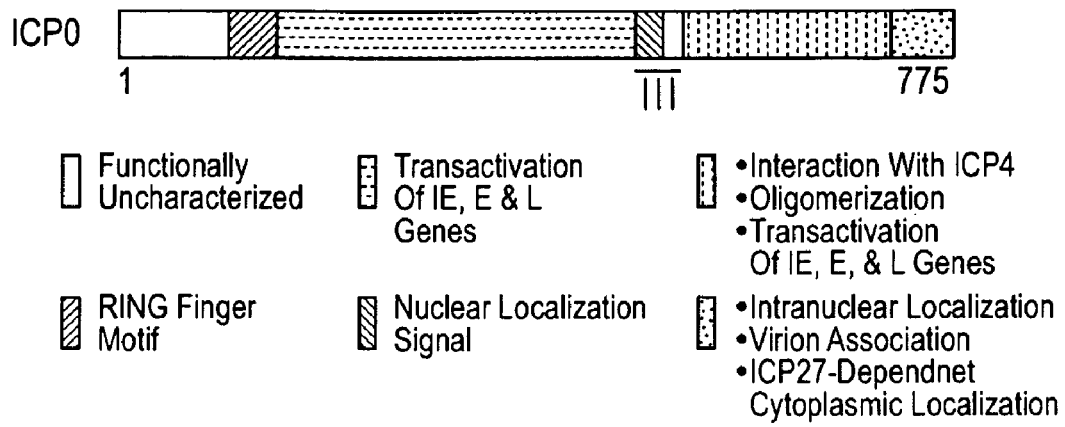
*Fig. 1A*
| Region | | Peptide Sequence | |
|---|---|---|---|
| III | 505 | RRG<u>S</u>GQEN<u>PS</u>PQ<u>ST</u>RPPLAPAGAK | 528 |
| | 508 | S CaM II, CKII, p70s6K, PKA, PKG | |
| | 514 | S CDK-1 or -2 | |
| | 517 | S PKC | |
| | 518 | T CKI | |
*Fig. 1B*
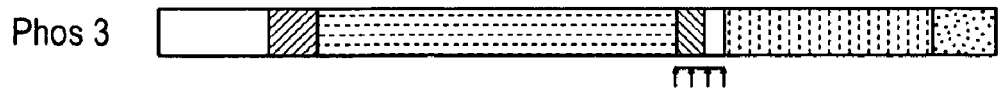
*Fig. 1C*

HSV-1s vs HSV-2s ICP0.apr

```
                                                                                    Section 1
                     (1)  1          10         20         30         40         51
HSV-1 (Syn17+) ICP0  (1)  MEPRPGASTRRPEGRPQREP---------APDVWVFPCDRDLPDSSDSEAE
HSV-2 (HG52) ICP0    (1)  MEPRPGTSSRADPG-PERPPRQTPGTQPAAPHAWGMLNDMWQLASSDSEEE
Concensus            (1)  MEPRPG SSR    G PR P           AP  W  D    SSDSE E
                                                                                    Section 2
                     (52) 52         60         70         80         90        102
HSV-1 (Syn17+) ICP0  (43) TEVGGRGDADHHDDDSASEADSTDTELFETGLLGPQGVDGGAVSG--GSPP
HSV-2 (HG52) ICP0    (51) TEVG--ISDDDLHRDSTSEAGSTDTEMFEAGLMDAATPPARPPAERQGSPT
Concensus            (52) TEVG       D   DS SEA STDTELFE GLL       A   A  GSP
                                                                                    Section 3
                    (103) 103        110        120        130        140        153
HSV-1 (Syn17+) ICP0  (92) REEDPGSCGGAPP--REDGGSDEGDVCAVCTDEIAPHLRCDTFPCMHRFCI
HSV-2 (HG52) ICP0   (100) PADAQGSCGGGPVGEEEAEAGGGGDVCAVCTDETAPPLRCQSFPCLHPFCI
Concensus           (103)    D  GSCGGAP      E A     GDVCAVCTDEIAP LRC  SFPCLH FCI
                                                                                    Section 4
                    (154) 154        160        170        180        190        204
HSV-1 (Syn17+) ICP0 (141) PCMKTWMQLRNTCPLCNAKLVYLIVGVTPSGSFSTIPIVNDPQTRMEAEEA
HSV-2 (HG52) ICP0   (151) PCMKTWIPLRNTCPLCNTPVAYLIVGVTASGSFSTIPIVNDPRTRVEAEAA
Concensus           (154) PCMKTWI LRNTCPLCN  L YLIVGVT SGSFSTIPIVNDP TRMEAE A
                                                                                    Section 5
                    (205) 205        210        220        230        240        255
HSV-1 (Syn17+) ICP0 (192) VRAGTAVDFIWTGNQRFAPRYLTLGGHTVRALSPTHPEPTTDEDDDDLDDA
HSV-2 (HG52) ICP0   (202) VRAGTAVDFIWTGNPRTAPRSLSLGGHTVRALSPTPPWPGTDDEDDDLADV
Concensus           (205) VRAGTAVDFIWTGN R APR LSLGGHTVRALSPT P P TDDDDDDL D
                                                                                    Section 6
                    (256) 256        270        280        290        306
HSV-1 (Syn17+) ICP0 (243) DYVPPAPRRTPRAPPRRGAAAPPVTGGASHAAPQPAAARTAPPSAPIGPHG
HSV-2 (HG52) ICP0   (253) DYVPPAPRRAPRR-----GGGG---AGATRGTSQPAATRPAPPGAPRSSSS
Concensus           (256) DYVPPAPRR PR      AAA      AGAS A  QPAA R APP AP
                                                                                    Section 7
                    (307) 307        320        330        340        357
HSV-1 (Syn17+) ICP0 (294) SSNHTTTTNSSGGGGSRQSRAAAPRGASGP--SGGVGVGVGVVEAEAGRPR
HSV-2 (HG52) ICP0   (296) GGAPLRAGVGSGSGGGPAVAAVVPRVASLPPAAGGGRAQARRVGEDAAAAE
Concensus           (307)        SG GG      A   PR AS P   AGG       V  DAA
                                                                                    Section 8
                    (358) 358        370        380        390        408
HSV-1 (Syn17+) ICP0 (343) GRTGPLVNRPAPLANNRDPIVISDSPPASPHRPPAAPMPGSAPR-------
HSV-2 (HG52) ICP0   (347) GRTPPAR---QPRAAQEPPIVISDSPPPSPRRP-AGPGPLSFVSSSSAQVS
Concensus           (358) GRT P       P  AN  PIVISDSPP SP RP  AAP  P S
```

*Fig. 13A*

HSV-1s vs HSV-2s ICP0.apr

```
─────────────────────────────────────────────────────────────────── Section 9
                   (409) 409        420        430        440         459
HSV-1 (Syn17+) ICP0 (387) --PGPPASAAASG-PARPRAAVAPCVRAPP-----PGPGPRAPAPGAEPAA
HSV-2 (HG52) ICP0   (394) SGPGGGGLPQSSGRAARPRAAVAPRVRSPPRAAAAPVVSASADAAGPAPPA
         Concensus (409)   PG A   ASG  ARPRAAVAP VRAPP     P    AAG P A
─────────────────────────────────────────────────────────────────── Section 10
                   (460) 460        470        480        490    500     510
HSV-1 (Syn17+) ICP0 (430) RPADARRVPQSHSSLAQAANQEQSLCRARATVARGSGGPGVEGGHGPSRGA
HSV-2 (HG52) ICP0   (445) VPVDAHRAPRSRMTQAQTDTQAQSLGRAGATDARGSGGPGAEGGPGVPRGT
         Concensus (460)   P DA R P S  AQ   Q QSL RA AT ARGSGGPG EGG G  RG
─────────────────────────────────────────────────────────────────── Section 11
                   (511) 511        520        530        540    550     561
HSV-1 (Syn17+) ICP0 (481) APSGAAPLPSAASVEQEAAVRPRKRRGSGQENPSPQSTRPPLAP-------
HSV-2 (HG52) ICP0   (496) NTPGAAPHAAEG-----AAARPRKRRGSDSGPAASSSASSSAAPRSPLAPQ
         Concensus (511)     GAAP  A A     AA RPRKRRGS       A S     AP
─────────────────────────────────────────────────────────────────── Section 12
                   (562) 562        570        580        590    600     612
HSV-1 (Syn17+) ICP0 (525) -AGAKRAATHPPSDSGPGGRGQG-------GPGTPLTS-----SAASASSS
HSV-2 (HG52) ICP0   (542) GVGAKRAAPRRAPDSDSGDRGHGPLAPASAGAAPPSASPSSQAAVAAASSS
         Concensus (562)   GAKRAA    DS G RG G       GA P  S    A AAASSS
─────────────────────────────────────────────────────────────────── Section 13
                   (613) 613        620        630        640    650     683
HSV-1 (Syn17+) ICP0 (563) SASSSSAPTPAGAASSAAGAASSSASASS---------GGAVGALGGRQE
HSV-2 (HG52) ICP0   (593) SASSSSASSSSASSSSASSSSASSSSASSSSASSSSASSSAGGAGGSVASASGAGE
         Concensus (613) SASSSSA S  AAAASSAA AAASSSASASS         GGAVAA  G E
─────────────────────────────────────────────────────────────────── Section 14
                   (664) 664        670        680        690    700     714
HSV-1 (Syn17+) ICP0 (604) --ETSLGPRAASGPRGPRKCARKTRHAETS----GAVPAGGLTRYLPISGV
HSV-2 (HG52) ICP0   (644) RRETSLGPRAAAP-RGPRKCARKTRHAEGGPEPGARDPAPGLTRYLPIAGV
         Concensus (664)   ETSLGPRAAA  RGPRKCARKTRHAE     A  PA GLTRYLPIAGV
─────────────────────────────────────────────────────────────────── Section 15
                   (715) 715        720        730        740    750     765
HSV-1 (Syn17+) ICP0 (649) SSVVALSPYVNKTITGDCLPILDMETGNIGAYVVLVDQTGNMATRLRAAVP
HSV-2 (HG52) ICP0   (694) SSVVALAPYVNKTVTGDCLPVLDMETGHIGAYVVLVDQTGNVADLLRAAAP
         Concensus (715) SSVVALAPYVNKTITGDCLPILDMETG IGAYVVLVDQTGNMA  LRAA P
─────────────────────────────────────────────────────────────────── Section 16
                   (766) 766        780        790        800    810     816
HSV-1 (Syn17+) ICP0 (700) GWSRRTLLPETAGNHVMPPEYPTAPASEWNSLWMTPVGNMLFDQGTLVGAL
HSV-2 (HG52) ICP0   (745) AWSRRTLLPEHARNCVRPPDYPTPPASEWNSLWMTPVGNMLFDQGTLVGAL
         Concensus (766) AWSRRTLLPE A N V PPDYPT PASEWNSLWMTPVGNMLFDQGTLVGAL
─────────────────────────────────────────────────────────────────── Section 17
                   (817) 817        830        846
HSV-1 (Syn17+) ICP0 (751) DFRSLRSRHPWSGEQGASTRDEGKQ-----
HSV-2 (HG52) ICP0   (796) DFHGLRSPHPWSREQGAPAPAGDAPAGHGE
         Concensus (817) DF  LRSRHPWS EQGA
```

Fig. 13A
Continued

HSV-1s vs HSV-2s ICP0.apr

```
─────────────────────────────────────────────────────────────────── Section 1
                   (1)  1        10        20        30        40        52
HSV-1 (KOS) ICP0   (1)  MEPRPGASTRR---PEGRPQREP-----APDVWVFPCDRDLPDSSDSEAETE
HSV-2 (HG52) ICP0  (1)  MEPRPGTSSRADPGPERPPRQTPGTQPAAPHAWGMLNDMQWLASSDSEEETE
        Concensus  (1)  MEPRPG SSR    PE P     P    AP  W     D    SSDSE ETE
─────────────────────────────────────────────────────────────────── Section 2
                   (53) 53       60        70        80        90        104
HSV-1 (KOS) ICP0   (45) VGGRGDADHHDDDSASEADSTDTELFETGLLGPQGVDGG--AVSGGSPPREE
HSV-2 (HG52) ICP0  (53) VG--ISDDDLHRDSTSEAGSTDTEMFEAGLMDAATPPARPPAERQGSPTPAD
        Concensus  (53) VG   D    DS SEA STDTELFE GLL      A     A  GSP   D
─────────────────────────────────────────────────────────────────── Section 3
                  (105) 105      110       120       130       140       156
HSV-1 (KOS) ICP0   (95) DPGSCGGAPPRED--GGSDEGDVCAVCTDEIAPHLRCDTFPCMHRFCIPCMK
HSV-2 (HG52) ICP0 (103) AQGSCGGGPVGEEEAEAGGGGDVCAVCTDEIAPPLRCQSFPCLHPFCIPCMK
        Concensus (105)   GSCGGAP ED   A    GDVCAVCTDEIAP LRC SFPCLH FCIPCMK
─────────────────────────────────────────────────────────────────── Section 4
                  (157) 157      170       180       190       208
HSV-1 (KOS) ICP0  (145) TWMQLRNTCPLCNAKLVYLIVGVTPSGSFSTIPIVNDPQTRMEAEEAVRAGT
HSV-2 (HG52) ICP0 (155) TWIPLRNTCPLCNTPVAYLIVGVTASGSFSTIPIVNDPRTRVEAEAAVRAGT
        Concensus (157) TWI LRNTCPLCN   YLIVGVT SGSFSTIPIVNDP TRMEAE AVRAGT
─────────────────────────────────────────────────────────────────── Section 5
                  (209) 209      220       230       240       250       260
HSV-1 (KOS) ICP0  (297) AVDFIWTGNQRFAPRYLTLGGHTVRALSPTHPEPTTDEDDDDLDDADYVPPA
HSV-2 (HG52) ICP0 (207) AVDFIWTGNPRTAPRSLSLGGHTVRALSPTPPWPGTDDEDDDLADVDYVPPA
        Concensus (209) AVDFIWTGN R APR LSLGGHTVRALSPT P P TDDDDDDL D DYVPPA
─────────────────────────────────────────────────────────────────── Section 6
                  (261) 261      270       280       290       300       312
HSV-1 (KOS) ICP0  (249) PRRTPRAPPRRGAAAPPVTGGASHAAPQPAAAARTAPPSAPIGPHGSSNTNTT
HSV-2 (HG52) ICP0 (259) PRRAP----RRGGGG----AGATRGTSQPAATRPAPPGAPRSSSSGGAPLRA
        Concensus (261) PRR P    RRGAAA    AGAS A  QPAA R APP AP
─────────────────────────────────────────────────────────────────── Section 7
                  (313) 313      320       330       340       350       364
HSV-1 (KOS) ICP0  (301) TVSSGGGGSRQSRAAVPRGASGPSGGVG------VVEAEAGRPRGRTGPLVN
HSV-2 (HG52) ICP0 (303) GVGSGSGGGPAVAAVVPRVASLPPAAGGGRAQARRVGEDAAAAEGRTPPAR-
        Concensus (313)    SG GG    A VPR AS P AA G      V  DAA   GRT P
─────────────────────────────────────────────────────────────────── Section 8
                  (365) 365      370       380       390       400       416
HSV-1 (KOS) ICP0  (347) RPAPLANNRDPIVISDSPPASPHRPP--------AAPMPGSAPRPGPPASAA
HSV-2 (HG52) ICP0 (354) --QPRAAQEPPIVISDSPPPSPRRPAGPGPLSFVSSSSAQVSSGPGGGGLPQ
        Concensus (365)    P A N  PIVISDSPP SP RP         AA    A PG   A
```

Fig. 13B

HSV-1s vs HSV-2s ICP0.apr

```
                                                                              Section 9
             (417) 417         430         440         450             468
HSV-1 (KOS) ICP0 (391) ASG-PARPRAAVAPCVRAPP-----PGPGPRAPAPGAEPAARPADARRVPQS
HSV-2 (HG52) ICP0 (404) SSGRAARPRAAVAPRVRSPPRAAAAPVVSASADAAGPAPPAVPVDAHRAPRS
      Concensus (417) ASG  ARPRAAVAP VRAPP      P     AAG  PAP DARP S
                                                                              Section 10
             (469) 469         480         490         500         510         520
HSV-1 (KOS) ICP0 (437) HSSLAQAANQEQSLCRARATVARGSGGPGVEGGHGPSRGAAPSGAAPSGAPP
HSV-2 (HG52) ICP0 (456) RMTQAQTDTQAQSLGRAGATDARGSGGPGAEGGPGVPRGTNTPGAAPH-AA-
      Concensus (469)    S AQ   Q QSL RA AT ARGSGGPG EGG G  RG   GAAP  A
                                                                              Section 11
             (521) 521         530         540         550         560         572
HSV-1 (KOS) ICP0 (489) LPSASVEQEAAVRPRKRRGS------GQENPSPQSTRPPLAP--AGAKRAAT
HSV-2 (HG52) ICP0 (506) -------EGAAARPRKRRGSDSGPAASSSASSSAAPRSPLAPQGVGAKRAAP
      Concensus (521)        AA RPRKRRGS        S    A R PLAP  GAKRAA
                                                                              Section 12
             (573) 573         580         590         600         610         624
HSV-1 (KOS) ICP0 (533) HPPSDSGPGGRGQG-------GPGTPLTS----------SAASASSSSASSS
HSV-2 (HG52) ICP0 (551) RRAPDSDSGDRGHGPLAPASAGAAPPSASPSSQAAVAAASSSSASSSSASSS
      Concensus (573)      DS  G RG G        G   P  S          SAASASSSSASSS
                                                                              Section 13
             (625) 625         630         640         650         660         676
HSV-1 (KOS) ICP0 (568) SAPTPAGATSSATG--AASSSASASSGGAVGALG-----GRQEETSLGPRAA
HSV-2 (HG52) ICP0 (603) SASSSSASSSSASSSSASSSSASSSAGGAGGSVASASGAGERRETSLGPRAA
      Concensus (625) SA S  AAASSSAS    AASSSASASAGGA GALA     G   ETSLGPRAA
                                                                              Section 14
             (677) 677         690         700         710             728
HSV-1 (KOS) ICP0 (613) SGPRGPRKCARKTRHAETS----GAVPAGGLTRYLPISGVSSVVALSPYVNK
HSV-2 (HG52) ICP0 (655) AP-RGPRKCARKTRHAEGGPEPGARDPAPGLTRYLPIAGVSSVVALAPYVNK
      Concensus (677) A  RGPRKCARKTRHAE       A  PA GLTRYLPIAGVSSVVALAPYVNK
                                                                              Section 15
             (729) 729         740         750         760         770         780
HSV-1 (KOS) ICP0 (661) TITGDCLPILDMETGNIGAYVVLVDQTGNMATRLRAAVPGWSRRTLLLPETAG
HSV-2 (HG52) ICP0 (706) TVTGDCLPVLDMETGHIGAYVVLVDQTGNVADLLRAAAPAWSRRTLLPEHAR
      Concensus (729) T TGDCLP LDMETG IGAYVVLVDQTGN A  LRAA  PAWSRRTLLPE A
                                                                              Section 16
             (781) 781         790         800         810         820         832
HSV-1 (KOS) ICP0 (713) NHVTPPEYPTAPASEWNSLWMTPVGNMLFDQGTLVGALDFRSLRSRHPWSGE
HSV-2 (HG52) ICP0 (758) NCVRPPDYPTPPASEWNSLWMTPVGNMLFDQGTLVGALDFHGLRSRHPWSRE
      Concensus (781) N V PPDYPT PASEWNSLWMTPVGNMLFDQGTLVGALDF  LRSRHPWS E
                                                                              Section 17
             (833) 833         848
HSV-1 (KOS) ICP0 (765) QGASTRDEGKQ-----
HSV-2 (HG52) ICP0 (810) QGAPAPAGDAPAGHGE
      Concensus (833) QGA
```

Fig. 13B
Continued

HERPES SIMPLEX VIRUS MUTANT ICP0 PROTEIN

CROSS-REFERENCE TO RELATED APPLICATIONS

This application claims the benefit of U.S. Provisional Patent Application No. 60/948,048, filed on Jul. 5, 2007, the disclosure of which is incorporated herein by specific reference.

This invention was made with government support under CA20260 awarded by the National Institute of Health. The government has certain rights in the invention.

BACKGROUND OF THE INVENTION

1. The Field of the Invention

The present invention relates to a mutant herpes simplex virus (HSV) ICP0 protein. More particularly, the present invention relates to a mutant HSV, mutant ICP0 protein, a vaccine or other composition having the mutant HSV and/or mutant ICP0, assay systems and reagents with the mutant HSV and/or mutant ICP0, and methods of making and using the same.

2. The Relevant Technology

Herpes simplex virus 1 and 2 (HSV-1 and HSV-2) are two species of the herpes virus family, herpesviridae, which cause infections in humans. Members of herpesviridae infect humans to cause a variety of illnesses including cold sores, chickenpox or varicella, shingles or herpes zoster (VZV), cytomegalovirus (CMV), and various cancers, and can cause brain inflammation (encephalitis). All viruses in the herpes family produce life-long infections. HSV-1 and HSV-2 are also called Human Herpes Virus 1 and 2 (HHV-1 and HHV-2) and are neurotropic and neuroinvasive viruses; they enter and hide in the human nervous system, accounting for their durability in the human body. HSV-1 is commonly associated with herpes outbreaks of the face known as cold sores or fever blisters, whereas HSV-2 is more often associated with genital herpes.

An infection by a herpes simplex virus (HSV) is marked by watery blisters in the skin or mucous membranes of the mouth, lips, or genitals. Lesions heal with a scab characteristic of herpetic disease. However, the infection is persistent and symptoms may recur periodically as outbreaks of sores near the site of original infection. After the initial, or primary, infection, HSV becomes latent in the cell bodies of nerves in the area. Some infected people experience sporadic episodes of viral reactivation, followed by transportation of the virus via the nerve's axon to the skin, where virus replication and shedding occurs. Herpes is contagious if the carrier is producing and shedding the virus. This is especially likely during an outbreak but possible at other times. There is no cure yet, but there are treatments which reduce the likelihood of viral shedding.

HSV is a common and significant human pathogen which causes a variety of diseases, ranging from cold sores to potentially blinding ocular infections and life-threatening encephalitis. HSV establishes lifelong latent infections in neuronal cells, which reactivate periodically. The HSV lifecycle can be described in two specific stages of infection: latent and productive. Latent infection is defined as a lack of production of infectious virus at the site. Productive infection can be characterized by the expression of nearly all (about 100) viral genes in epithelial cells and fibroblasts at the periphery and the sensory neurons that innervate the site of infection. One of the important HSV-1 and HSV-2 proteins in this process is Infected Cell Protein 0 (ICP0).

Infected Cell Protein 0 (ICP0) is a nuclear phosphoprotein, and is one of the first HSV-1 proteins to be expressed upon infection of cells in culture. ICP0 is a key determinant in the switch between latent and productive infections of HSV viruses. ICP0 is a potent transactivator of HSV gene expression, and can be considered essential for efficient viral replication, especially at low multiplicities. ICP0 transactivates all classes of HSV genes, immediately-early (IE), early, and late, as well as numerous cellular genes and genes of other viruses. ICP0 is an immediately-early (IE) transactivator, and E3 ubiquitin ligase, which disrupts nuclear domain 10 and inhibits the cellular interferon response. Due to these features, HSV-1, HSV-2, and ICP0 have been studied for indications of the pathogenesis of the viral infection. Research of ICP0 has shown that phosphorylation is important for ICP0 to function in the viral pathway.

BRIEF SUMMARY OF THE INVENTION

The present invention can include a mutant virus of herpes simplex virus type 1 (HSV-1) and/or herpes simplex virus type 2 (HSV-2). The mutant herpes simplex virus (HSV) has a mutation in at least one phosphorylation site of a protein involved in replication in order to inhibit phosphorylation of the site so as to prohibit or impair replication of HSV and/or the clinical severity of an HSV infection and/or HSV-mediated diseases. Mutations as described have been introduced into the HSV genome and/or ICP0 so as to provide mutant and replication impaired or deficient HSV. The mutant virus can be used in screening and/or developing anti-HSV agents (e.g., anti-HSV-1 and/or anti-HSV-2). The mutant HSV and/or ICP0 can treat, limit and/or prevent HSV infections.

In one embodiment, a mutant HSV-1 can include a mutant ICP0 having a mutation in at least one phosphorylation site, wherein the mutation can be configured to inhibit phosphorylation of at least one phosphorylation site. The mutation can be a substitution of at least one serine and/or threonine amino acid between amino acid 505 and amino acid 528 by an amino acid, such as alanine. In addition, the mutation can be any amino acid substitutions other than alanine to block the phosphorylation. Also, the mutation can be amino acid insertions, deletions, substitutions, and like mutations introduced at the phosphorylation sites in region III or other regions of ICP0 in order to block phosphorylation. The mutation in HSV-1 ICP0 could be a substitution of at least one of the four phosphorylation sites of ICP0, S508, S514, S517, or T518, which include a serine or threonine amino acid. The substation of amino acid alanine can block phosphorylation at these phosphorylation sites.

In one embodiment, a mutant HSV-2 can include a mutant ICP0 having a mutation in at least one phosphorylation site, wherein the mutation can be configured to inhibit phosphorylation of at least one phosphorylation site. The mutation can be a substitution of at least one serine and/or threonine amino acid between amino acid 518 and amino acid 531 by an amino acid, such as alanine. In addition, the mutation can be any amino acid substitutions other than alanine to block the phosphorylation. Also, the mutation can be amino acid insertions, deletions, substitutions, and like mutations introduced at the phosphorylation sites in a region that corresponds with region III or other regions of ICP0 in order to block phosphorylation. The mutation in HSV-2 ICP0 could be a substitution of at least one of the phosphorylation sites of HSV-2 ICP0 at any of the eight serines from amino acid 518 to amino acid 531. The substation of amino acid alanine can block phosphorylation at these phosphorylation sites.

In one embodiment, the mutant HSV-1, mutant HSV-2, and or mutant ICP0 can be used in a vaccine or a composition to reduce and/or inhibit HSV-1 and/or HSV-2 replication, and thereby reduce or prevent HSV-1 and/or HSV-2 infections or complications associated with HSV-1 and/or HSV-2 infections and/or HSV-mediated diseases. The mutant HSV-1 and/or mutant HSV-2 can have a mutant ICP0 that has mutations in ICP0 at the phosphorylation site(s) so as to inhibit HSV-1 and/or HSV-2 replication in comparison with wild-type HSV-1 or HSV-2. Also, the mutant HSV-1 and/or mutant HSV-2 having a mutant ICP0 with the mutation can inhibit replication in neurons. Accordingly, a vaccine can have a therapeutically effective amount of mutant HSV, mutant HSV-1, mutant HSV-2, and/or mutant ICP0 with reduced or inhibited phosphorylation.

In one embodiment, the mutant HSV-1 virus, mutant HSV-2, and/or the mutant ICP0 protein can be introduced into an individual in a therapeutically effective amount that has been or may become infected with an HSV infection (e.g., HSV-1 and/or HSV-2 infection). The mutant HSV-1 virus, mutant HSV-2, and/or the mutant ICP0 protein can inhibit the HSV-1 virus and/or HSV-2 virus from replicating. Thus, the mutant HSV-1, mutant HSV-2, and/or mutant ICP0 protein in a therapeutically effective amount can treat, limit and/or prevent HSV-1 or HSV-2 infections or disease states associated with HSV-1 or HSV-2 infection.

In one embodiment, the mutant HSV-1 and/or HSV-2 can be used in screening and/or developing anti-HSV-1 and/or anti-HSV-2 therapeutic agents. Such therapeutic agents can be specific for HSV-1 or HSV-2 or be therapeutic with respect to HSV-1 and HSV-2. The method can include: providing a first and second cell of the same cell type that is capable of being infected with HSV-1 and/or HSV-2; introducing a mutant HSV-1 and/or HSV-2 having a mutant ICP0 into the first cell; introducing a wild type HSV-1 and/or HSV-2 having wild type ICP0 into the second cell; introducing an agent to be screened for activity that inhibits phosphorylation of the wild type ICP0 into the second cell; and comparing the replication of the mutant HSV-1 and/or mutant HSV-2 and the wild type HSV-1 and/or wild type HSV-2, wherein the replication of mutant HSV-1 and/or mutant HSV-2 being similar to the wild type HSV-1 and/or wild type HSV-2 is an indication that the agent is an active agent that inhibits phosphorylation of wild type ICP0. An agent that inhibits phosphorylation of ICP0 can be an anti-HSV-1 and/or anti-HSV-2 therapeutic agent.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 1A-1C illustrate the locations of ICP0 functional domains, phosphorylation sites, and phosphorylation site mutants.

FIG. 13A is a sequence alignment of the ICP0 of HSV-1 strain 17 (SEQ ID NO: 2) an HSV-2 strain HG52 (SEQ ID NO: 8).

FIG. 13B is a sequence alignment of the ICP0 of HSV-1 strain KOS (SEQ ID NO: 4) an HSV-2 strain HG52 (SEQ ID NO: 8).

DETAILED DESCRIPTION OF THE PREFERRED EMBODIMENTS

Figure 2A:
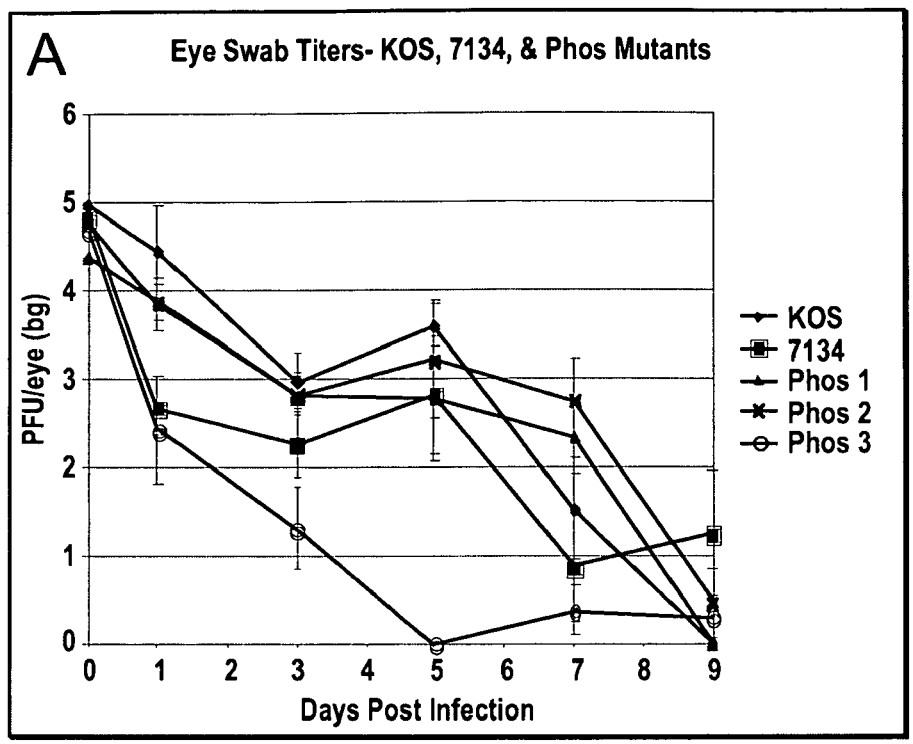
FIGS. 2A-2B include graphs that illustrate eye swab titers of wild-type (KOS), ICP0 null mutant (7134), phosphorylation site mutants (Phos 1, 2, and 3), and their marker-rescue (MR) viruses during acute infection of mice.

Herpes simplex virus type 1 (HSV-1) infected cell protein 0 (ICP0) is an immediate-early (IE) transactivator and E3 ubiquitin (Ub) ligase, which disrupts nuclear domain 10 (ND10) and inhibits the cellular interferon response. Cellular functions of ICP0 are involved in viral gene expression, viral replication, and reactivation from latency. ICP0 is a nuclear protein that is phosphorylated, a post-translational modification that acts as a key regulator of many viral and cellular proteins.

ICP0 is the product of gene IE-1 (or α0), which is in the repeated sequences bounding the long unique segment of the HSV-1 genome. The primary transcript of the IE-1 gene is one of the few produced by HSV-1 that is spliced. The ICP0 protein product of HSV-1 strain 17 contains 775 amino acids. This protein has been named as Vmw110 or IE110 in many older publications, but now the designation ICP0 has been almost universally adopted.

Phosphorylation is a critical regulator of HSV-1 ICP0 function in cell culture. Three major regions of phosphorylation of ICP0 (amino acids 224-232, 365-371, and 508-518) have been identified, and mutant viruses carrying mutations within each region (termed Phos 1, Phos 2, and Phos 3) have been constructed. In cell culture studies, the plating efficiencies of Phos 1 and 3 are distinct from that of wild-type virus, in that both exhibit reduced efficiency of plaque formation. Notably, for Phos 3, this defect is apparent only in the presence of interferon-beta. All three Phos mutants have reduced reactivation efficiencies, and Phos 1 and 3 have significantly reduced pathogenicities compared to wild-type HSV-1. The greatest decline in viral pathogenicity is observed with Phos 3, whose mutations overlap the nuclear localization signal of ICP0.

The following references, which are incorporated herein by specific reference, provide information regarding HSV-1 and/or ICP0: ICP0 phosphorylation site mutations. Davido D J, von Zagorski W F, Lane W S, Schaffer P A; Phosphorylation site mutations affect herpes simplex virus type 1 ICP0 function, J Virol. 2005 January; 79(2):1232-43; Construction of HSV-1 mutants in the ICP0 loci, Herpes simplex virus type 1 ICP0 plays a critical role in the de novo synthesis of infectious virus following transfection of viral DNA, J Virol. 1989 November; 63(11):4579-89, Protocols for HSV-1 infection and assays in mice, Halford W P, Schaffer P A, ICP0 is required for efficient reactivation of herpes simplex virus type 1 from neuronal latency, J Virol. 2001 April; 75(7):3240-9; and Review of HSV-1 ICP0, Alpha Herpesviruses: Molecular and Cellular Biology publisher: Caister Academic Press, Editor: R. M. Sandri-Goldin University of California, Irvine, Calif., USA, Publication date: Aug. 1, 2006, Chapter 3: Roles of ICP0 during HSV-1 infection, Roger Everett; Perry, L. J., Rixon, F. J., Everett, R. D., Frame, M. C. and McGeoch, D. J. Characterization of the IE110 gene of herpes simplex virus type 1, J. Gen. Virol. 67 (PT 11), 2365-2380 (1986).

It has now been found that mutation of phosphorylation sites of viral regulatory proteins, such as ICP0, in HSV-1 can alter their DNA replication activity, affecting both their biochemical and biological functions. It has been demonstrated that phosphorylation is an important modulator of the functions of infected cell proteins (ICPs). Mutant viruses having mutations that affect an ICP's transactivating activity to replicate, establish latency, and reactivate from latency may be inefficient for infection and are sensitive to the cellular antiviral factors, interferon. Although early studies demonstrated that ICPs are phosphorylated, the location of specific phosphorylation sites on ICPs, and the kinases that phosphorylate ICPs and the functional relevance of ICP phosphorylation to HSV replication have been largely unknown. Previous studies demonstrated a link between ICP0's posttranslational modification state and HSV-1 transactivating activity, which includes posttranslational phosphorylation. In addition, the kinase UL13 has been shown to be required to achieve maximal levels of ICP0 phosphorylation during viral infection, and can phosphorylated ICP0 in vitro.

Accordingly, posttranslational phosphorylation of specific amino acid sites of ICP0 have now been identified. The identified ICP0 phosphorylation site were further investigated in order to determine the functional relevance to HSV-1 replication and pathogenesis. Specific ICP0 phosphorylation sites have now been determined, and mutations to such sites have been identified that reduce or inhibit phosphorylation of ICP0 so as to reduce or inhibit the reproduction of HSV-1 and prevent its reactivation.

In view of the foregoing, the present invention includes a mutant virus of herpes simplex virus type 1 (HSV-1) and/or a mutant ICP0. The mutant HSV-1 expressing mutant ICP0 or mutant ICP0 alone has a mutation in at least one phosphorylation site that inhibits phosphorylation of the site so as to prohibit or impair replication of HSV-1 and/or the clinical severity of HSV-1-mediated diseases. The mutant HSV-1 and/or mutant ICP0 can be used in vaccines, pharmaceutical compositions, and other compositions, such as those used in diagnostics, screening assays to identify molecules or substances that promote or inhibit phosphorylation. Additionally, the present invention includes the methods of mutating the ICP0 and methods of manufacturing mutant HSV-1 having the mutant ICP0. Moreover, the present invention includes methods of using the mutant HSV-1 and/or mutant ICP0 in the treatment and/or prevention of HSV-1 infection, and in assays for studying HSV-1 and identify additional substances that may affect HSV-1 infection.

The mutations have been introduced into a viral regulatory gene, infected cell protein 0 (ICP0), which inhibits phosphorylation in at least one region of the protein. One of the regions of the mutant HSV-1 is referred to herein as "Phos 3," which is described in more detail below. At least four putative phosphorylation sites, which include serine and threonine amino acids as well as possible other amino acids, in the Phos 3 region can be mutated to another amino acid in order to block phosphorylation at the phosphorylation sites. For example, the amino acid alanine can be substituted at a phosphorylation site to block phosphorylation at any of these phosphorylation sites. However, amino acid substitutions other than alanine may also block the phosphorylation. Additionally, amino acid insertions, deletions, substitutions, and like mutations can be introduced at the phosphorylation sites in order to block phosphorylation.

At least one region of phosphorylation in ICP0, Phos 3, has been identified as being involved in HSV-1 replication. Accordingly, mutations to the phosphorylation site(s) of Phos 3 can be introduced so as to provide mutant and replication deficient HSV-1. The mutant HSV-1 having a mutant ICP0 within inhibited phosphorylation inhibits HSV-1 replication in comparison with wild-type HSV-1. Also, the mutant HSV-1 having mutant ICP0 can inhibit or impair replication in neurons.

A mutant HSV-1 virus that includes a mutated ICP0 protein (e.g., Phos 3) has been shown in animal studies to be inhibited from properly replicating in sites that are common place for HSV-1 replication. The animal studies have shown that the mutant ICP0 protein impairs replication of HSV-1 in the eyes, and substantially no infectious HSV-1 virus has been detected in the neurons of the animals infected with the mutant HSV-1 virus in the initial stages of infection. Mice that have been infected with the mutant HSV-1 virus that includes a mutated ICP0 protein visually look like uninfected mice. Thus, the studies, which are discussed in more detail herein, have shown that the mutant HSV-1 virus that includes a mutated ICP0 protein is apathogenic or inhibited from replicating.

It can be advantageous to reduce or inhibit the phosphorylation of at least one site on the ICP0 protein. Also, wild type phosphorylation sites that are not mutated can be used in the present invention in finding therapeutics for HSV-1 that inhibits phosphorylation. For example, an inhibitor can be identified that inhibits phosphorylation of the wild type phosphorylation sites, so as to have replication similar to the mutant HSV-1.

A mutant ICP0, such as Phos 3, can be dominant/negative, and thereby inhibit the interaction of the mutant ICP0 with other proteins that normally interact with the ICP0 protein in HSV-1 replication. That is, the mutant ICP0 can block binding to another protein, such as a cellular protein or other HSV-1 protein in the replication pathway. For example, the mutant ICP0 protein can inhibit binding with such other proteins in the replication cycle, thereby providing a dominant/negative characteristic. As such, the mutant ICP0 can inhibit other proteins, to which ICP0 typically associates, from performing normal replication functions because the mutant ICP0 protein inhibits normal function. As such, the mutant virus can be introduced into an infected site and/or potentially infected site and the dominant/negative characteristic can inhibit replication the wild type virus, if present at that site. Thus, the mutant ICP0 protein inhibits other proteins from functioning, which can be used as a treatment of prophylactic with respect to HSV-1 infections or other disease states associated with HSV-1 infection.

The mutant HSV-1 virus having mutant ICP0, as described, can be inhibited from replicating in neurons during the initial stages of the infection. A control HSV-1 that is substantially devoid of expressing the ICP0 protein is still capable of replicating in neuronal cells; however, mutating the ICP0 protein inhibits replication in neuronal cells. As such, the mutant ICP0 can function as a type of dominant/negative because it does not replicate in neuron cells. Also the mutant HSV-1 and/or mutant ICP0 can also reduce or inhibit blephartis (eyelid disease), keratitis (corneal opacity), and latency.

The mutant HSV-1 virus and/or the mutant ICP0 protein can be introduced into an individual that has been infected or may be infected with a wild type HSV-1. The mutant HSV-1 virus and/or the mutant ICP0 protein can inhibit the wild type HSV-1 virus from replicating. This can allow for the mutant HSV-1 virus and/or the mutant ICP0 protein to be used in treatment and/or prophylactic protocols.

The mutant HSV-1 virus described herein as having the mutant ICP0 protein can be used in various experimental and therapeutic procedures. A significant use of the mutant HSV-1 virus can be as a vaccine against HSV-1. Also, the biological studies with the mutant HSV-1 and mutant ICP0 indicate the phosphorylation sites can be used in screening and/or developing active agents that can inhibit such phosphorylation and/or can be used as anti-HSV-1 drugs. For example, drug screens can be established to identify small molecules or other active agents that inhibit the action of viral and cellular kinases that inhibit phosphorylation at these sites on the ICP0 protein. Inhibition of ICP0 phosphorylation can inhibit HSV-1 replication, and thereby inhibit HSV-1 infections.

In one embodiment, the present invention can include a mutant virus of herpes simplex virus type 1 (HSV-1) that has impaired or inhibited replication. The mutant virus can have a mutation in at least one phosphorylation site of a protein, such as ICP0, involved in HSV-1 replication so as to impair or inhibit replication. Also, the mutant ICP0 can have at least one mutation to inhibit phosphorylation of a phosphorylation site so as to impair or inhibit replication of HSV-1 and/or reduce clinical severity of HSV-1-mediated diseases so as to treat and/or prevent such HSV-1-mediated diseases. The mutant virus can also have at least one ICP0 mutation that inhibits phosphorylation of a phosphorylation site so that the mutant virus can be used in diagnostic assays as well as in screening and/or developing therapeutic agents that treat and/or prevent HSV-1 infection. Moreover, the mutant virus can include a mutation in at least one phosphorylation site of ICP0 that allows the mutant virus to be used in a vaccine or other pharmaceutical composition useful for treating and/or preventing HSV-1 infections or HSV-1-mediated diseases.

Accordingly, a mutant ICP0 can have a mutation in at least one phosphorylation site, wherein the mutation can be configured to inhibit phosphorylation of said at least one phosphorylation site. In one aspect, the mutation is an amino acid substitution, insertion, deletion, or combination thereof. In one aspect, the mutation is in region III. In one aspect, the mutation is between amino acid 505 and amino acid 528. In one aspect, the mutation is a substitution of at least one serine and/or threonine amino acid between amino acid 505 and amino acid 528 with a different amino acid. In one aspect, the mutation is a substitution of at least one serine and/or threonine amino acid between amino acid 505 and amino acid 528 with an alanine amino acid or other phosphorylation-inhibiting amino acid. In one aspect, the mutation is a substitution of at least one serine and/or threonine amino acid in at least one of amino acids S508, S514, S517, or T518 with an alanine amino acid or other phosphorylation-inhibiting amino acid. In one aspect, the mutation is at amino acid 508, 514, 517, and/or 518 of an ICP0 amino acid sequence as shown in the Sequence Listing, which can be any one, any two, any three, and/or all four of the identified amino acids.

In one embodiment, the mutant HSV-1 and/or mutant ICP0 can be used in a vaccine or other composition to inhibit HSV-1 replication, and thereby prevent HSV-1 infections. Data for the mutant HSV-1 having mutant ICP0 indicate that alterations of ICP0 at the phosphorylation site(s) inhibits HSV-1 replication in comparison with wild-type HSV-1. Also, the mutant HSV-1 having mutant ICP0 with the mutation was shown to be inhibited for replication in neurons. The experimental protocols and data are described in more detail herein.

In one embodiment, the mutant HSV-1 and/or the mutant ICP0 protein can be introduced into an individual that has been infected or may become infected with the HSV-1 infection. The mutant HSV-1 virus and/or the mutant ICP0 protein can be used to inhibit the HSV-1 virus from replicating. Thus, the mutant HSV-1 virus and/or mutant ICP0 protein can treat, limit and/or prevent HSV-1 infections as well as disease states associated with HSV-1.

In one embodiment, the mutant HSV-1 and/or the mutant ICP0 protein can be used in screening and/or developing therapeutic agents that treat and/or prevent HSV-1 infection or other disease states associated with HSV-1. An example of screening can include: providing a first and second cell of the same cell type that is capable of being infected with HSV-1; introducing a mutant HSV-1 having a mutant ICP0 into the first cell, introducing a wild type HSV-1 having wild type ICP0 into the second cell; introducing an agent to be screened for activity that inhibits phosphorylation of the wild type ICP0 into the second cell; and comparing the replication of the mutant HSV-1 and the wild type HSV-1, wherein the replication of mutant HSV-1 and the wild type HSV-1 being similar is an indication that the agent is an active agent that inhibits phosphorylation of wild type ICP0. Also, the mutant HSV-1 and/or the mutant ICP0 protein can be used in other screening techniques.

I. Mutant HSV-1/ICP0

The present invention includes a mutant HSV-1 that has a mutant ICP0 that is mutated to reduce or inhibit posttranslational phosphorylation. Accordingly, the mutant HSV-1 can include a mutant gene that encodes for the mutant ICP0 as described herein. As such, the mutant HSV-1 includes a mutant protein which is essential for efficient production of infectious virus in which the mutant protein has been inactivated. The mutant HSV-1 can be grown in a cell which has a heterologous nucleotide sequence which allows the cell to express the mutant protein encoded by the inactivated viral gene. Such a mutant HSV-1 with a genome defective in respect to ICP0 can protect a susceptible species immunized therewith against infection by the corresponding wild-type HSV-1. As discussed below, the mutant HSV-1 can be included in a vaccine used to treat and/or prevent infectious for cells of a susceptible species, e.g. a mammalian species, immunized therewith.

The mutant HSV-1 having mutant ICP0 with alterations of ICP0 at the phosphorylation site(s) impairs or inhibits HSV-1 replication in comparison with wild-type HSV-1. Also, the mutant HSV-1 having mutant ICP0 has inhibited or reduced replication in both peripheral and central nervous systems. Accordingly, the mutant HSV-1 expressing mutant ICP0 can be used in a vaccine to inhibit HSV-1 replication and thereby treat and/or prevent HSV-1 infections.

The three ICP0 phosphorylation site mutants (e.g., Phos 1, Phos 2, and/or Phos 3) can be mutated so as to impair or inhibit replication and/or reactivation of HSV-1 in vivo. Of the viral mutants, mutations in Phos 3 can have the greatest effect on all phases of the HSV-1 life-cycle in vivo. In contrast to the ICP0 null mutant 7134, Phos 3 has reduced or inhibited replicate in neurons of the trigeminal ganglia (TG) during acute infection, days 1-9 post infection (p.i.). The phosphorylation sites mutated in Phos 3 can reduce or inhibit replication in TG during the initial stage of HSV-1 infection. This reduction or inhibition replication can produce no visible signs of viral pathogenesis and an impaired reactivation phenotype. Phos 1 can affect viral replication and pathogenesis, although its defects may be less pronounced as those of Phos 3. Phos 2 may be considered the least attenuated mutant of the three mutant HSV-1 viruses. Thus, the phosphorylation sites in Phos 2 are not as necessary to ICP0 function and HSV-1 replication in eyes as Phos 3 or even Phos 1.

Accordingly, Phos 1 mutations can impair acute replication in eyes and TG and reactivation from latency. Phos 2 mutations can impair acute replication in TG and reactivation from latency. Phos 3 mutations can impair ocular replication, completely inhibit acute TG replication, and significantly reduce reactivation. As such, Phos 3 shows the greatest diminution of the three mutant viruses. Also, all three ICP0 phosphorylation regions may be required for efficient viral replication and reactivation from latency, and a mutation to one or more of the regions can reduce or inhibit replication. The Phos 3 mutant form of ICP0 appears to interfere with a viral or cellular function essential for viral growth in neurons.

Previous reports have shown that the level of acute replication in neurons directly influences the establishment of and reactivation from latency. Because the Phos mutants reduced or inhibited reactivation, unmutated ICP0 can be required for establishing an efficient latent infection. For all three phosphorylation site mutant viruses (e.g., Phos 1, Phos 2, and/or Phos 3), the phenotypes observed with the Phos mutants are due to the phosphorylation site mutations and not from secondary mutations present in the viral genome.

The mutation in the HSV-1 genome and/or ICP0 can include amino acid insertions, deletions, substitutions, and like mutations introduced at the phosphorylation sites in region III or other regions of ICP0 in order to block phosphorylation. The mutant HSV-1 expressing mutant ICP0 with inhibited phosphorylation in at least Phos 3 can have reduced or inhibited HSV-1 replication, and thereby treat and/or prevent HSV-1 infections. For example, the mutation can be a substitution of at least one serine and/or threonine amino acid between amino acid 505 and amino acid 528 by amino acid alanine. In addition, the mutation can be any amino acid substitutions other than alanine to block the phosphorylation. The mutation in HSV-1 could be substitution of at least one of the four phosphorylation sites of ICP0, S508, S514, S517, or T518, which include serine or threonine amino acid, by the amino acid alanine to block phosphorylation at these phosphorylation sites.

In one embodiment, the mutation in HSV-1 could be introduced by site-directed mutagenesis. However, any method known or developed for preparing a mutant HSV-1 and/or mutant ICP0 as described herein can be used for preparing the mutant HSV-1 and/or mutant ICP0 of the present invention.

II. Mutant HSV-1 and/or ICP0 Vaccine

In accordance with the discussions of mutant HSV-1 and/or mutant ICP0, either the mutant HSV-1 and/or mutant ICP0 can be used in a vaccine. Methods of preparing vaccines to include a mutant virus, such as mutant HSV-1, and/or a mutant protein, such as mutant ICP0, are well established in the art of vaccines.

A vaccine can be prepared which includes mutant HSV-1 and/or mutant ICP0, as described herein, together with one or more excipients and/or adjuvants. The mutant HSV-1 viral genome and/or mutant gene encoding ICP0 may be included in the vaccine. The vaccine can contain genetic material, such as a heterologous gene insert expressing the mutant protein. In such a case, the mutant ICP0 can be expressed in cells of a susceptible species immunized with the vaccine containing mutant HSV-1 and/or mutant ICP0. Immunity against wild type HSV-1 can thereby be conferred in a species and/or tissue normally susceptible to HSV-1 infection.

Accordingly, the mutant HSV-1 expressing mutant ICP0 with inhibited phosphorylation in at least Phos 3 (i.e., having mutated phosphorylation sites) can be used in a vaccine to reduce or inhibit HSV-1 replication, and thereby treat and/or prevent HSV-1 infections or other disease states related to or caused by HSV-1 infections. The present invention may trigger an immune response of a subject, which should train the vaccinated person's immune system to fight a wild type HSV-1. The mutant HSV-1 or mutant ICP0 may also reduce frequency and severity of recurrent disease.

Also, a vaccine having the mutant HSV-1 and/or mutant ICP0 may be taken by subjects who have been infected by HSV-1 during its latent or recurrence period to impair or inhibit its reproduction, and thereby impair or prevent its recurrence.

The vaccine can be a pharmaceutical preparation as is standard in the art. The vaccine can be administrable subcutaneously, intramuscularly, intra-dermally, epithelially, nasally, vaginally, or orally and can comprise excipient(s) suitable for the selected administration route. The pharmaceutical preparation can be capable of protecting a patient immunized therewith against infection or the consequences of infection with HSV-1 by a corresponding wild-type virus.

Also, the present invention can include an assembly comprising a pharmaceutical for prophylaxis or for therapy as described herein in a container. The container can contain the mutant HSV-1 and/or mutant ICP0. The container can be a pre-filled syringe or glass vial/ampoule with printed instructions on or accompanying the container concerning the administration of the pharmaceutical to a patient to prevent or treat conditions caused by infection with HSV-1.

A vaccine or other pharmaceutical preparation containing the mutant HSV-1 and/or mutant ICP0 as described can be prepared in accordance with methods well known in the art wherein the mutant is combined in admixture with a suitable vehicle. Suitable vehicles include, for example, saline solutions, or other additives recognized in the art for use in compositions applied to prevent viral infections. Such vaccines will contain an effective amount of the mutant as hereby provided and a suitable amount of vehicle in order to prepare a vaccine useful for effective administration to the host Dosage rates of the vaccine can be determined according to known methods. For example, dosage rate may be determined by measuring the optimum amount of antibodies directed against a mutant resulting from administration of varying amounts of the mutant in vaccine preparations.

A vaccine comprising a mutant HSV-1 and/or mutant ICP0 as herein provided can be formulated according to known methods to provide therapeutically useful compositions, whereby the mutant HSV-1 and/or mutant ICP0 is combined in admixture with a pharmaceutically acceptable carrier vehicle. Suitable vehicles and their formulation are described in 'Remington's Pharmaceutical Sciences' (Mack Publishing Co, Easton, Pa., ed. A R Gennaro), by E W Martin, and by F Rola, which is incorporated herein by specific reference. Such compositions contain an effective amount of the mutant HSV-1 and/or mutant ICP0 together with a suitable amount of carrier vehicle in order to prepare therapeutically acceptable compositions suitable for effective administration to the host Vaccines can be prepared with excipients which are pharmaceutically acceptable and compatible with the active ingredient. Suitable excipients are, for example, water, saline, dextrose, glycerol, trehalose, or the like and combinations thereof. In addition, if desired, the vaccine may contain minor amounts of auxiliary substances such as other stabilizers and/or pH buffering agents, which enhance the stability and thus the effectiveness of the vaccine Vaccines may be configured to be administered parenterally, by injection, for example, subcutaneously, intraepithelially (with or without scarification). Additional formulations which are suitable for other modes of administration, such as oral, vaginal and nasal formulations are also provided. Oral formulations include such normally employed excipients as, for example, pharmaceutical grades of trehalose mannitol, lactose, starch, magnesium stearate, sodium saccharine, cellulose, magnesium carbonate, and the like. The compositions may take the form of solutions, suspensions, tablets, pills, capsules sustained release formulations or powders Vaccines can be administered in a manner compatible with the dosage formulation, and in such amount as will be prophylactically effective. The quantity to be administered will have been predetermined from preclinical and clinical (phase I) studies to provide the optimum immunological response The vaccine may be given in a single dose schedule or in a multiple dose schedule, as needed or desired. A multiple dose schedule is one in which a primary course of vaccination with 1-3 separate doses, followed by other doses given at subsequent time intervals required to maintain and or re-enforce the immune response. For example, at 1-4 months for a second dose, and if needed, a subsequent dose(s) after several months. The dosage regimen will also, have been determined from preclinical and clinical studies as maintaining the optimum immunological response over time.

Also, the vaccine can be prepared with genetic information of the mutant HSV-1 and/or mutant ICP0. This includes genetic information that can cause the production of mutant HSV-1 and/or mutant ICP0. The genetic information can be prepared in any manner that allows for inclusion in a vaccine that causes production of the mutant HSV-1 and/or mutant ICP0 in a subject so as to immunize the subject against wild type HSV-1. Sequences that can be included in the genetic information can be found in the Sequence Listing.

The vaccine including the mutant HSV-1 and/or mutant ICP0 may be taken by subjects during occurring or recurring infections to curtail the severity and timeframe of symptoms. The vaccine including mutant HSV-1 and/or mutant ICP0 may also reduce frequency and recurrent disease. Single injection of mutant HSV-1 expressing mutant ICP0 and/or the mutant ICP0 protein may provide life-long protection against recurrent outbreaks. However, multiple administrations may be utilized. The vaccine of the present invention can improve treatment and prevention of HSV-1 infections and other disease states related to HSV-1 infection. Existing anti-HSV-1 treatments must be taken during recurring infections and only curtail the severity and timeframe of symptoms. By contrast, the present invention may be applied to a subject during latent infection of HSV-1 to impair or prevent recurrence. The vaccine can also impair or prevent spreading the disease. Mutant HSV-1 expressing mutant ICP0 and/or mutant ICP0 can impair or inhibit the reproduction or reactivation of HSV-1, where HSV-1 is most contagious during reactivation.

Additionally, the mutant HSV-1 and/or mutant ICP0 can also be included in vaccines, as well as methods of treatment and/or prevention, to reduce or inhibit blephartis (eyelid disease), keratitis (corneal opacity), and latency. Methods of treating and/or preventing blephartis (eyelid disease), keratitis (corneal opacity), and latency can include providing the mutant HSV-1 and/or mutant ICP0 to a subject. The mutant HSV-1 and/or mutant ICP0 to a subject can be in the form of a pharmaceutical composition, such as a vaccine.

III. Cell Having Mutant HSV-1/Mutant ICP0

The present invention also provides a cell having the mutant HSV-1 and/or mutant ICP0. This can include cells that include genetic material that encodes for the production of the mutant HSV-1 and/or mutant ICP0. The cell can be any type of cell; however, it can be preferable for the cell to be a cell type that is infected with wild type HSV-1. Also, the cell can be a cell type for use in preparing the mutant HSV-1 and/or mutant ICP0. Such cells are well known in the art. For example, the cell can be a host cell, such as a recombinant eukaryotic cell line containing the gene (a) encoding mutant HSV-1 and/or mutant ICP0. A cell which includes or provides the mutant HSV-1 and/or mutant ICP0 can be used to grow the mutant HSV-1 and/or mutant ICP0 in tissue culture.

In one embodiment, the cell having mutant HSV-1 and/or mutant ICP0 or genetic material encoding for the mutant HSV-1 and/or mutant ICP0 can be a Vero cell or L7 cell. Vero cells, an African green monkey kidney cell line, can be obtained from the American Type Cell Culture (ATCC, Manassas, Va.) and propagated in Dulbecco's modified Eagle's medium (DMEM) supplemented with 10% fetal bovine serum (FBS) as described previously in the art. Vero cells can be stably transformed with the gene (a) encoding for mutant HSV-1 and/or mutant ICP0, and passaged as described in the art.

IV. Screening Assays

The mutant HSV-1 and/or mutant ICP0 can be used in screening assays to identify an agent that inhibits or impairs phosphorylation of ICP0. Accordingly, the mutant HSV-1 and/or mutant ICP0 can be used as a control and the agent can be screened against a wild type HSV-1 and/or ICP0 in order to determine whether or not it induces a phenotype similar to mutant HSV-1 and/or mutant ICP0.

In one embodiment, the mutant HSV-1 can be used in screening and/or developing anti-HSV-1 therapeutic agents. The method can include: providing a first and second cell of the same cell type that is capable of being infected with HSV-1; producing a mutant HSV-1 having a mutant ICP0 into the first cell; producing a wild type HSV-1 having wild type ICP0 into the second cell; introducing an agent to be screened for activity that inhibits phosphorylation of the wild type ICP0 into the second cell, and comparing the replication of the mutant HSV-1 and the wild type HSV-1, wherein the replication of mutant HSV-1 and the wild type HSV-1 being similar is an indication that the agent is an active agent that inhibits phosphorylation of wild type ICP0.

The screening assays can be used with various compounds from a library of compounds. The library of compounds can be screened so as to determine which compounds are effective in inhibiting phosphorylation of ICP0. Also, the library of compounds can be screened so as to determine which compounds are effective in inhibiting replication of HSV-1.

V. Polynucleotide/Polypeptide Sequences

In one embodiment, the present invention includes a polynucleotide sequence that encodes for the production of mutant HSV-1 and/or mutant ICP0. Also, the present invention can include a polypeptide sequence of a mutant ICP0. Examples of such polynucleotide and polypeptide sequences related to mutant HSV-1 and/or mutant ICP0 are included in the Sequence Listing. The Sequence Listing shows a comparison of HSV-1 strains 17 and KOS IE1 gene sequences. Relative to strain 17, KOS strain is: A316V, del 331-333, ins 486/487 PSGAP, del 492, A576T, A580T, M716T. In addition, there are several non-coding changes in the coding regions. KOS intron 1 has a substantial insertion of related short repeat sequences and other minor insertions, deletions and substitutions. KOS intron 2 has insertions and deletions that affect and lengthen the ICP0R product (that produced by failure to remove intron 2 from the mRNA). Accordingly, HSV-1 ICP0 can be obtained from strain KOS, which is slightly different from HSV-1 strain both at the nucleotide and protein levels. The protein and DNA sequences for the ICP0 coding region for strains 17 and KOS are included in this disclosure.

VI. HSV-2

[0079] Additionally, the sequence alignments were prepared between ICP0 proteins from HSV-1 strain KOS and HSV-2 strain HG52 (FIG. 13B), and HSV-1 strain 17 and HSV-2 strain HG52 (FIG. 13A). The sequence alignments indicate that a mutant HSV-2 and/or mutant HSV-2 ICP0 can be prepared as described in connection with mutant HSV-1 and/or mutant ICP0. The ICP0 phosphorylation sites in HSV-1 from amino acids 508-518 appears to be homologous to HSV-2 amino acids 518-531, depending on the alignment. HSV-1 ICP0 serine 508 is conserved as HSV-2 ICP0 serine 518. Depending on the strain used in the alignment, either HSV-1 ICP0 serine 514 is conserved as HSV-2 ICP0 serine 530 (with strain KOS) or HSV-1 ICP0 serine 517 is conserved as HSV-2 ICP0 serine 530 (with strain 17). Also, for HSV-1 ICP0, there are 3 serines and 1 threonine from amino acid 508-518, and for HSV-2 ICP0, there are 8 serines from amino acid 518-531.

The homology between ICP0 proteins in HSV-1 strains and HSV-2 strains provides an indication that the mutations of ICP0 described in connection with HSV-1 can also be applied to HSV-2. As such, the HSV-2 and ICP0 of HSV-2 can be mutated in substantially the same manner as the mutant HSV-1 and/or mutant ICP0 as described herein. The mutation in the HSV-2 genome and/or HSV-2 ICP0 can include amino acid insertions, deletions, substitutions, and like mutations introduced at the phosphorylation sites in region III or other regions of the HSV-2 ICP0 in order to block phosphorylation. The mutant HSV-2 expressing mutant ICP0 with inhibited phosphorylation in amino acid positions that correspond with HSV-1 can be implemented in order to have reduced or inhibited HSV-2 replication, and thereby treat and/or prevent HSV-2 infections. For example, the mutation can be a substitution of at least one serine and/or threonine amino acid between amino acids of the HSV-2 ICP0 that correspond with amino acids 505 through by amino acid alanine. In addition, the mutation can be any amino acid substitutions other than alanine to block the phosphorylation. The mutation in HSV-2 could be substitution of at least one of the phosphorylation sites that are conserved between HSV-1 and HSV-2. Thus, the information and examples described herein are applicable also to HSV-2.

The mutations of HSV-2 ICP0 can correlate with phosphorylation sites in HSV-2 ICP0 amino acids 518-531. For example, the mutation can be at the serine or threonine in the following: HSV-2 ICP0 at amino acid 518; HSV-2 ICP0 at amino acid 530; HSV-2 ICP0 at amino acid 530; and/or any of the 8 serines from amino acids 518-531 or HSV-2 ICP0.

Additionally, the mutant HSV-2 having mutant ICP0 with reduced or inhibited phosphorylation can be used in any manner in which the mutant HSV-1 and/or mutant ICP0 can be used. This includes being used in vaccines, diagnostics, cells having the mutant HSV-2 and/or mutant HSV-2 ICP0, and screening assays to find anti-HSV-2 therapeutic agents. Accordingly, the descriptions of mutant HSV-1 and/or mutant ICP0 are equally applicable to a mutant HSV-2 and/or mutant HSV-2 ICP0.

Additionally, the mutant HSV-2 and/or mutant ICP0 can also be included in vaccines, as well as methods of treatment and/or prevention, to reduce or inhibit blephartis (eyelid disease), keratitis (corneal opacity), and latency. Methods of treating and/or preventing blephartis (eyelid disease), keratitis (corneal opacity), genital herpes, and latency can include providing the mutant HSV-2 and/or mutant ICP0 to a subject. The mutant HSV-w and/or mutant ICP0 to a subject can be in the form of a pharmaceutical composition, such as a vaccine. Additionally, a vaccine or other composition can include a combination of mutant HSV-1 and/or mutant HSV-2 and/or mutant ICP0 for a general treatment against all HSV infections or HSV-mediated infections.

EXAMPLES

Example 1

To identify the sites on ICP0 that are phosphorylated, μLC-MS/MS analysis was performed on ICP0 partially purified from HSV-1-infected cells. ICP0 synthesized after removal of CHX block was immunoprecipitated from extracts of $8 \times 10^6$ cells and separated by standard SDS-PAGE. ICP0 was digested with trypsin and chymotrypsin in gel and subjected to μLC-MS/MS analysis. Three phosphorylated regions on ICP0 were identified and designated in regions I, II, and III. Three peptides were identified in region I, four in region II, and seven in region III. Serines and threonines in each phosphorylated region I, II and III, were mutated to alanine to give Phos1, 2, and 3 respectively. Phos 1 is mutated at S224, T226, T231, and T232. Phos 2 is mutated at S365, S367, and S371. Phos 3 is mutated at S508, S514, S517, and T518.

FIG. 1A shows the 775 amino acids of ICP0 and the location of its major functional domains. One region of ICP0 phosphorylation is indicated by bars below its structure. FIG. 1B shows the location of putative phosphorylation sites (4 in total) in region III and probable cellular kinases that target each site. The codon numbers of the putatively phosphorylated serine (S) and threonine (T) residues are listed beneath the peptide sequence in each region. To the right of each S or T are listed the cellular kinases that most likely phosphorylate each residue, as determined by computer-based modeling with NetPhos 2.0, ScanProsite, and MacVector 7.1.1. Kinases include calmodulin kinase II (CaM II), protein kinase A (PKA), cyclin-dependent kinase 1 (cdk-1) and 2, casein kinase I (CKI), casein kinase II (CKII), p70S6K kinase, protein kinase G (PKG), and protein kinase C (PKC). FIG. 1C shows ICP0 phosphorylation site mutant Phos 3 contains mutations. Serines and threonine in this region have been mutated to alanine at S508, S514, S517, and T518.

Mutations in Phos 3 overlap the nuclear localization signal of ICP0 (FIG. 1A), whereas mutations in Phos 1 and Phos 2 are in a large proline-rich region of ICP0 that is important for its transactivating activity (FIG. 1A). Thus, Phos 3 mutations may control the nuclear import and/or accumulation of nuclear ICP0 (Table 1), especially in neurons. Furthermore, Phos 3 replication is sensitive to the effects of interferon-beta in cell culture, which also likely influences its growth in vivo. Mutations in Phos 1 have been shown to impair the E3 Ub ligase, ND10 disrupting, and transactivating activities (Table 1). Mutated residues in Phos 2 differentially affect the staining of ND10-associated proteins (Table 1). Alteration in these activities of ICP0 may well contribute to the in vivo phenotypes observed with Phos 1 and 2.

TABLE 1

Properties of ICP0

| Form of ICP0 | Subcellular Localization | E3 Ub Ligase Activity | Dissociation of ND10 Proteins | Transactivating activity | Impaired Replication virus |
|---|---|---|---|---|---|
| WT ICP0 | Nuclear | Yes | Yes | +++ | No |
| Phos 1 | Nuclear | No | Yes & No | + | Yes & w/IFN |
| Phos 2 | Nuclear | Yes | Yes & No | +++ | No |
| Phos 3 | Nuclear & Cytoplasmic | Yes | Yes | ++ | Only w/IFN |

* IFN = interferon-β

Phosphorylation is a universal post-translational modification that alters the activities of many viral regulatory proteins. The mutation on the phosphorylation sites in ICP0 may decrease ICP0's transactivating activity, and thereby impair or inhibit the replication of HSV-1 and/or the clinical severity of HSV-1-mediated diseases.

Example 2

To determine the effects of these phosphorylation site mutations on acute infection, latency, and reactivation in vivo, mice were ocularly infected with wild-type HSV-1, the Phos mutants, and their marker-rescued counterparts, and viral replication was monitored by plaque assays.

Experimental Design

The purpose of this study is to understand the impact the mutation of Phos 1, 2, and 3 have on HSV-1 acute replication, pathogenesis, latency, and reactivation. The mouse model of HSV-1 latency was used to determine the relative in vivo replication efficiencies for the Phos mutants and their marker-rescuants (MRs) compared to an ICP0 null mutant (7134) and a wild-type strain (KOS). For each viral group, mice were ocularly infected with $1-2\times10^5$ PFU (plaque forming unit) per eye after corneal scarification. On days 1, 3, 5, 7, and 9 post-infection (p.i.), mice from each group were sacrificed, and eye swabs and trigeminal ganglia (TG) were collected. Samples were titered either on Vero or L7 (ICP0-expressing Vero cells) monolayers, and the PFUs/sample were determined. Pathogenicity scores for each viral group were taken on day 9 or 10 p.i. On days 28-30 p.i., TG were removed, cut into 8 pieces, and cocultured on Vero cell monolayers. Media was assayed daily for the presence of infectious virus.

Ocular Replication

Figure 2B:
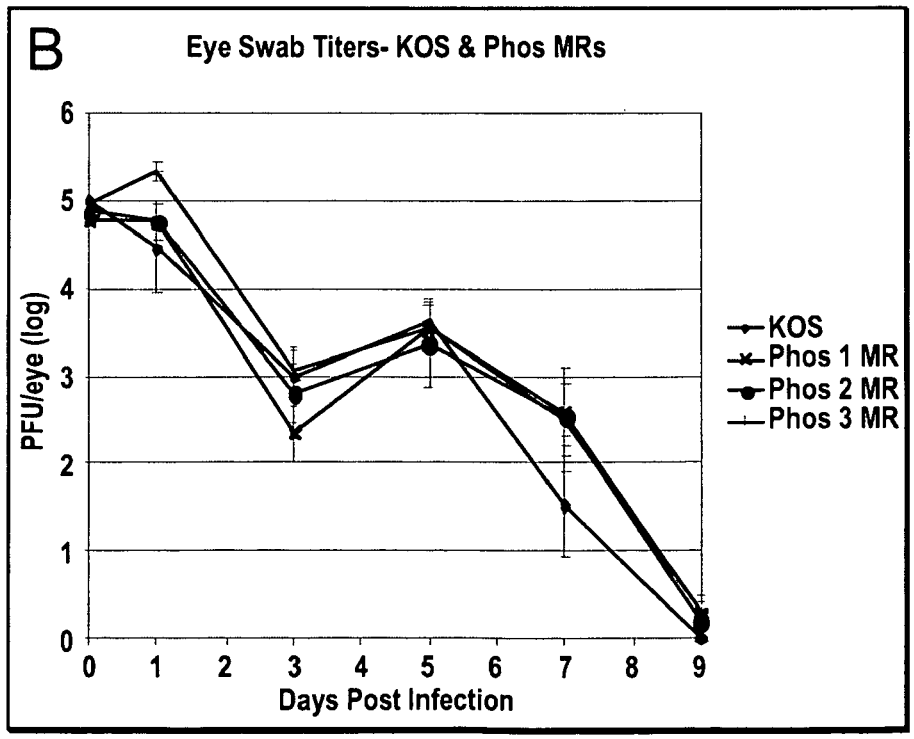

To determine peripheral replication efficiencies of the Phos mutants, acute eye swab samples were taken. KOS and 7134 were included as controls in these studies. FIGS. 2A-2B show eye swab titers of wild-type (KOS), ICP0 null mutant (7134), phosphorylation site mutants (FIG. 2A), and their marker-rescue (MR) viruses (FIG. 2B) during acute infection of mice. For each viral group, seventeen female CD-1 mice were infected in both eyes after corneal scarification. On days 1, 3, 5, 7, and 9 p.i., eyes were swabbed as described in experimental design. KOS and marker-rescue viruses were tittered on Vero cells, and 7134 and the phosphorylation site mutants were tittered on L7 cell monolayers. Results shown are logarithmic means, with the error bars indicating the standard error of the mean. The experiment was performed simultaneously for all groups, but the results are separated for ease of interpretation.

The replication of Phos 1 was slightly reduced relative to KOS on days 1 and 5 p.i., with the greatest difference observed on day 5 (7-fold reduction) (FIG. 2A). The replication of Phos 2 was similar to KOS on all days tested (FIG. 2A). Of all the mutants, Phos 3 showed the greatest reduction in viral replication compared to KOS. Days 1 and 3 showed reduction of approximately 100-fold and 50-fold, respectively. On day 5, no infectious Phos 3 virus was detected (a ~4100-fold decrease), which was followed by a 15-fold reduction on day 7 (FIG. 2A). Notably, the replication of Phos 3 was more impaired than 7134. As expected, the marker-rescuants showed replication that was similar to KOS (FIG. 2B). It was concluded that mutations in Phos 1 and 3 may be required for efficient viral replication in eyes, with Phos 3 showing the greatest impairment of the Phos mutants.

Relative to wild-type virus, eye titers of Phos 1 and 3 were reduced as much as 7- and 4100-fold, respectively, on days 1-9 post-infection. Phos 2 titers were similar to wild-type virus. Thus, Phos 3 may effectively impair HSV-1 peripheral replication.

Trigeminal Ganglia (TG) Replication

Figure 3A:
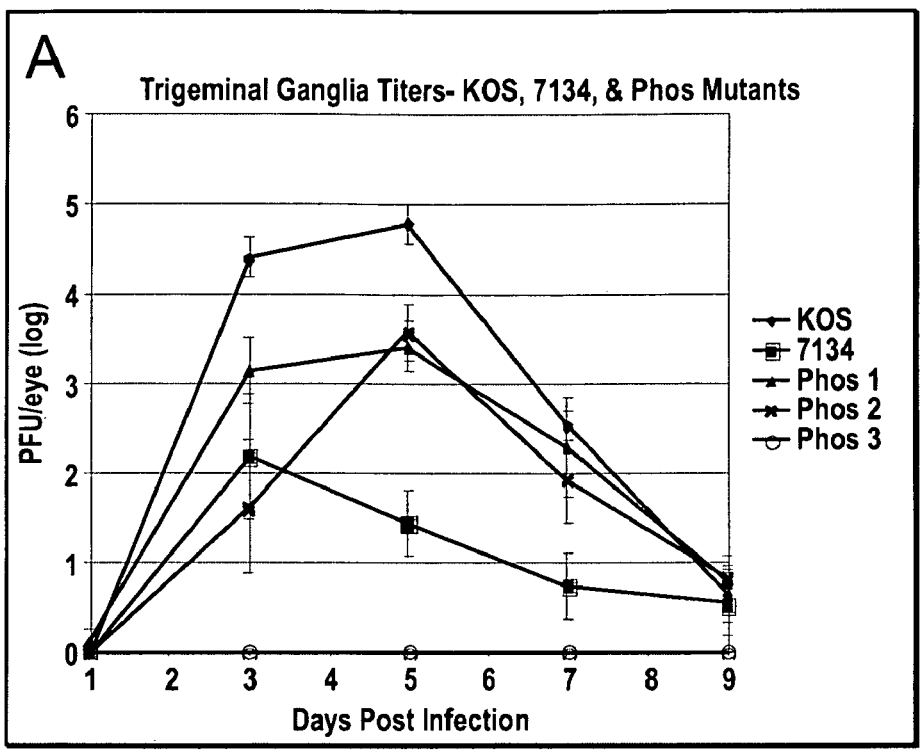
FIGS. 3A-3B include graphs that illustrate trigeminal ganglia (TG) titers of wild-type (KOS), ICP0 null mutant (7134), phosphorylation site mutants (Phos 1, 2, and 3), and their marker-rescue (MR) viruses during acute infection of mice.
Figure 3B:
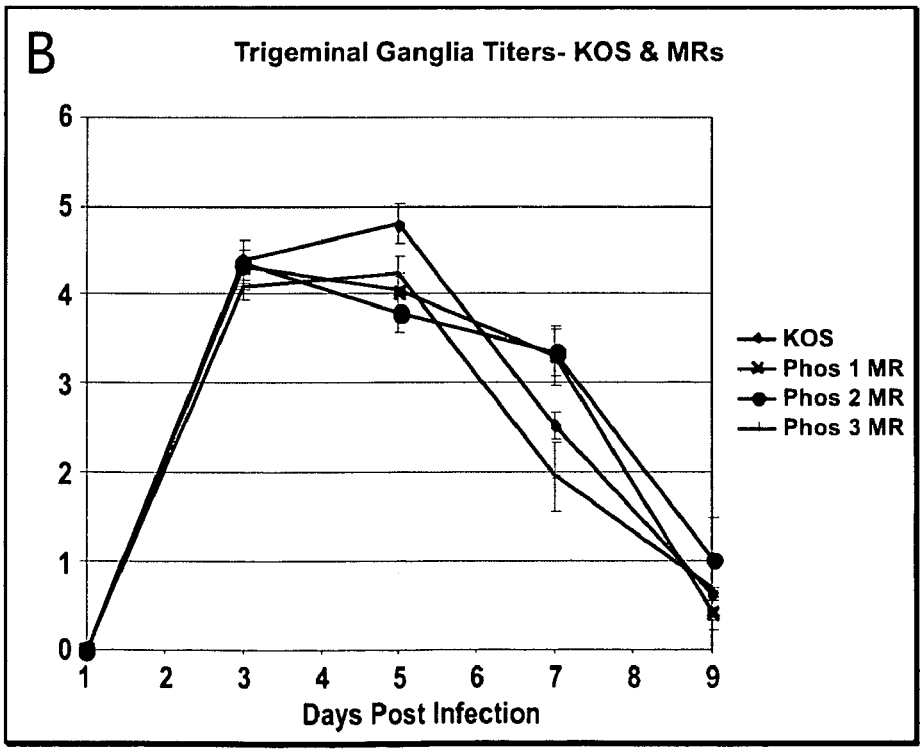

To note differences in viral replication in sensory neurons, TG samples were collected and titered. FIGS. 3A-3B show trigeminal ganglia (TG) titers of wild-type (KOS), ICP0 null mutant (7134), phosphorylation site mutants (FIG. 3A), and their marker-rescue (MR) viruses (FIG. 3B) during acute infection of mice. For each viral group, seventeen female CD-1 mice were infected in both eyes after corneal scarification. On days 1, 3, 5, 7, and 9 p.i., TG were collected and processed as described in experimental design. KOS and marker-rescue viruses were tittered on Vero cells, and 7134 and the phosphorylation site mutants were tittered on L7 cell monolayers. Results shown are logarithmic means, with the error bars indicating the standard error of the mean. The experiment was performed simultaneously for all groups, but the results are separated for ease of interpretation.

TG titers showed similar trends to the eye swab titers. On days 3 and 5 p.i., Phos 1 replication was diminished 20- and 25-fold, respectively (FIG. 3A). For Phos 2, viral titers were reduced 615-fold (day 3 p.i.) and 20-fold (day 5 p.i.) (FIG. 3A). Remarkably, no Phos 3 infectious virus was detected in TG during the course of infection, unlike the ICP0 null mutant 7134 (FIG. 3A). Marker-rescue viruses replicated at levels comparable to KOS (FIG. 3B). The results indicate that Phos 1 and Phos 2 mutations impaired acute viral replication in the TG, whereas Phos 3 mutations completely inhibited viral replication.

Trigeminal ganglia (TG) titers of Phos 1 and 2 were reduced as much as 25- and 615-fold, respectively, on days 1-9 post-infection, whereas no infectious virus was detected in acute TG of Phos 3-infected mice. Thus, Phos 3 may effectively impair HSV-1 replication in sensory neurons.

Pathogenesis

Figure 4:
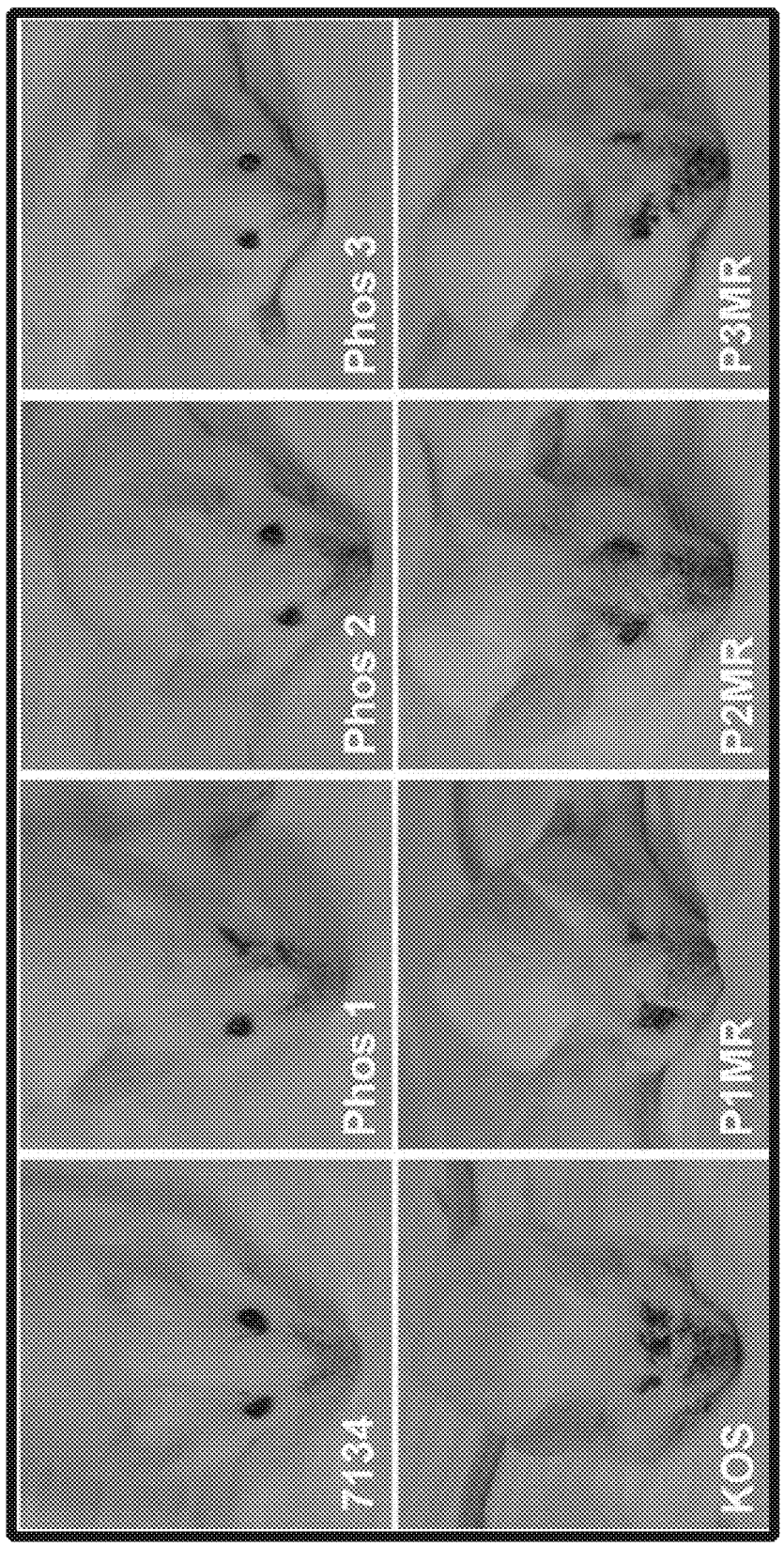
FIG. 4 includes images of infected mice (9 days p.i.) of wild-type (KOS), ICP0 null mutant (7134), phosphorylation site mutants (Phos 1, 2, and 3), and their marker-rescue (MR) viruses.

To establish whether acute replication altered viral pathogenesis, clinical pathology scores were taken on either day 9 or 10 p.i. The physiological severity of infection was ranked on a scale of 0-4 for each viral group, where a score of zero indicates no apparent infection, and a score of 4 indicates complete removal of the hair from between the eyes due to scratching. FIG. 4 shows various images of infected mice (9 days p.i.) of wild-type (KOS), ICP0-null mutant (7134), phosphorylation site mutants, and their marker-rescue (MR) viruses. For each group, mice were infected in both eyes with virus after corneal scarification.

Table 2 shows average pathogenicity scores of wild-type (KOS), ICP0-null mutant (7134), phosphorylation site mutants, and their marker-rescue (MR) viruses. For each group, mice were infected in both eyes with virus after corneal scarification.

Two of the three Phos mutants showed reduced pathogenicity on days 9 and 10 p.i. (FIG. 4 and Table 2). Notably, Phos 3-infected mice displayed no signs of disease, similar to 7134 (FIG. 4 and Table 2). Marker-rescue viruses had pathologies comparable to or slightly greater than KOS (FIG. 4 and Table 2). Thus, Phos 3 may effectively treat, limit or prevent HSV-1 infection.

In Table 2, average pathogenicity scores of wild-type (KOS), ICP0-null mutant (7134), phosphorylation site mutants, and their marker-rescue (MR) viruses.

indicate that after day 11, samples were heat shocked at 43° C. for 3 h. For each viral group, mice were infected in both eyes after corneal scarification. On day 28-30 p.i., TGs were collected as described in experimental design. Culture medium was assayed daily for the presence of infectious virus. Each time point represents the cumulative percentage of reactivating samples. The figure shows two independent experiments.

Figure 5A:
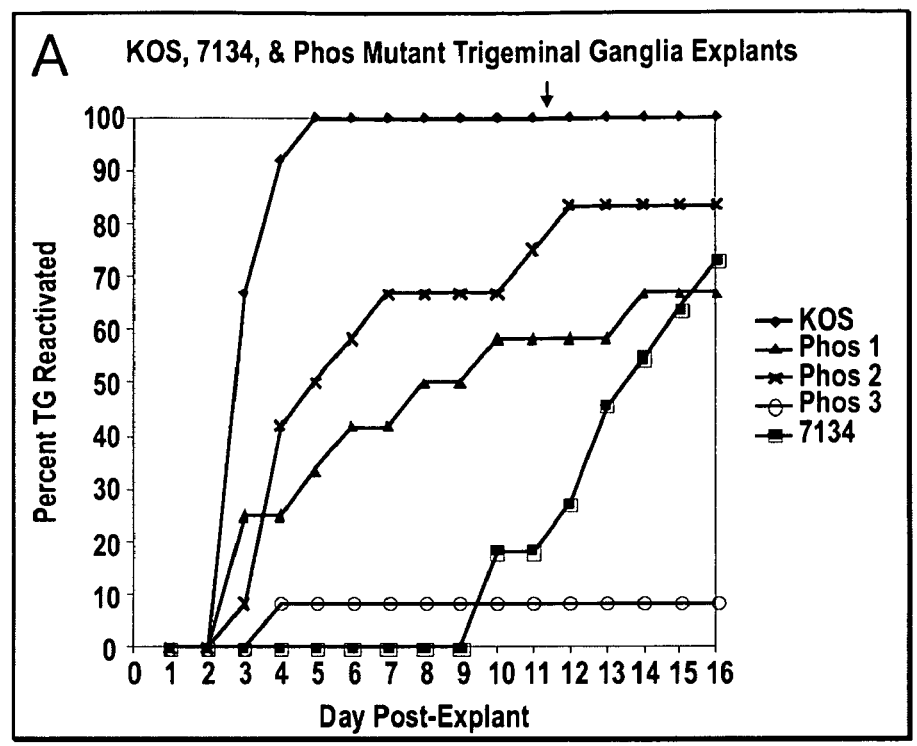
FIGS. 5A-5B include graphs that illustrate reactivation efficiency of wild-type (KOS), ICP0-nul mutant (7134), phosphorylation site mutants (Phos 1, 2, and 3), and their marker-rescue (MR) viruses from TG explants.
Figure 5B:
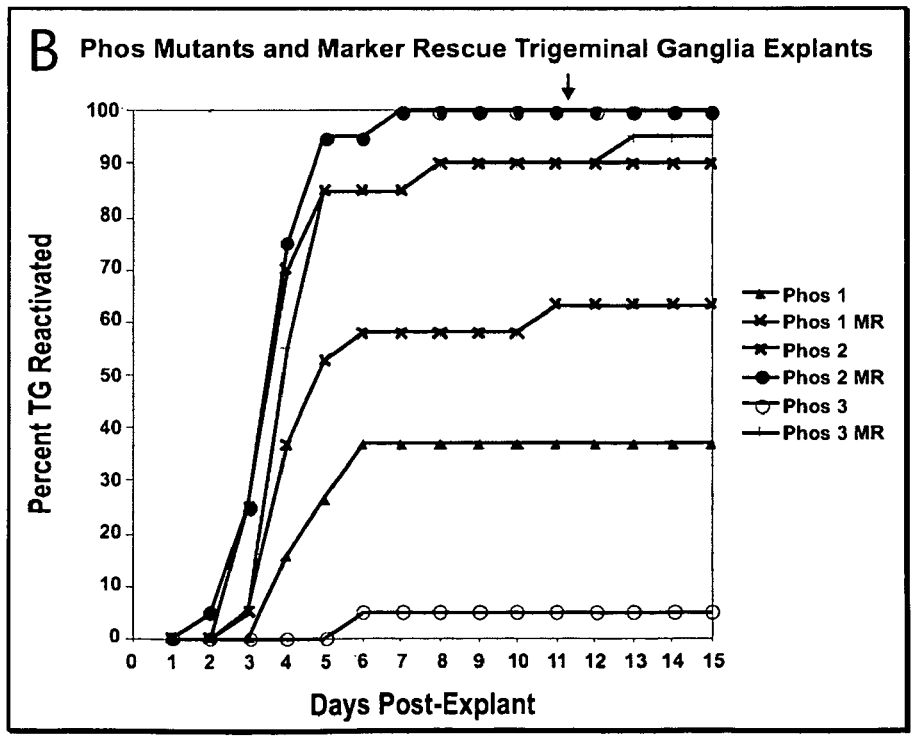

In the initial study, rates of reactivation of the Phos mutants were compared to KOS and 7134. KOS began to reactivate on day 3 post-explant (p.e.) at 66% and reached 100% reactivation by day 5 p.e. (FIG. 5A). Phos 1 and 2 showed steady reactivation throughout the study, achieving 66% and 83%, on days 14 p.e. and 12 p.e., respectively (FIG. 5A). Phos 3 reactivation peaked at day 4 p.e., maintaining a reactivation efficiency of 8% (FIG. 5A). 7134 started to reactivate on day 10 p.e., reaching its highest levels (73%) on day 16 p.e. (FIG. 5A). In a second study, the reactivation efficiencies of the Phos mutants relative to their rescuants were examined. The marker-rescue viruses behaved as expected, rapidly reactivating from days 2-5 p.e., eventually reaching efficiencies of 85-95% by day 5 p.e. (FIG. 5B). In contrast, Phos 1 reached a peak efficiency of 37% by day 6 p.e.; Phos 2 was at 58% by day 6 p.e., reaching a peak of 63% by day 11 p.e.; and Phos 3 reactivated at 5% on day 6 p.e., and remained so through day 15 p.e. (FIG. 5B). These reactivation studies showed that the frequencies and kinetics of reactivation were altered for the Phos mutants, with Phos 3 showing the greatest deficiency, followed by Phos 1, and finally Phos 2. Thus, Phos 3 may effectively impair or prevent HSV reactivation.

Discussion

In this study, it is shown that three ICP0 phosphorylation site mutants are impaired for replication and reactivation in vivo. Of the viral mutants tested, mutations in Phos 3 had the greatest effect on all phases of the HSV-1 life-cycle that were examined in vivo. In contrast to the ICP0 null mutant 7134, Phos 3 did not replicate in neurons of the TG during acute infection on days 1-9 p.i. Thus, the sites mutated in Phos 3 are required for replication in TG during the initial stage of HSV-1 infection. This inhibition resulted in no visible signs of viral pathogenesis and an impaired reactivation phenotype. Phos 1 also affected viral replication and pathogenesis, although its defects were not as pronounced as those of Phos 3. Phos 2 was the least attenuated mutant of the three viruses tested. Notably, mutations in Phos 2 did not affect ocular

TABLE 2

|  | KOS | 7134 | Phos 1 | Phos 1 MR | Phos 2 | Phos 2 MR | Phos 3 | Phos 3 MR | Sample size per group |
|---|---|---|---|---|---|---|---|---|---|
| Expt 1 t = 9 d.p.i. | $2.67 \pm 0.41^a$ | $0.2 \pm 0.22$ | $1.2 \pm 0.42$ | $2.25 \pm 0.55$ | $1 \pm 0$ | $2.67 \pm 0.41$ | $0 \pm 0$ | $2.5 \pm 0.33$ | n = 3-5 |
| Expt 2 t = 10 d.p.i. | $1.38 \pm 0.50$ | N.D. | $0.6 \pm 0.18$ | $2.16 \pm 0.26$ | $1 \pm 0.53$ | $2.25 \pm 0.37$ | $0 \pm 0$ | $1.31 \pm 0.21$ | n = 13-16 |

Reactivation

To ascertain the efficiencies of reactivation of the viral groups, explant co-cultivations on latently infected TG (28-30 days p.i.) were performed. FIGS. 5A-5B show reactivation efficiencies of wild-type (KOS), ICP0-null mutant (7134), phosphorylation site mutants, and their marker-rescue (MR) viruses from TG explants. (A) KOS, 7134, and phosphorylation site mutants, and (B) phosphorylation site mutants and marker-rescue viruses. The arrows at the top of both graphs replication. Thus, the phosphorylation sites in Phos 2 may not be necessary to ICP0 function and HSV-1 replication in eyes.

Previous reports have shown that the level of acute replication in neurons directly influences the establishment of and reactivation from latency. Because the Phos mutants show reduced reactivation and ICP0 is important for establishing an efficient latent infection, it is plausible that the Phos mutants may not have established latency at sufficient levels. This possibility is currently being tested. For all three phosphorylation site mutant viruses, inclusion of the marker-rescue viruses confirmed that the phenotypes observed with the Phos mutants are due to the phosphorylation site mutations and not from secondary mutations present in the viral genome. Taken together, these data strongly support a model in which ICP0 phosphorylation may be essential for efficient HSV-1 replication in vivo.

Summary

Phos 1 mutations impair acute replication in eyes and TG, and reactivation from latency. Phos 2 mutations impair acute replication in TG and reactivation from latency. Phos 3 mutations impair ocular replication, completely inhibit acute TG replication, and significantly reduce reactivation. Phos 3 shows the greatest diminution of the three mutant viruses. Mutations in Phos 3 overlap the nuclear localization signal of ICP0, whereas mutations in Phos 1 and Phos 2 are in a large proline-rich region of ICP0 that is important for its transactivating activity. Thus, Phos 3 mutations may control the nuclear import and/or accumulation of nuclear ICP0 (Table 1), especially in neurons.

All three ICP0 phosphorylation regions may be required for efficient viral replication and reactivation from latency. However, the Phos 3 mutant form of ICP0 appears to interfere with a viral or cellular function essential for viral growth in neurons. Furthermore, Phos 3 replication is sensitive to the effects of interferon-beta in cell culture, which also likely influences its growth in vivo. Mutations in Phos 1 have been shown to impair the E3 Ub ligase, ND10 disrupting, and transactivating activities (Table 1). Mutated residues in Phos 2 differentially affect the staining of ND10-associated proteins (Table 1). Alteration in these activities of ICP0 may well contribute to the in vivo phenotypes observed with Phos 1 and 2.

Example 3

Experimental Design

To assess relative capacity to replicate in neural tissue, groups of 4 mice were inoculated by the intracranial (i.c.) route with $1 \times 10^3$ PFU of virus. Brain tissue was removed after 24 hr, homogenized, and viral titer was determined on L7 cells. ICP0 helps HSV-1 to counteract the host type I IFN response. On the theory that Phos3 is attenuated for replication in neural tissue because its mutant ICP0 cannot block the type I IFN response, mice deficient in the type I IFN receptor were similarly inoculated with 7134, Phos3, Phos3MR, or KOS.

The mouse model of prophylactic vaccination against HSV-1 corneal challenge was used to determine the in vivo efficacy of Phos3 relative to a replication-competent ICP0 null mutant (7134) and a replication-defective mutant (1D461) in generating immune responses that protect against ocular disease caused by HSV-1.

The 1D461 control is an engineered mutant virus derived from the HSV-1 KOS strain. It has been manipulated in three ways with the goal of making an optimally safe and effective live vaccine. First, it is replication-defective due to a deletion in the UL29 gene encoding ICP8, a viral protein essential for replication of the viral DNA. Second, this virus also contains a deletion in the UL41 gene encoding the virion host shutoff protein. Vhs is known to help HSV-1 counteract the host immune response, and its deletion improves the immunogenicity and protective capacity of an ICP8 replication-defective virus. Third, we have inserted the mouse CD86 gene encoding B7-2 co-stimulation molecules into the thymidine kinase locus. B7-2 is a second signal that, along with the first signal provided by viral antigen presented on MHC molecules, stimulates naïve T cells to orchestrate an antiviral immune response (or vaccine-induced immunity). Thus, 1D461 cannot replicate and spread in a vaccine (hence optimal safety), and yet produces numerous other virus proteins and host co-stimulation molecules (to stimulate antiviral immunity), and has an important viral inhibitor of immune responses disabled (hence increasing its immunogenicity).

For each viral group, 10 mice were immunized subcutaneously in the hind flanks with $5 \times 10^5$ PFU (high dose), $1 \times 10^5$ PFU (medium dose) or $2 \times 10^4$ PFU (low dose) of Phos3, 7134, or 1D461. An amount of supernatant from uninfected cells (control supernatant) equivalent to the high dose concentration was a negative control. On day 21 after immunization, mice were bled and serum was used to determine HSV-specific antibody titers by ELISA. On day 30 after immunization, mice were infected with $4 \times 10^5$ PFU per eye HSV-1 strain mP after corneal scarification. On days 0.2, 1, 2, 3, and 4 post-challenge (p.c.), the eyes of mice were swabbed for determination of virus titer shed in the tear film. Mice were individually weighed and scored for blepharitis in masked fashion on days 0 through 12 p.c. Keratitis was assessed on days 9 and 14 p.c. in masked fashion. On days 28-29 p.c. TG were removed and frozen for determination of viral genome load by real-time PCR.

Replication in Brain

Figure 6:
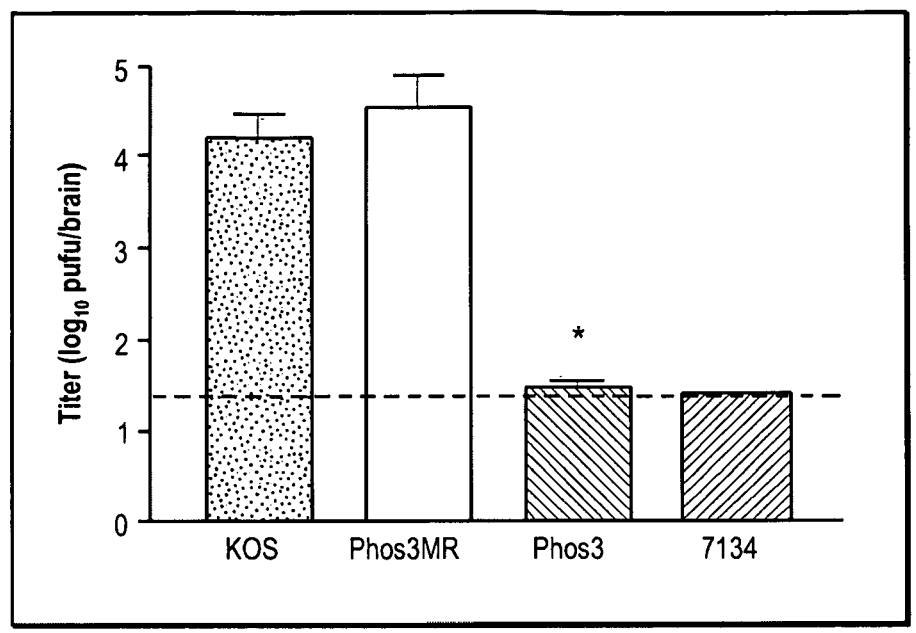
FIG. 6 includes a graph that illustrates replication of virus in the brains after direct inoculation by wild-type (KOS), ICP0-nul mutant (7134), phosphorylation site mutant (Phos 3), and it marker-rescue (MR) virus.

To determine capacity of Phos3 to replicate in the nervous system, mouse brain tissue was taken after direct i.c. inoculation of virus. 7134, Phos3MR and wild-type KOS were included as controls in these studies. FIG. 6 shows replication of virus in the brain after direct inoculation. Groups of 4 mice lacking the type I IFN receptor were inoculated i.c. with $1 \times 10^3$ PFU of the indicated virus. After 24 hours the brain tissue was removed and virus titer was determined by standard plaque assay. Neither Phos3 nor 7134 could be detected in the brain tissue of wild-type mice 24 hr after infection.

Phos 3 and 7134 were rarely detected even in brain tissue of mice that lacked the type I IFN receptor (FIG. 6), in contrast to the robust replication of KOS and Phos3MR. This result provides strong evidence that Phos3 is defective for replication in the nervous system. It was determined that phosphorylations at region III are important for efficient replication of HSV-1 in neural tissue. This is surprising because Phos3 may impair or prohibit replication of HSV-1 in nervous system.

Antibody Titers

Figure 7:
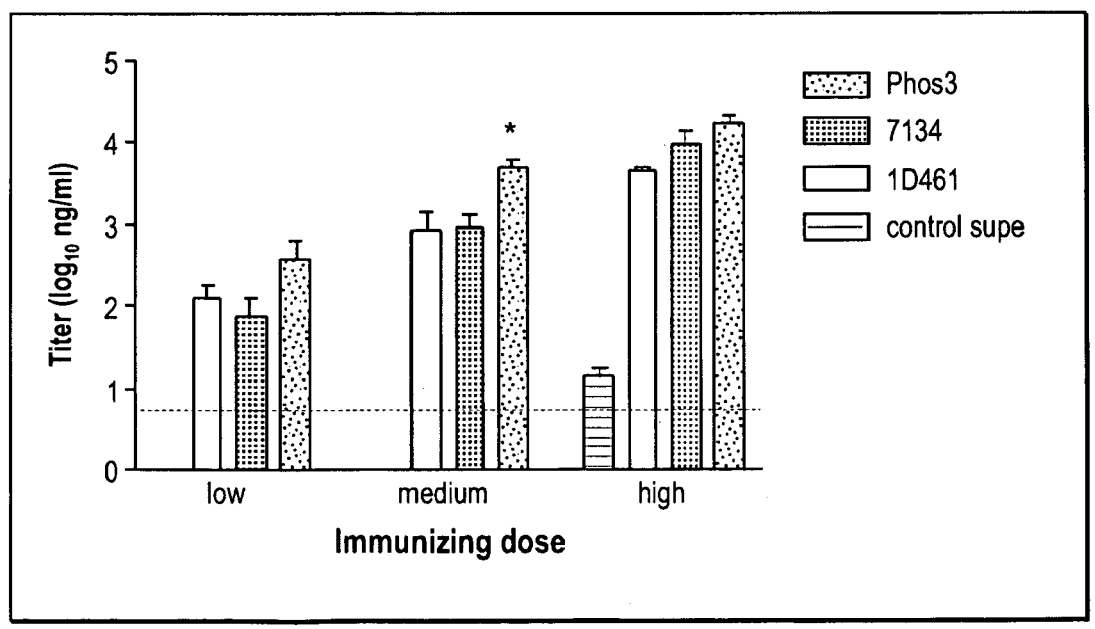
FIG. 7 includes a graph that illustrates titer of HSV-specific antibody in mice after immunized with ICP0-null mutant (7134), phosphorylation site mutant (Phos 3), control virus (1D416), and control supernant.

To determine whether Phos3 can stimulate a strong immune response, mice were immunized with Phos3. 7134 and 1D16 viruses were replication-competent and -defective controls, respectively. FIG. 7 shows titer of HSV-specific antibody in immunized mice. Groups of 6 mice were immunized with high, medium or low doses of the indicated viruses and 1 group of 6 mice was immunized with control supernatant as a negative control. Blood was collected on 21 d post-immunization and HSV-specific serum IgG was quantified by ELISA. Phos3 induced a stronger HSV-specific antibody response than 7134 or 1D461 at all immunizing doses, particularly at the medium dose (FIG. 7).

It was concluded that Phos3 is immunogenic, and Phos3 stimulates a stronger immune response than the less attenuated ICP0 null virus. Thus, Phos3 surprisingly may be more effective in impairing or preventing HSV-1 infection than the ICP0 null virus.

Protection from HSV-1 Corneal Infection and Disease

To determine how effectively immunization with Phos3 could protect mice from ocular HSV-1 infection, corneal challenge was perform. After corneal scarification mice were infected with a virulent strain of HSV-1.

Body Weight Change

Figure 8A:
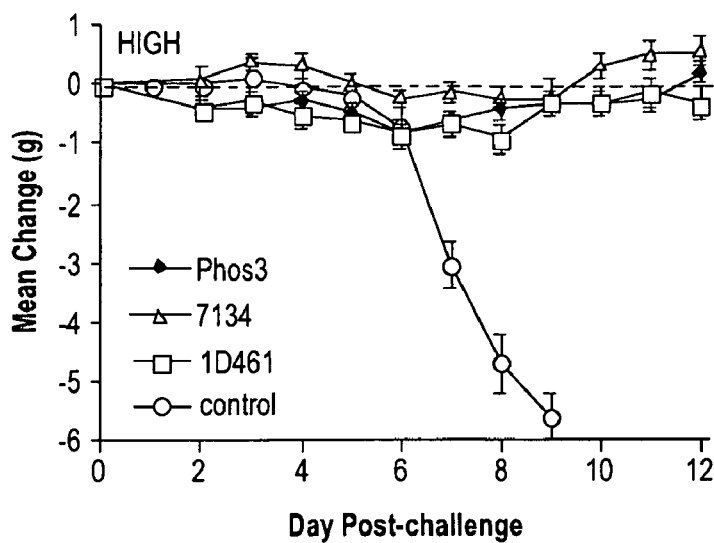
FIGS. 8A-8C include graphs that illustrate body weight of immunized mice after corneal challenge with HSV-1 when the mice were immunized with high (FIG. 8A), medium (FIG. 8B), or low (FIG. 8C) doses of ICP0-null mutant (7134), phosphorylation site mutant (Phos 3), 1D416, and control supernatant FIGS. 9A-9C include graphs that illustrate protection of mice from blepharitis after corneal challenge with HSV-1 when the mice were immunized with high (FIG. 9A), medium (FIG. 9B), or low (FIG. 9C) doses of ICP0-null mutant (7134), phosphorylation site mutant (Phos 3), 1D416, and control supernatant.
Figure 8B:
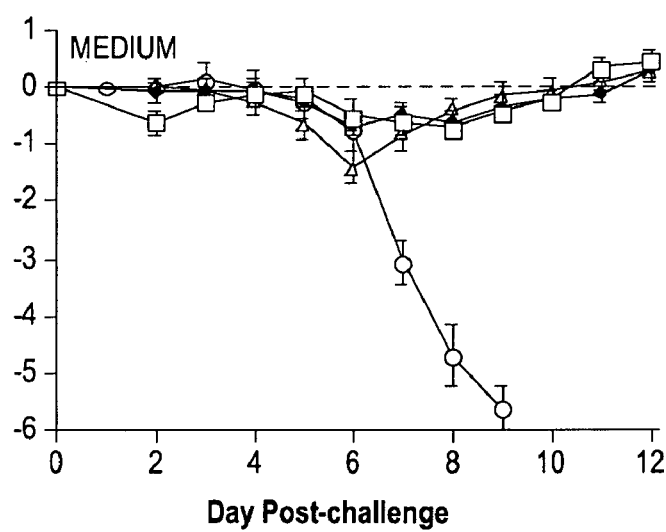
Figure 8C:
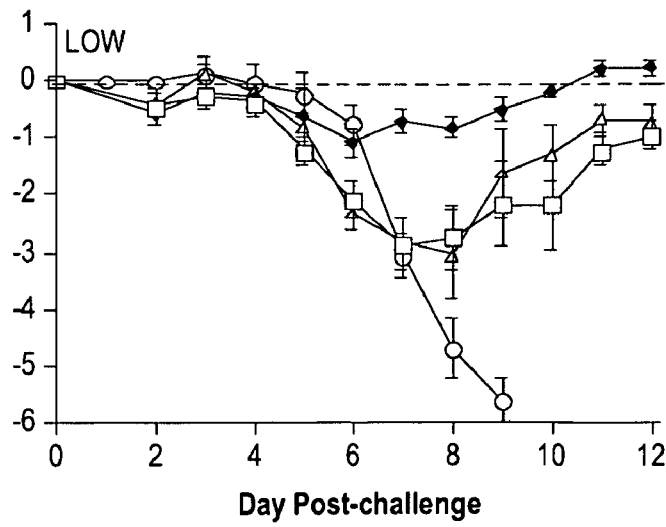

To determine how well the general health of mice is preserved after challenge, the mice were weighed daily for two weeks. FIG. 8 shows body weight change of immunized mice after corneal challenge with HSV-1. Groups of 10 mice immunized with high, medium or low doses of the indicated viruses and 1 group of mice immunized with control supernatant were challenged by corneal infection with HSV-1 and monitored daily for change in weight. Previous immunization with any dose of Phos3 allowed the mice to maintain body weight (FIG. 8), whereas mice immunized with the low dose of 7134 or replication-defective virus lost an average of 3 grams (approximately 15% of their body weight). Thus, compared to 7134 and replication-defective virus, Phos3 vaccine may preserve the general health of immunized subjects.

Protection from Eyelid Swelling and Disease (Blepharitis)

Figure 9A:
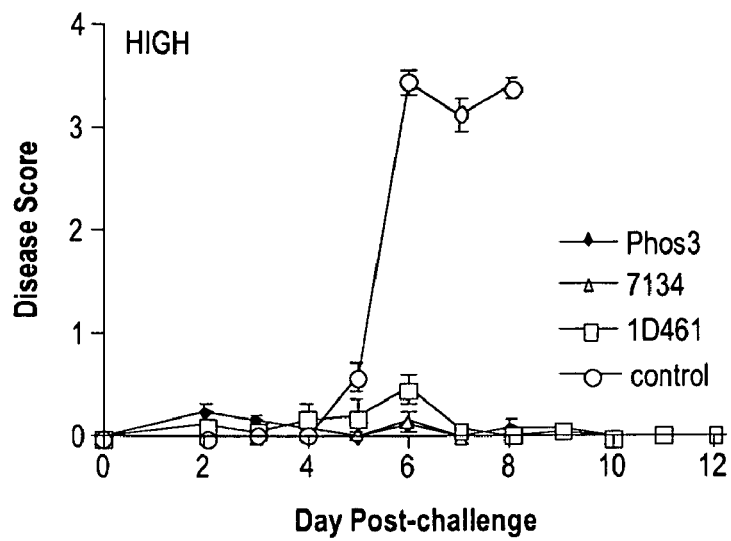
Figure 9B:
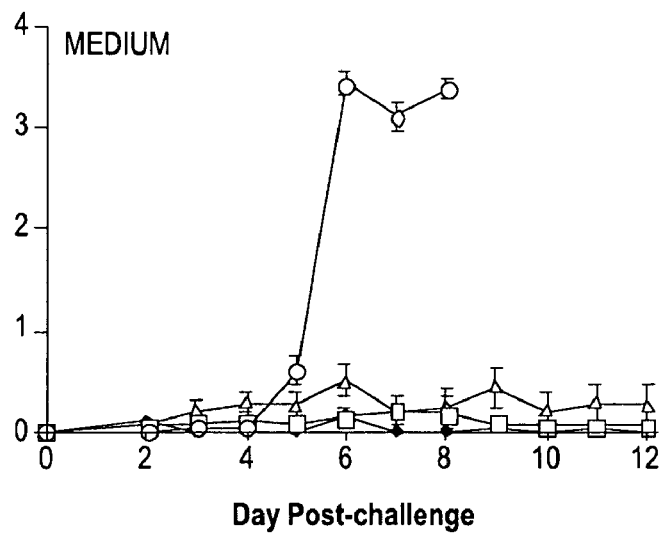
Figure 9C:
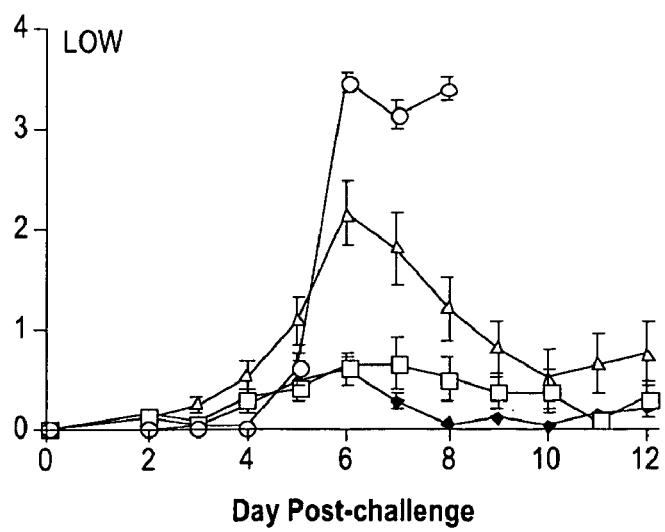

To determine how well previously immunized mice are protected from eyelid swelling and disease (blepharitis) after challenge, blepharitis was scored for each eye using a scale of 1 to 4. Scoring was performed by an observer masked to the experimental groups. Experiments were performed as described in experimental design. FIG. 9 shows protection of mice from blepharitis after corneal challenge. Groups of 10 mice immunized with high, medium or low doses of the indicated viruses and 1 group of mice immunized with control supernatant were challenged by corneal infection with HSV-1 and scored daily for signs of eyelid disease.

Phos3 almost completely protected mice from developing blepharitis when given at the high or medium doses (FIG. 9). Mice immunized with the lowest dose of Phos3 developed only mild and transient swelling of the eyelid. In contrast, mild swelling was prolonged in mice immunized with the replication-defective control virus, and blepharitis was much more severe in mice previously immunized with 7134. Thus, Phos3 may effectively impair or prevent subjects from eyelid swelling and diseases.

Protection from Opacification of the Cornea (Keratitis)

Figure 10A:
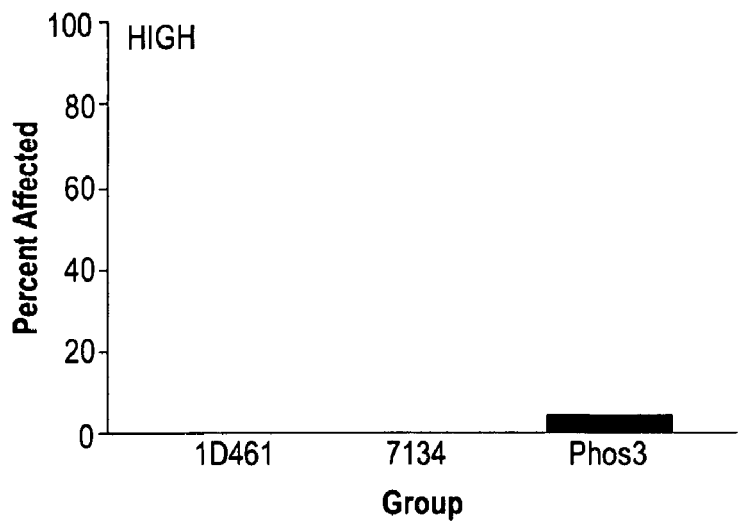
FIGS. 10A-10C include graphs that illustrate protection of mice from severe keratitis after corneal challenge with HSV-1 when the mice were immunized with high (FIG. 10A), medium (FIG. 10B), or low (FIG. 10C) doses of ICP0-null mutant (7134), phosphorylation site mutant (Phos 3) and 1D416
Figure 10B:
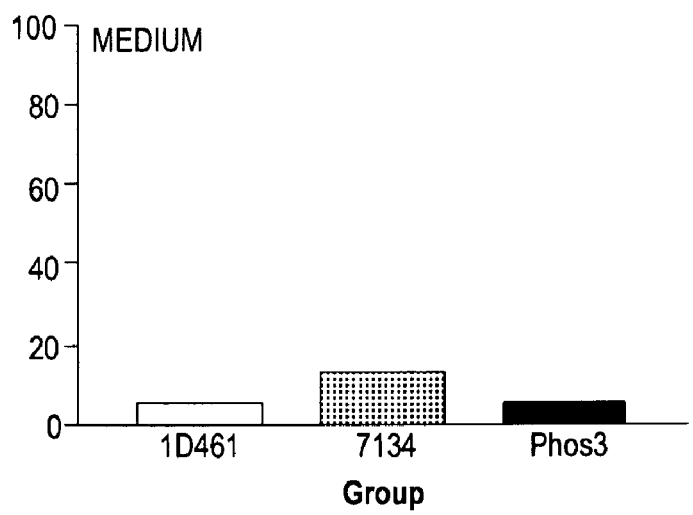
Figure 10C:
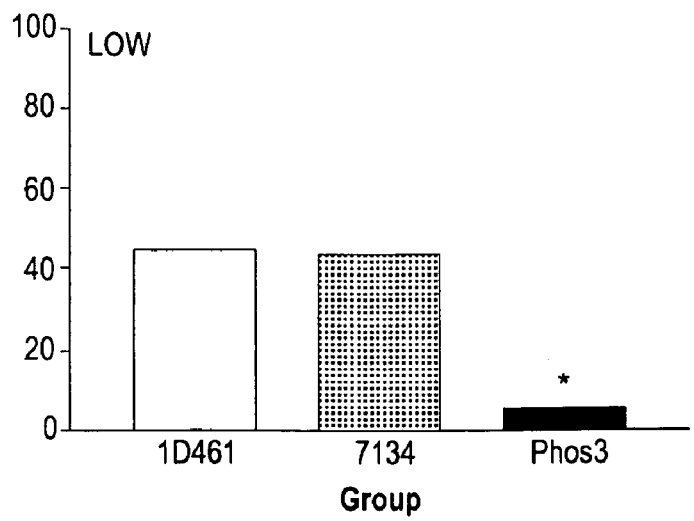

Keratitis, or opacification of the cornea, was evaluated in all immunization groups after challenge (except those receiving control supernatant, which did not survive). FIG. 10 shows Protection of mice from severe keratitis after corneal challenge. Groups of 10 mice immunized with high, medium or low doses of the indicated viruses and 1 group of mice immunized with control supernatant were challenged by corneal infection with HSV-1. At 14 days after challenge the eyes were examined for signs of severe keratitis. Values represent the percentage of eyes from surviving mice with a score of 3 or 4 (sight-impairing). All immunizing viruses significantly protected mice when given at the high or medium doses, but only Phos3 continued to protect the majority of eyes from severe (sight impairing) keratitis at the low immunizing dose (FIG. 10). Thus, Phos3 may effectively impair or prevent subjects from opacification of the cornea.

Protection from Lethal Infection

Figure 11:
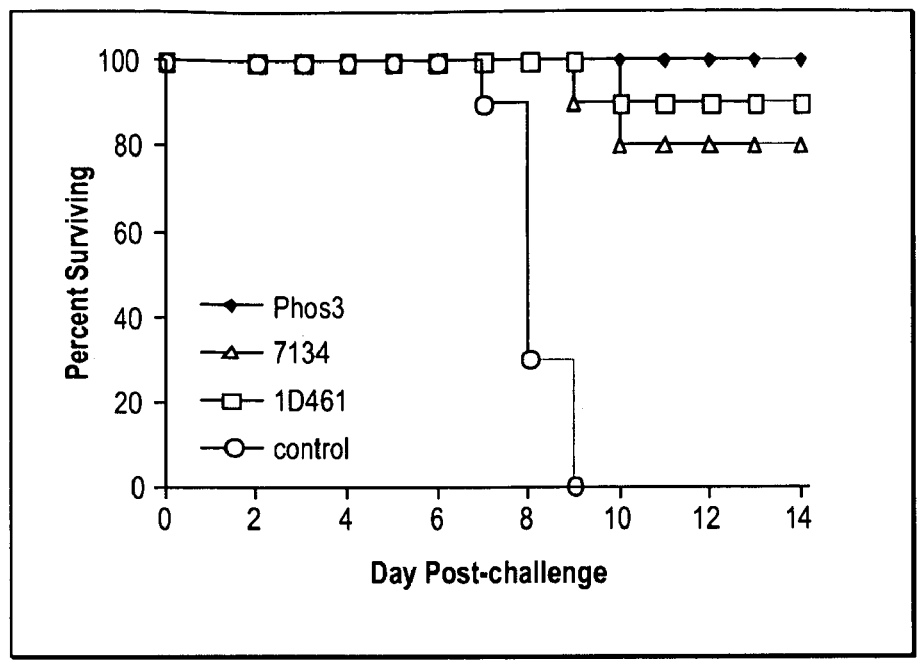
FIG. 11 includes a graph that illustrates survival of mice after corneal challenge with HSV-1 when the mice were immunized with low dose of ICP0-null mutant (7134), phosphorylation site mutants (Phos 3), 1D416, and control supernatant.

To determine whether immunization could protect mice from lethal infection, survival was monitored over time post-challenge. FIG. 11 shows survival of mice after corneal challenge. Groups of 10 mice immunized with the low dose of the indicated virus were challenged on the scarified corneas with HSV-1, and their survival was monitored daily. All mice immunized with control supernatant succumbed by day 9 post-challenge (FIG. 11). Deaths also occurred after challenge in groups immunized with the low dose of 7134 or replication-defective control virus, but all mice immunized with Phos3 survived. Thus, Phos3 may effectively protect subjects from lethal infection.

Summary

Collectively, the results of corneal challenge of immunized mice indicate that prior vaccination with Phos3 provides significant protection against HSV-1-mediated disease of the eyelid and eye, even at a very low immunizing dose. Surprisingly, this protective effect was stronger for Phos3 than either a less attenuated ICP0 null virus or a replication-defective control virus.

Example 4

Virus Titers in the Tear Film of Immunized Mice for 30 Days during the Period of Acute Replication after Corneal Challenge.

Female 6-week-old BALB/c mice (National Cancer Institute) were immunized with $4\times10^4$, $2\times10^5$, or $1\times10^6$ PFU of each virus or control cell extract, in a 20 µL volume subcutaneously near the base of the tail, using a 26-gauge needle. Four weeks after primary immunization, all mice were challenged by inoculation of $4\times10^5$ PFU of HSV-1 strain mP per eye after corneal scarification in inoculum of 5 µL. This dose produces encephalitis in 100% of non-immune BALB/c mice and represents 10 to 30 times the minimum dose. Results shown are for mice immunized with Phos 3, 7134 (ICP0 null mutant), 1D461 (control virus), and control supernatant (cell extract). Description for methods was modified as previously described. Immunization with replication-defective mutants of herpes simplex virus type 1: sites of immune intervention in pathogenesis of challenge virus infection. Morrison L A, Knipe D M. J Virol. 1994 February; 68(2):689-96.)

Mice immunized at the high dose ($1\times10^6$ PFU) of Phos 3 and 7134 had lower titers of virus in eye swabs on days 1-4 after challenge; 1D461 had lower titers on days 2-4 post challenge compared to the control supernatant. At the medium dose ($2\times10^5$ PFU), Phos 3, 7134, and 1D461 had lower titers 1-4 post challenge compared to the control supernatant. At the low dose ($4\times10^4$ PFU), 1D461 titers were lower on days 1-4 post challenge compared, whereas Phos 3 and 7134 titers were lower on 2-4 days post challenge relative to the control supernatant. Notably, immunization with Phos 3 significantly decreased shedding of virus on either day 3 (high dose) or day 4 (medium and low doses) compared to all other viral groups during primary replication. Thus, Phos3 vaccine may impair or prevent HSV-1 replication or infection in eyes.

Figure 12A:
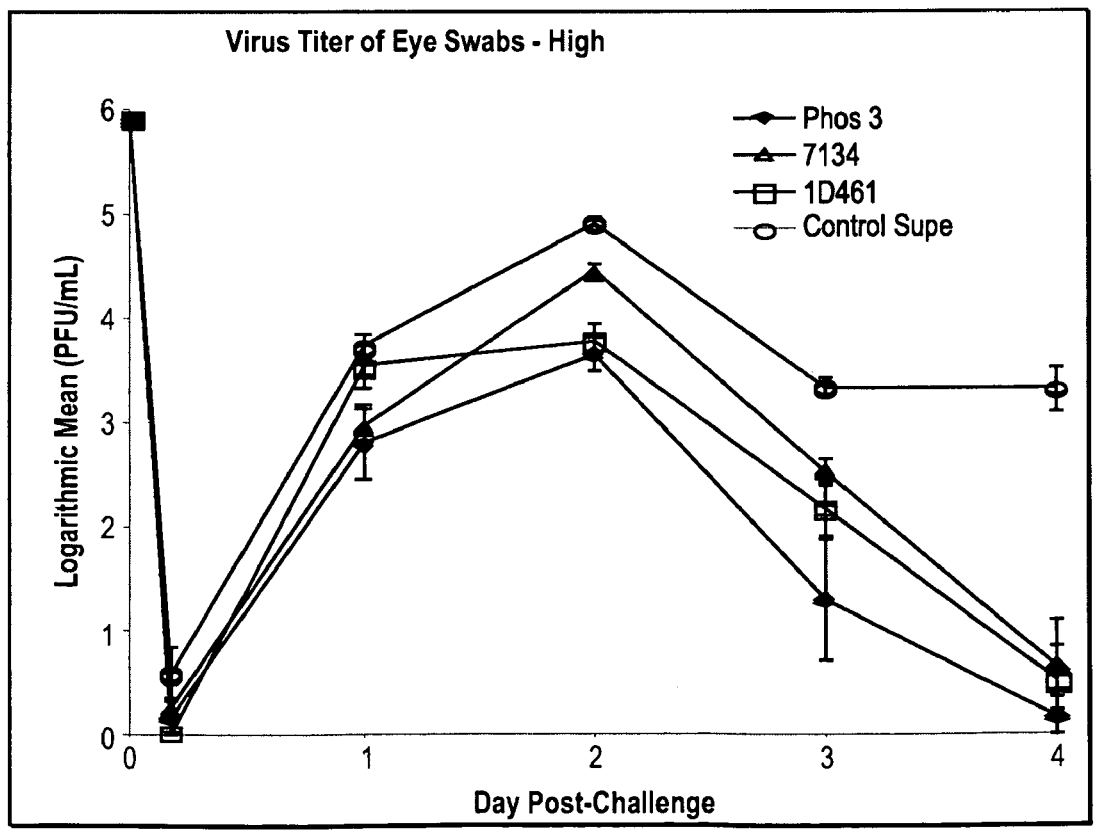
FIGS. 12A-12C include graphs that illustrate viral titer of eye swabs after corneal challenge with HSV-1 when the mice were immunized with high (FIG. 12A), medium (FIG. 12B), or low (FIG. 12C) doses of ICP0-null mutant (7134), phosphorylation site mutant (Phos 3), control virus (1D416), and cell extract (control supernatant).
Figure 12B:
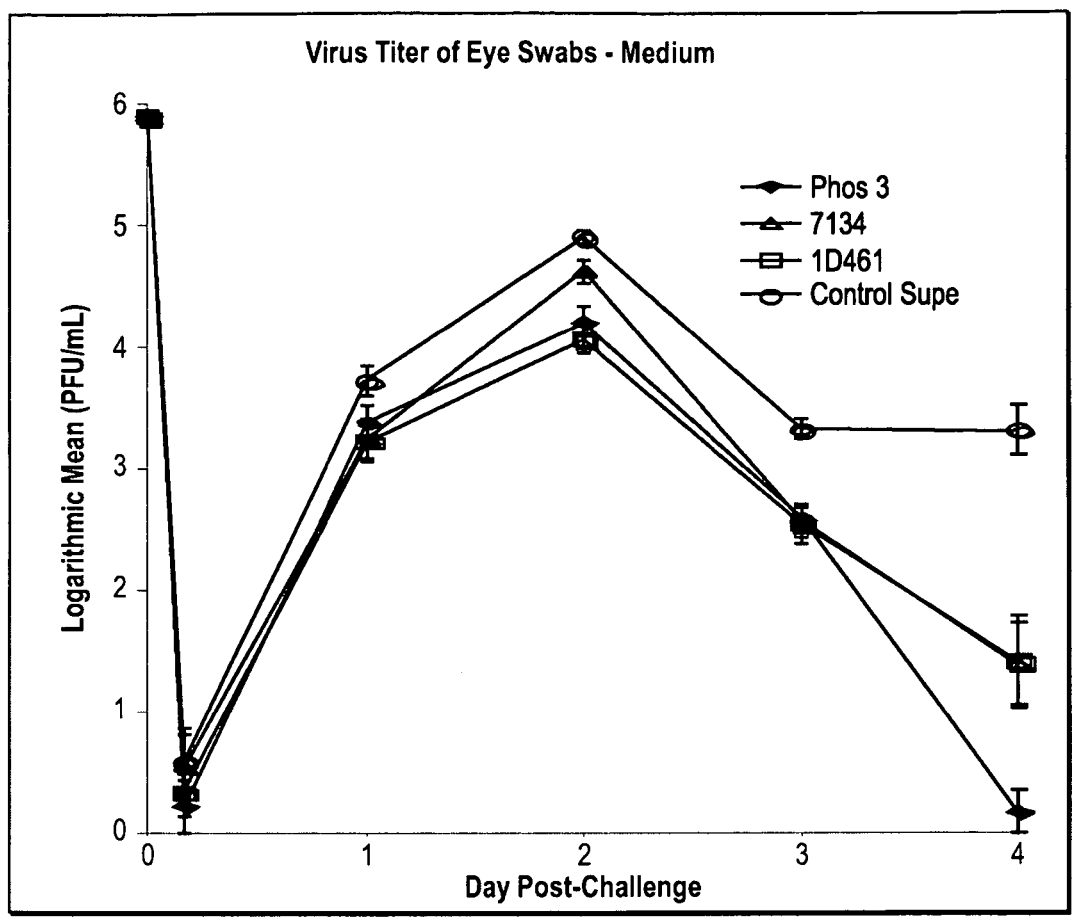
Figure 12C:
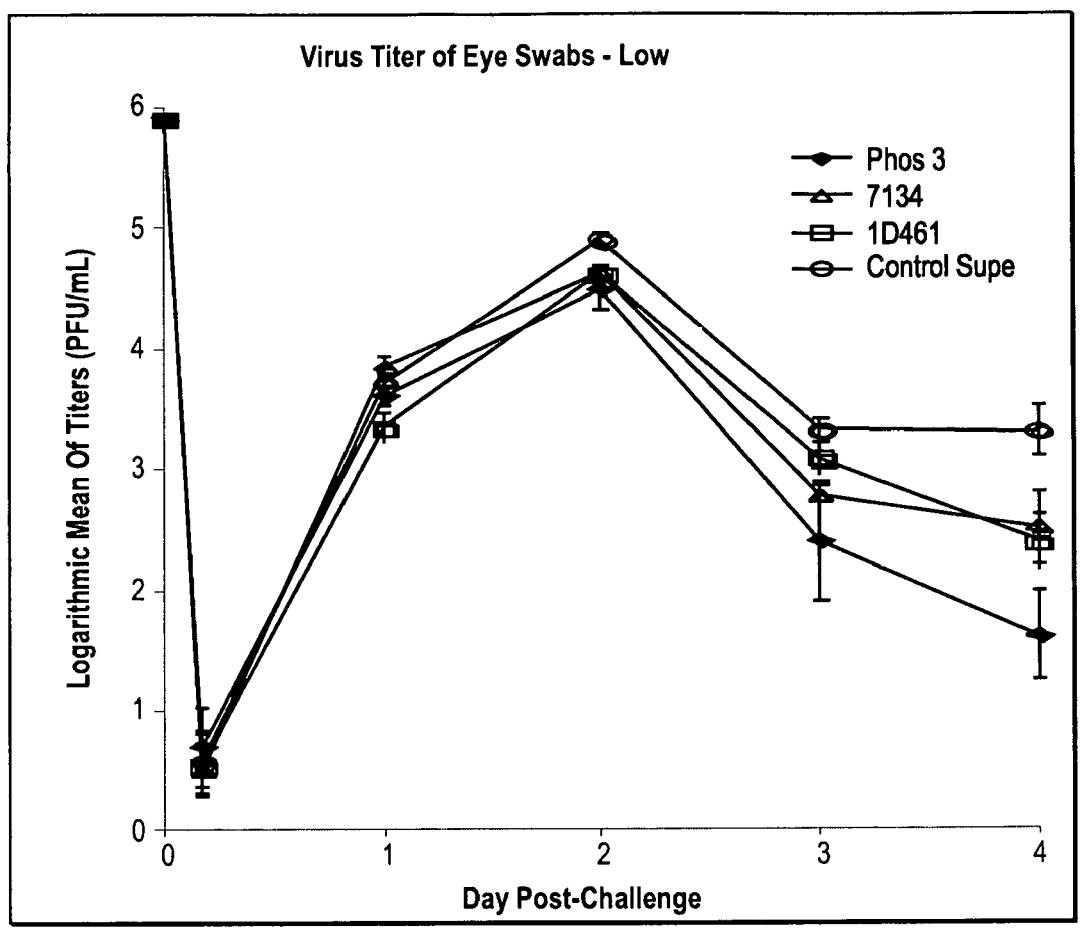

FIGS. 12A-12C show viral titer of eye swabs after corneal challenge with HSV-1 when the mice were immunized with high (12A), medium (12B) or low (12C) doses of ICP0-null mutant (7134), phosphorylation site mutant (Phos 3), control virus (1D416), and cell extract (control supernatant).a Example 5

Phosphorylated residues in ICP0 were detected using microcapillary reverse-phase HPLC nano-electrospray tandem mass spectrometry. Using an in-house program, Enzyme Optimizer, the ICP0 sequence was evaluated for a dual enzyme strategy which would optimize for coverage of S/T/Y residues. The program considers peptide properties and experimental conditions that influence recovery and detection of a predicted peptide, rather than simple protein coverage. The band corresponding to ICP0 was then split in half for separate, in gel trypsin and chymotryptic digestions after reduction, and carboxyamidomethylation. The resultant digests were pooled just prior to LC-MS/MS injection. Phosphorylated peptide sequences were determined using a 75-μm reverse phase microcolumn terminating in a custom nano-electrospray source directly coupled to a Finnigan LCQ DECA XP+ quadrupole ion trap mass spectrometer (Thermo Electron). The flow rate was nominally 250 nl/min. The ion trap repetitively surveyed the range m/z 395-1600, executing data-dependent MS/MS on the four most abundant ions in each survey scan. MS/MS spectra were acquired with a relative collision energy of 30%, a 2.5 Da isolation width, and recurring ions dynamically excluded. Preliminary sequencing of peptides was facilitated by database correlation with the algorithm SEQUEST. The discovery of peptides carrying phosphorylation and subsequent manual validation of their MS/MS spectra were aided by the in-house programs Muquest and Fuzzylons, respectively.

Based on μLC-MS/MS analysis, each of the 3 phosphorylated regions of ICP0 identified lies within or overlaps domains reported to be important for ICP0's transactivating activity. Thus, the four mutations in Phos 1 at positions 224, 226, 231, and 232 are adjacent to the RING-finger motif of ICP0, which is required for its E3 ubiquitin ligase and trans-activating activities. This study has shown that the Phos 1 form of ICP0 is impaired in its transactivating activity and in its ability to complement the replication of an ICP0 null mutant but not its ability to degrade and/or disperse ND10. Insertion and deletion mutations in region I or between region I and ICP0's RING finger have been shown to diminish both the transactivating activity of ICP0 and its ability to co-localize with conjugated ubiquitin; the latter activity is consistent with ICP0's E3 ubiquitin ligase activity. Mutations in the RING finger motif (residues 116-156) and an adjacent region (residues 162-188) show a range of ND10-disrupting phenotypes that are distinct from the phenotype of WT ICP0. To date, however, the ND10-disrupting activities of the majority of ICP0 mutants with mutations that lie in region I and between region I and the RING finger motif have not been reported. Additionally, mutation of Asp-199 (which lies between region I and the RING finger motif) to alanine negates the binding of ICP0 to cyclin D3, accelerating the destabilization of cyclin D3. This mutation attenuates the pathogenesis of HSV-1. Residues 20-241 of ICP0 have been shown to interact with the cellular transcription factor, BMAL1. The interaction of ICP0 with BMAL1 is thought to facilitate synergistic transactivation of BMAL-1 responsive genes. Thus, it is possible that the effects we observed with the Phos 1 mutations in Vero cells result from alterations in these adjacent regions. Of interest is the fact that the phenotypes of Phos 1 are strikingly similar to the phenotypes of ICP0 synthesized in the presence of the cdk inhibitor, Rosco. Specifically, ICP0 synthesized in the presence of Rosco is impaired in its transactivating activity but not its ND10-disrupting activity. Thus, Rosco-sensitive cdk-mediated phosphorylation of phospho-acceptor sites in region I of ICP0, and especially Ser-224 which is a potential cdk-1 or -2 phosphorylation site, may contribute to ICP0's transactivating activity.

The mutations in Phos 2 at positions 365, 367, and 371 lie within a large proline-rich domain important for ICP0's transactivating activity. Phos 2 was affected only in its capacity to disperse or degrade ND10-associated PML in a subset of Phos 2 expressing cells; the transactivating- and 7134-complementing activities of Phos 2 were only minimally affected relative to WT ICP0. A previous study noted a reduction in ICP0's transactivating activity in a mutant form of ICP0 lacking residues 263-448, which includes all of region II. Consistent with the transactivating potential of Phos 2, a report by Everett noted that an insertion in region II at residue 370 and deletion of residues 341-374 had marginal effects on ICP0-mediated transactivation in Vero cells. The ability of these deletion and insertion mutants to affect the dispersal or degradation of ND10-associated proteins (including PML) has not been reported. Notably, the magnitude of the impairment in the transactivating activity of these mutants correlates with the severity of their mutations.

Mutations in Phos 3 at positions 508, 514, 517, and 518 overlap the putative nuclear localization signal (NLS) of ICP0 and are adjacent to its multi-functional C-terminal domain. Phos 3 was affected in its subcellular and nuclear localization and its ability to disperse or degrade PML in a subset of cells expressing Phos 3; however, these mutations only minimally affected its ability to complement 7134 in Vero cells. The diminished transactivation potential of Phos 3 may also be due to its altered subcellular and/or subnuclear localization. Similar observations have been reported for deletion mutants of ICP0 which eliminate its putative NLS. Notably, a proportion of cells expressing these deletion mutants co-localized with ND10-associated proteins in the cytoplasm similar to our observations with PML and Phos 3. Because the mutations in Phos 3 are directly adjacent to the putative NLS of ICP0 and because phosphorylation of the NLS may affect nuclear import, Phos 3 may be inefficiently transported to or from the nucleus as our immunofluorescence data suggest. In support of this possibility, mutagenesis of potential phosphorylation sites has been shown to regulate the subcellular localization of viral regulatory proteins from DNA-containing viruses including T-ag of SV40, pp 65 of human cytomegalovirus, latent nuclear antigen of Kaposi's sarcoma herpesvirus, IE63 protein of varicella zoster virus, and US11, an RNA-binding protein, and ICP27 of HSV-1. Of the viral regulatory proteins just mentioned with the exception of US11, CKII, cdk-1, and PKA have been implicated in their subcellular localization, and putative phosphorylation sites for these cellular kinases have been identified in region III of ICP0. The subcellular localization of Phos 3 may also indirectly affect the phosphorylation state of a portion of ICP0 molecules. For example, if ICP0 is efficiently phosphorylated by nuclear kinases which are required for its biological activities, then impairment of ICP0's nuclear translocation would prevent its phosphorylation by such kinases. Although the mutations in Phos 3 reduced its transactivating activity, they affected its 7134-complementating activity in Vero cells only minimally. These observations demonstrate that Phos 3 possesses sufficient transactivating activity to stimulate the replication of an ICP0 null mutant to levels similar to WT ICP0. This possibility is reinforced by two studies demonstrating that mutant forms of ICP0 exhibiting impaired transactivating activity are capable of supporting significant complementation of an ICP0 null mutant virus. Finally, although we examined the phenotypic effects of the Phos 1, 2, and 3 mutations in Vero cells, it is conceivable that these mutations may have cell type-specific effects in the functional assays used in this study, alter other known activities of ICP0 (e.g., E3 ubiquitin ligase activity, accumulation of conjugated ubiquitin, cell cycle-blocking activity), and/or have distinct phenotypes in the context of viral infection in vivo. These possibilities warrant further investigation.

Example 6

Plasmid pIE3-CAT, which expresses the chloramphenicol acetyl transferase (CAT) gene under the control of the HSV-1 IE ICP4 promoter, was constructed as previously described in the art. Plasmid pAlter-1+ICP0 was constructed by isolating a 4.6 kb EcoRI to HindIII fragment containing the ICP0 gene from the plasmid pSH, and cloned into the vector pAlter-1 (Promega Corp. Madison, Wis.), using the same restriction enzyme sites. pAlter-1+ICP0 was subsequently used as the parental vector to mutate the putative phosphorylation sites of ICP0 to alanine using mutagenic primers (IDT, Coralville, Iowa) according to the manufacturer's protocol (Promega Corp., Madison, Wis.). The primers used for the mutagenesis are: Phos 1 (S224A, T226A, T231A, T232A) 5'CTG-GGGGGGCACACGGTGAGGGCCCTagCGCCggCCCA-CCCTGAGCCggCCgCGGACGAGGATGACGACGACC-TGGAC3' (SEQ ID NO: 5); Phos 2 (S365A, S367A, S371A) 5'GCAAACAACAGAGACCCCATAGTGATCgcCGAtg-CCCCCCCGGCCgCTCCCACAGGCCCCCCGCGGCG-CCC3' (SEQ ID NO: 6); and Phos 3 (S508A, S514A, S517A, T518A) 5'GCGGTGCGTCCGAGGAAGAGGCGCGGGg-CcGGCCAGGAAAACCCCgCCCCgCAGgCCgCGCGTC-CCCCCCTCGCGCCGGCAGGGG3' (SEQ ID NO: 7). Lower case letters in each primer indicate the nucleotides mutated relative to WT (strain KOS) ICP0 sequences. Putative mutants were identified by restriction enzyme analysis and confirmed by DNA sequencing.

Example 7

ICP0 proteins were prepared. Vero cells were plated at $5 \times 10^5$ cells per 60mm dish, and at 2 h prior to transfection (22 h post-plating), medium was changed. Twenty four h after plating, transfections were performed with Lipofectamine 2000 (Invitrogen Corp., Carlsbad, Calif.) according to the manufacturer's protocol using 8 µg of plasmid or salmon sperm DNA and 16 µl of Lipofectamine 2000 diluted in Opti-MEM (Invitrogen Corp.). The DNA/Lipofectamine 2000 mixture was subsequently added to plates containing 5 ml of Opti-MEM in a dropwise manner and left on the cells for 4 h at 37° C. Four h after transfection, cells were pretreated for 1 h with CHX [50 µg/ml] and mock-infected or infected with 5 PFU of KOS or 7134/cell for 1 h at 37° C. in the presence of CHX. After 1 h adsorption, inoculum was removed, cells were washed 3 times with PBS containing CHX, 4 ml of Vero cell medium plus CHX was added per dish, and dishes were incubated for 4.5 h p.i. at 37° C. At t=5.5 h p.i., cells were pre-incubated for 0.5 h in phosphate- or methionine/cystine-free DMEM containing CHX. At t=6 h p.i., medium was removed, and infected cells were washed three times with phosphate- or methionine/cystine-free DMEM containing 1% FCS. Cells were then labeled with 500 µCi of $^{32}P_i$ or 100 µCi [$^{35}S$]methionine/cysteine (PerkinElmer Life Sciences, Inc., Boston, Mass.) in phosphate-, or methionine/cystine-free DMEM containing 1% FCS, respectively, for an additional 6 h. At t=12 h p.i., cells were washed twice with ice-cold PBS, scraped into 1 ml of ice-cold RIPA lysis buffer containing protease inhibitors as described above in the "Partial purification of ICP0 for µLC-MS/MS sequencing". Extract preparation, immunoprecipitation of ICP0, and SDS-PAGE analysis were performed as described previously. Proteins were visualized, and their signal intensities were quantified by PhosphorImager analysis (Amersham Biosciences, Piscataway, N.J.).

Example 8

ICP0 was subjected to phosphotryptic peptide digestion and one-dimensional alkaline gel electrophoresis. $^{32}$P-labeled bands of WT ICP0 or its mutant forms were excised from the SDS-PAGE gel described above and washed two times for 5 min. in fresh ammonium bicarbonate (50 mM). Each gel piece was brought to a final volume of 500 µl with sodium bicarbonate, homogenized with a pestle grinder, and treated with 40 µg of TPCK-treated trypsin (Worthington Biochemicals, Lakewood, N.J.) while gently agitating at 34° C. overnight. An additional 25 µg of TPCK-treated trypsin was added per sample, incubating for a second time overnight at 34° C. Samples were spun at 20,800×g for 10 min. at room temperature, and the resulting supernatant was removed. Remaining protein in the gel pieces was extracted twice by incubating the pieces in 400 µl of acetonitrile-formic acid (1:1) for 20 min. with gentle rocking at room temperature. The acetonitrile-formic acid extracts and the aqueous supernatant of the phosphotryptic digests were pooled (~1200 µl) and dried in a SpeedVac (Savant Instruments, Inc., Farmingdale, N.Y.). Phospholabeled peptides of ICP0 were suspended in 25 µl of sample buffer [0.125 M Tris-HCl buffer (pH 6.8) and 6 M Urea], loaded using equal Cherenkov counts (~1150 cpm), and separated on a 27-cm 30% (w/v) alkaline acrylamide gel as described previously (81) at 10 mA for 44 h. Phosphotryptic peptides from the alkaline gel electrophoresis were visualized by PhosphorImager analysis.

Example 9

Vero cells were stained for ICP0 immunofluorescence. Vero cells were plated on coverslips in 12 well plates, and 22 h later, fresh Vero cell medium was added to each well 2 h prior to transfection. Transfections were performed with Lipofectamine 2000 according to the manufacturer's protocol using 3 µg of plasmid DNA and 6 µl of Lipofectamine 2000 diluted in Opti-MEM (Invitrogen Corp.). The DNA/Lipofectamine 2000 mixture was then added to each well containing 500 µl Opti-MEM in a dropwise manner and left on cells for 5 h at 37° C. Medium was removed and fresh medium added, incubating the monolayers for an additional 19 h. Twenty-four h post-transfection, medium was removed, and coverslips were washed twice with PBS. Transfected cells were fixed and permeabilized by formaldehyde and acetone treatments according to Zhu et al. (86). Immunofluorescence staining for ICP0, its mutant forms, and PML was performed as previously described (17). The primary antibodies and the dilutions used for the dual staining of ICP0 and PML were: ICP0 [1:500] (H1112; mouse monoclonal antibody; Rumbaugh-Goodwin Institute for Cancer Research, Plantation, Fla.) and PML-14 [1:500] (rabbit polyclonal antibody; Gerd Maul, Wistar Institute, Philadelphia, Pa.). The following secondary antibodies and dilutions were used for each primary antibody: ICP0 (H1112) [1:100] (goat anti-mouse IgG conjugated with fluorescein isothiocyanate) and PML-14 [1:100] (goat anti-rabbit immunoglobulin G (IgG) conjugated with rhodamine red-X). All secondary antibodies were purchased from Jackson Immunoresearch (West Grove, Pa.). Following incubations with primary and secondary antibodies, coverslips were washed and 7 µl of Prolong Antifade Solution (Molecular Probes, Eugene, Ore.) was added per coverslip. Cells were viewed by fluorescence microscopy with a Nikon Eclipse TE300 Fluorescence microscope at ×400 magnification and photographed with an RT Slider digital camera (Diagnostic Instruments, Sterling Heights, Mich.), and images were processed in Adobe Photoshop (Adobe Systems Inc., Mountain View, Calif.). Images were assembled and labeled in Canvas 8 (Deneba Systems, Miami, Fla.).

At least 150 ICP0-stained cells from random fields were examined in each preparation and categorized as having nuclear only, nuclear and cytoplasmic, or cytoplasmic only staining. The percentage of cells in each category was determined by dividing the number of cells in a given category by the total number of cells counted in all three categories.

Example 10

Vero cells were transfected with genetic material encoding for ICP0. Vero cells ($5 \times 10^5$ cells per 60-mm dish) were plated, and 2 h before transfection (22 h post-plating), the medium was changed. Twenty-four h after plating, the transfections were performed with Lipofectamine 2000 according to the manufacturer's protocol using a total of 8 µg of DNA [1 µg of CAT expression vector, salmon sperm testis DNA, and/or increasing amounts plasmid DNA] and 16 µl of Lipofectamine 2000 diluted in Opti-MEM per dish. DNA/Lipofectamine 2000 was then added to dishes containing 5 µl of Opti-MEM in a dropwise manner and left on cells for 5 h at 37° C. Medium was removed and fresh Vero cell medium added, incubating the monolayers for an additional 43 h. At 48 h post-transfection, cells were washed three times with tris buffered saline (TBS), harvested in 2 ml TBS, and pelleted at 800×g; the supernatant was removed. The resulting cell pellets were stored at −80° C. Samples were thawed on ice, re-suspended in 150 µl TBS, sonicated for 20 sec. at 80% power in a Misonix Sonicator 3000 (Misonix, Inc., Farmingdale, N.Y.), and cell debris was pelleted for 10 min. at 4° C. at 20,800×g. The resulting supernatant was assayed for CAT activity as performed as is known in the art.

Example 11

The plating efficiency of cells producing HSV-1 and/or ICP0 (wild type or mutant) were examined. Vero cells were plated at $2 \times 10^5$ cells per 35-mm dish. Twenty-two h later, fresh medium was added to each well. Twenty four h post-plating, the transfections were performed with FuGENE 6 (Roche Diagnostic Corporation, Indianapolis, Ind.) using a total of 3 µg DNA (0.5 µg of infectious KOS or 7134 viral DNA (9), salmon sperm DNA, and/or 0.075 µg of plasmid DNA [pAlter-1 or WT ICP0- or Phos mutant-expressing plasmids]) and 12 µl of FuGENE 6 diluted in Opti-MEM. The DNA/FuGENE 6 mixture was divided in half, added dropwise to 35 mm dishes (for duplicate samples) containing 2 µl of Opti-MEM, and left on the cells for 5 h at 37° C. Medium was removed, fresh Vero cell medium added, and monolayers incubated for an additional 43 h. Transfected cells were harvested 48 h post-transfection and assayed for infectious virus by standard plaque assays on Vero cells for KOS or on L7 cells for 7134.

For the 7134 plating efficiency experiments, cells were transfected as described in the art, with the following modifications. Five hours post-transfection, medium was removed from each culture and replaced with 2.5 ml of medium containing 0.5% methylcellulose and 10% FCS in DMEM. Three days post-transfection, methylcellulose containing medium was removed from each plate, and cells were washed twice with PBS, fixed with 2% formaldehyde, and stained for β-galactosidase activity with X-gal as described in the art. X-gal staining was performed to note the spread of 7134 infection (7134 contains the lacZ gene in place of both copies of ICP0) by counting CBF (cytopathic blue foci: clusters of 8 or more cells exhibiting cytopathic effect) per quadrant (¼ the area of each dish).

Example 12

ICP0 was partially purified. Four 100-mm dishes were seeded with $2 \times 10^6$ Vero cells, and 23 h after plating cells, were pretreated with cycloheximide (CHX [50 µg/ml]) for 1 h and infected with 5 PFU of KOS/cell for 1 h at 37° C. in the presence of CHX. After 1 h adsorption, inoculum was removed, cells were washed three times with phosphate buffered saline (PBS) containing CHX. Five ml of Vero cell medium containing CHX was then added to each dish, and cells subsequently were incubated for h [t=6 h post-infection (p.i.)] at 37° C. At t=6 h p.i., medium was removed, and infected cells were washed three times with PBS and incubated for an additional 6 h. At t=12 h p.i., cells were washed twice with ice-cold PBS, scraped into 2 ml of ice-cold PBS, and pelleted at 800×g at 4° C. The supernatant fluid was removed, and the resulting cell pellets were stored at −80° C. Subsequently, samples were thawed on ice, and re-suspended in 2 ml of RIPA lysis buffer [150 mM NaCl, 50 mM Tris (pH 7.5), 0.1% sodium lauryl sulfate (SDS), 1% Nonidet P-40, and 0.5% deoxycholic acid] containing the protease inhibitors phenylmethysulfonylfluoride [1 mM], 1 µg of leupeptin/ml, and 1 µg of aprotinin/ml. Eight µl of J17, an ICP0 polyclonal rabbit antibody, was added per sample and the suspensions were gently agitated overnight at 4° C. The next day, 160 µl of protein A-agarose (Invitrogen Life Technologies, Carlsbad, Calif.) was added to each sample and agitated for 2 h at 4° C. Immune complexes were pelleted by centrifugation for 2 min, 3,300×g at 4° C. The supernatant fluid was removed, and each pellet was washed and repelleted three times in RIPA buffer plus protease inhibitors. The resulting pellet was re-suspended in 60 µl of 1× Laemmli buffer plus 1 mM PMSF. Samples were heated at 100° C. for 5 min, placed on ice for 2 min, and centrifuged to pellet the protein A-agarose. The supernatants were analyzed by sodium dodecyl sulfate-polyacrylamide gel electrophoresis (SDS-PAGE) on a 0.75 mm 6% acrylamide gel. Proteins were visualized by Coomassie Blue staining and an estimate of the total amount of ICP0 protein isolated (1.5 µg) was determined relative to a standard curve of bovine serum albumin. Gel pieces containing ICP0 bands were marked, destained for Coomassie Blue dye, excised, and stored at −20° C. until further analysis.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A mutant herpes simplex virus type 1 (HSV-1) comprising:

a mutant infected cell protein 0 (ICP0) of HSV-1 having a mutation in at least one phosphorylation site between amino acid 505 and amino acid 528, said mutation being configured to inhibit phosphorylation of said at least one phosphorylation site.

2. A mutant HSV as in claim 1, wherein the mutation is an amino acid substitution, insertion, deletion, or combination thereof.

3. A mutant HSV as in claim 2, wherein the mutation is a substitution of at least one serine and/or threonine amino acid between amino acid 505 and amino acid 528 with a different amino acid.

4. A mutant HSV as in claim 2, wherein the mutation is a substitution of at least one serine and/or threonine amino acid between amino acid 505 and amino acid 528 with an alanine amino acid.

5. A mutant HSV as in claim 3, wherein the mutation is a substitution of at least one serine and/or threonine amino acid in at least one of amino acids S508, S514, S517, or T518 with a phosphorylation-inhibiting amino acid.

6. A mutant HSV as in claim 5, wherein the mutations correspond with SEQ ID NO: 2 or 4.

7. A mutant HSV as in claim 1, wherein the mutant HSV-1 is disposed in an immunogenic composition.

8. A mutant simplex virus type 2 (HSV-2) comprising:

a mutant infected cell protein 0 (ICP0) of HSV-2 having a mutation in at least one phosphorylation site between amino acid 518 and amino acid 531, said mutation being configured to inhibit phosphorylation of said at least one phosphorylation site.

9. A mutant HSV as in claim 8, wherein the mutation is a substitution of at least one serine and/or threonine amino acid between amino acid 518 and amino acid 531 with a different amino acid.

10. A mutant HSV as in claim 8, wherein the mutation is a substitution of at least one serine and/or threonine amino acid between amino acid 518 and amino acid 531 with an alanine amino acid.

11. A mutant HSV as in claim 10, wherein the mutations correspond with SEQ ID NO: 8.

12. A mutant HSV as in claim 8, wherein the mutant HSV-2 is disposed in an immunogenic composition.

13. An immunogenic composition for herpes simplex virus (HSV), the immunogenic composition comprising:

a pharmaceutically acceptable carrier; and a mutant infected cell protein 0 (ICP0) of mutant HSV-1 and/or HSV-2 having a mutation in at least one phosphorylation site of the ICP0 protein, the at least one phosphorylation site being between amino acid 505 and amino acid 528 for the HSV-1 ICP0, said mutation being configured to inhibit phosphorylation of said at least one phosphorylation site.

14. An immunogenic composition as in claim 13, wherein the mutation is an amino acid substitution, insertion, deletion, or combination thereof.

15. An immunogenic composition as in claim 13, wherein the mutation is a substitution of at least one serine and/or threonine amino acid between amino acid 505 and amino acid 528 with a different amino acid for the HSV-1 ICP0.

16. An immunogenic composition as in claim 13, wherein the mutation is a substitution of at least one serine and/or threonine amino acid between amino acid 505 and amino acid 528 with an alanine amino acid for the HSV-1 ICP0.

17. An immunogenic composition as in claim 13, wherein the mutation is a substitution of at least one serine and/or threonine amino acid in at least one of amino acids S508, S514, S517, or T518 with a phosphorylation-inhibiting amino acid for the HSV-1 ICP0.

18. An immunogenic composition as in claim 17, wherein the mutations correspond with SEQ ID NO: 2 or 4.

19. An immunogenic composition as in claim 14, wherein the mutation is between amino acid 518 and amino acid 531 for the HSV-2 ICP0.

20. An immunogenic composition as in claim 19, wherein the mutation is a substitution of at least one serine and/or threonine amino acid between amino acid 518 and amino acid 531 with a different amino acid for the HSV-2 ICP0.

21. An immunogenic composition as in claim 19, wherein the mutation is a substitution of at least one serine and/or threonine amino acid between amino acid 518 and amino acid 531 with an alanine amino acid for the HSV-2 ICP0.

22. An immunogenic composition as in claim 21, wherein the mutations correspond with SEQ ID NO: 8.

23. An immunogenic composition as in claim 13, wherein the mutant ICP0 is disposed in a viral particle within the composition.

24. An immunogenic composition as in claim 19, wherein the mutation is a substitution of at least one serine and/or threonine amino acid in at least one of amino acids S518 or S530 with a phosphorylation-inhibiting amino acid for the HSV-2 ICP0.

25. A mutant virus as in claim 8, wherein the mutation is a substitution of at least one serine and/or threonine amino acid in at least one of amino acids S518 or S530 with a phosphorylation-inhibiting amino acid for the HSV-2 ICP0.

* * * * *

SEQUENCE LISTING

<160> NUMBER OF SEQ ID NOS: 8

<210> SEQ ID NO 1
<211> LENGTH: 3645
<212> TYPE: DNA
<213> ORGANISM: herpes simplex virus 1
<220> FEATURE:
<221> NAME/KEY: CDS
<222> LOCATION: (3)..(59)
<220> FEATURE:
<221> NAME/KEY: CDS
<222> LOCATION: (825)..(1490)
<220> FEATURE:
<221> NAME/KEY: CDS
<222> LOCATION: (1627)..(3228)

<400> SEQUENCE: 1

```
cc atg gag ccc cgc ccc gga gcg agt acc cgc cgg cct gag ggc cgc          47
   Met Glu Pro Arg Pro Gly Ala Ser Thr Arg Arg Pro Glu Gly Arg
    1               5                  10                  15 ccc cag cgc gag gtgaggggcc gggcgccatg tctgggcgc catattgggg              99
Pro Gln Arg Glu ggcgccatat tggggggcgc catgttgggg accccgac ccttacactg gaaccggccg        159
ccatgttggg ggaccccac tcatacacg gagccgggcg ccatgttggg gcgccatgtt        219 aggggggcgtg gaaccccgtg acactatata tacagggacc gggggcgcca tgttagggg       279 tgcggaaccc cctgacccta tatatacagg gaccggggtc gccctgttgg gggtcgccat       339 gtgacccct gactttatat atacagaccc ccaacacata cacatggccc ctttgactca       399
gacgcagggc ccggggtcgc cgtgggaccc cctgactcat acacagagac acgccccac       459 aacaaacaca caaggaccgg gtcgccgtg ttggggggcgt ggtccccact gactcatacg      519 caggccccc ttactcacac gcatctaggg gggtggggag gagccgcccg ccatatttgg       579
gggacgccgt gggaccccg actccggtgc gtctggaggg cgggagaaga gggaagaaga      639
ggggtcggga tccaaaggac ggacccgac caccttggt tgcagacccc ttctccccc         699 ctcttccgag gccagcaggg gggcaggact ttgtgaggcg gggggggagg gaggggaact      759
cgtgggtgct gattgacgcg ggaaatcccc ccccattctt acccgccccc cttttttccc      819 cttag ccc gcc ccg gat gtc tgg gtg ttt ccc tgc gac cga gac ctg ccg      869
     Pro Ala Pro Asp Val Trp Val Phe Pro Cys Asp Arg Asp Leu Pro
           20                  25                  30 gac agc agc gac tct gag gcg gag acc gaa gtg ggg ggg cgg ggg gac        917
Asp Ser Ser Asp Ser Glu Ala Glu Thr Glu Val Gly Gly Arg Gly Asp
 35                  40                  45                  50 gcc gac cac cat gac gac gac tcc gcc tcc gag gcg gac agc acg gac        965
Ala Asp His His Asp Asp Asp Ser Ala Ser Glu Ala Asp Ser Thr Asp
                55                  60                  65 acg gaa ctg ttc gag acg ggg ctg ctg ggg ccg cag ggc gtg gat ggg       1013
Thr Glu Leu Phe Glu Thr Gly Leu Leu Gly Pro Gln Gly Val Asp Gly
         70                  75                  80 ggg gcg gtc tcg ggg ggg agc ccc ccc cgc gag gaa gac ccc ggc agt       1061
Gly Ala Val Ser Gly Gly Ser Pro Pro Arg Glu Glu Asp Pro Gly Ser
             85                  90                  95 tgc ggg ggc gcc ccc cct cga gag gac ggg ggg agc gac gag ggc gac       1109
Cys Gly Gly Ala Pro Pro Arg Glu Asp Gly Gly Ser Asp Glu Gly Asp
        100                 105                 110 gtg tgc gcc gtg tgc acg gat gag atc gcg ccc cac ctg cgc tgc gac       1157
Val Cys Ala Val Cys Thr Asp Glu Ile Ala Pro His Leu Arg Cys Asp
115                 120                 125                 130
```

```
acc ttc ccg tgc atg cac cgc ttc tgc atc ccg tgc atg aaa acc tgg    1205
Thr Phe Pro Cys Met His Arg Phe Cys Ile Pro Cys Met Lys Thr Trp
            135                 140                 145 atg caa ttg cgc aac acc tgc ccg ctg tgc aac gcc aag ctg gtg tac    1253
Met Gln Leu Arg Asn Thr Cys Pro Leu Cys Asn Ala Lys Leu Val Tyr
        150                 155                 160 ctg ata gtg ggc gtg acg ccc agc ggg tcg ttc agc acc atc ccg atc    1301
Leu Ile Val Gly Val Thr Pro Ser Gly Ser Phe Ser Thr Ile Pro Ile
            165                 170                 175 gtg aac gac ccc cag acc cgc atg gag gcc gag gag gcc gtc agg gcg    1349
Val Asn Asp Pro Gln Thr Arg Met Glu Ala Glu Glu Ala Val Arg Ala
        180                 185                 190 ggc acg gcc gtg gac ttt atc tgg acg ggc aat cag cgg ttc gcc ccg    1397
Gly Thr Ala Val Asp Phe Ile Trp Thr Gly Asn Gln Arg Phe Ala Pro
195                 200                 205                 210 cgg tac ctg acc ctg ggg ggg cac acg gtg agg gcc ctg tcg ccc acc    1445
Arg Tyr Leu Thr Leu Gly Gly His Thr Val Arg Ala Leu Ser Pro Thr
                215                 220                 225 cac ccg gag ccc acc acg gac gag gat gac gac gac ctg gac gac        1490
His Pro Glu Pro Thr Thr Asp Glu Asp Asp Asp Asp Leu Asp Asp
            230                 235                 240 ggtgaggcgg ggggcggcaa ggaccctggg ggaggaggag gaggaggggg ggggagggag  1550
gaataggcgg gcgggcgagg aaagggcggg ccggggaggg ggcgtaacct gatcgcgccc  1610
cccgttgtct cttgca gca gac tac gta ccg ccc gcc ccc cgc cgg acg ccc  1662
               Ala Asp Tyr Val Pro Pro Ala Pro Arg Arg Thr Pro
                           245                 250 cgc gcc ccc cca cgc aga ggc gcc gcc gcg ccc ccc gtg acg ggc ggg    1710
Arg Ala Pro Pro Arg Arg Gly Ala Ala Ala Pro Pro Val Thr Gly Gly
        255                 260                 265 gcg tct cac gca gcc ccc cag ccg gcc gcg gct cgg aca gcg ccc ccc    1758
Ala Ser His Ala Ala Pro Gln Pro Ala Ala Ala Arg Thr Ala Pro Pro
270                 275                 280                 285 tcg gcg ccc atc ggg cca cac ggc agc agt aac acc aac acc acc acc    1806
Ser Ala Pro Ile Gly Pro His Gly Ser Ser Asn Thr Asn Thr Thr Thr
                290                 295                 300 aac agc agc ggc ggc ggc tcc cgc cag tcg cga gcc gcg gcg ccg        1854
Asn Ser Ser Gly Gly Gly Ser Arg Gln Ser Arg Ala Ala Ala Pro
            305                 310                 315 cgg ggg gcg tct ggc ccc tcc ggg ggg gtt ggg gtt ggg gtt ggg gtt    1902
Arg Gly Ala Ser Gly Pro Ser Gly Gly Val Gly Val Gly Val Gly Val
        320                 325                 330 gtt gaa gcg gag gcg ggg cgg ccg agg ggc cgg acg ggc ccc ctt gtc    1950
Val Glu Ala Glu Ala Gly Arg Pro Arg Gly Arg Thr Gly Pro Leu Val
335                 340                 345 aac aga ccc gcc ccc ctt gca aac aac aga gac ccc ata gtg atc agc    1998
Asn Arg Pro Ala Pro Leu Ala Asn Asn Arg Asp Pro Ile Val Ile Ser
350                 355                 360                 365 gac tcc ccc ccg gcc tct ccc cac agg ccc ccc gcg gcg ccc atg cca    2046
Asp Ser Pro Pro Ala Ser Pro His Arg Pro Pro Ala Ala Pro Met Pro
                370                 375                 380 ggc tcc gcc ccc cgc ccc ggg ccc ccc gcg tcc gcg gcc gcg tcg gga    2094
Gly Ser Ala Pro Arg Pro Gly Pro Pro Ala Ser Ala Ala Ala Ser Gly
            385                 390                 395 ccc gcg cgc ccc cgc gcg gcc gtg gcc ccg tgc gtg cga gcg ccg cct    2142
Pro Ala Arg Pro Arg Ala Ala Val Ala Pro Cys Val Arg Ala Pro Pro
        400                 405                 410
```

```
                                                        -continued
ccg ggg ccc ggc ccc cgc gcc ccg gcc ccc ggg gcg gag ccg gcc gcc    2190
Pro Gly Pro Gly Pro Arg Ala Pro Ala Pro Gly Ala Glu Pro Ala Ala
    415                 420                 425 cgc ccc gcg gac gcg cgc cgt gtg ccc cag tcg cac tcg tcc ctg gct    2238
Arg Pro Ala Asp Ala Arg Arg Val Pro Gln Ser His Ser Ser Leu Ala
430                 435                 440                 445 cag gcc gcg aac caa gaa cag agt ctg tgc cgg gcg cgt gcg acg gtg    2286
Gln Ala Ala Asn Gln Glu Gln Ser Leu Cys Arg Ala Arg Ala Thr Val
                450                 455                 460 gcg cgc ggc tcg ggg ggg ccg ggc gtg gag ggt ggg cac ggg ccc tcc    2334
Ala Arg Gly Ser Gly Gly Pro Gly Val Glu Gly Gly His Gly Pro Ser
            465                 470                 475 cgc ggc gcc gcc ccc tcc ggc gcc gcc ccg ctc ccc tcc gcc gcc tct    2382
Arg Gly Ala Ala Pro Ser Gly Ala Ala Pro Leu Pro Ser Ala Ala Ser
        480                 485                 490 gtc gag cag gag gcg gcg gtg cgt ccg agg aag agg cgc ggg tcg ggc    2430
Val Glu Gln Glu Ala Ala Val Arg Pro Arg Lys Arg Arg Gly Ser Gly
    495                 500                 505 cag gaa aac ccc tcc ccc cag tcc acg cgt ccc ccc ctc gcg ccg gca    2478
Gln Glu Asn Pro Ser Pro Gln Ser Thr Arg Pro Pro Leu Ala Pro Ala
510                 515                 520                 525 ggg gcc aag agg gcg gcg acg cac ccc ccc tcc gac tca ggg ccg ggg    2526
Gly Ala Lys Arg Ala Ala Thr His Pro Pro Ser Asp Ser Gly Pro Gly
                530                 535                 540 ggg cgc ggc cag ggt ggg ccc ggg acc ccc ctg acg tcg tcg gcg gcc    2574
Gly Arg Gly Gln Gly Gly Pro Gly Thr Pro Leu Thr Ser Ser Ala Ala
            545                 550                 555 tcc gcc tct tcc tcc tct gcc tct tcc tcg gcc ccg acc ccc gcg        2622
Ser Ala Ser Ser Ser Ser Ala Ser Ser Ser Ser Ala Pro Thr Pro Ala
        560                 565                 570 ggg gcc gcc tct tcc gcc gcc ggg gcc gcg tcc tcc tcc gct tcc gcc    2670
Gly Ala Ala Ser Ser Ala Ala Gly Ala Ala Ser Ser Ser Ala Ser Ala
    575                 580                 585 tcc tcg ggc ggg gcc gtc ggt gcc ctg gga ggg aga caa gag gaa acc    2718
Ser Ser Gly Gly Ala Val Gly Ala Leu Gly Gly Arg Gln Glu Glu Thr
590                 595                 600                 605 tcc ctc ggc ccc cgc gct gct tct ggg ccg cgg ggg ccg agg aag tgt    2766
Ser Leu Gly Pro Arg Ala Ala Ser Gly Pro Arg Gly Pro Arg Lys Cys
                610                 615                 620 gcc cgg aag acg cgc cac gcg gag act tcc ggg gcc gtc ccc gcg ggc    2814
Ala Arg Lys Thr Arg His Ala Glu Thr Ser Gly Ala Val Pro Ala Gly
            625                 630                 635 ggc ctc acg cgc tac ctg ccc atc tcg ggg gtc tct agc gtg gtc gcc    2862
Gly Leu Thr Arg Tyr Leu Pro Ile Ser Gly Val Ser Ser Val Val Ala
        640                 645                 650 ctg tcg cct tac gtg aac aag act atc acg ggg gac tgc ctg ccc atc    2910
Leu Ser Pro Tyr Val Asn Lys Thr Ile Thr Gly Asp Cys Leu Pro Ile
    655                 660                 665 ctg gac atg gag acg ggg aac atc ggg gcg tac gtg gtc ctg gtg gac    2958
Leu Asp Met Glu Thr Gly Asn Ile Gly Ala Tyr Val Val Leu Val Asp
670                 675                 680                 685 cag acg gga aac atg gcg acc cgg ctg cgg gcc gcg gtc ccc ggc tgg    3006
Gln Thr Gly Asn Met Ala Thr Arg Leu Arg Ala Ala Val Pro Gly Trp
                690                 695                 700 agc cgc cgc acc ctg ctc ccc gag acc gcg ggt aac cac gtg atg ccc    3054
Ser Arg Arg Thr Leu Leu Pro Glu Thr Ala Gly Asn His Val Met Pro
            705                 710                 715 ccc gag tac ccg acg gcc ccc gcg tcg gag tgg aac agc ctc tgg atg    3102
Pro Glu Tyr Pro Thr Ala Pro Ala Ser Glu Trp Asn Ser Leu Trp Met
        720                 725                 730
```

```
acc ccc gtg ggg aac atg ctg ttc gac cag ggc acc cta gtg ggc gcc      3150
Thr Pro Val Gly Asn Met Leu Phe Asp Gln Gly Thr Leu Val Gly Ala
    735                 740                 745 ctg gac ttc cgc agc ctg cgg tct cgg cac ccg tgg tcc ggg gag cag      3198
Leu Asp Phe Arg Ser Leu Arg Ser Arg His Pro Trp Ser Gly Glu Gln
750                 755                 760                 765 ggg gcg tcg acc cgg gac gag gga aaa caa taagggacgc ccccgtgtt         3248
Gly Ala Ser Thr Arg Asp Glu Gly Lys Gln
                770                 775 tgtggggagg gggggtcgg gcgctgggtg gtctctggcc gcgcccacta caccagccaa     3308
tccgtgtcgg ggaggggaaa agtgaaagac acgggcacca cacaccagcg ggtcttttgt    3368
gttggcccta ataaaaaaaa actcagggga ttttgctgt ctgttgggaa ataaaggttt     3428
acttttgtat cttttccctg tctgtgttgg atgtatcgcg gggatgcgtg ggagtggggg    3488
tgcgtgggag tggggtgcg tgggagtggg ggtgcgtggg agtggggtg cgtgggagtg      3548 gggtgcgtg ggagtggggg tgcgtgggag tggggtgcg tgggagtggg ggtgcgtggg      3608 agtggggtg ccatgttggg caggctctgg tgttaac                              3645

<210> SEQ ID NO 2
<211> LENGTH: 775
<212> TYPE: PRT
<213> ORGANISM: herpes simplex virus 1

<400> SEQUENCE: 2

Met Glu Pro Arg Pro Gly Ala Ser Thr Arg Arg Pro Glu Gly Arg Pro
 1               5                  10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Gly Ser Pro Pro Arg Glu Glu Asp Pro
                85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
        115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175

Pro Ile Val Asn Asp Pro Gln Thr Arg Met Glu Ala Glu Glu Ala Val
            180                 185                 190

Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Asp Glu Asp Asp Asp Leu Asp
225                 230                 235                 240
```

-continued

```
Asp Ala Asp Tyr Val Pro Pro Ala Pro Arg Thr Pro Arg Ala Pro
                245                 250                 255

Pro Arg Arg Gly Ala Ala Ala Pro Pro Val Thr Gly Gly Ala Ser His
            260                 265                 270

Ala Ala Pro Gln Pro Ala Ala Ala Arg Thr Ala Pro Pro Ser Ala Pro
        275                 280                 285

Ile Gly Pro His Gly Ser Ser Asn Thr Asn Thr Thr Asn Ser Ser
    290                 295                 300

Gly Gly Gly Gly Ser Arg Gln Ser Arg Ala Ala Pro Arg Gly Ala
305                 310                 315                 320

Ser Gly Pro Ser Gly Gly Val Gly Val Gly Val Val Glu Ala
                325                 330                 335

Glu Ala Gly Arg Pro Arg Gly Arg Thr Gly Pro Leu Val Asn Arg Pro
            340                 345                 350

Ala Pro Leu Ala Asn Asn Arg Asp Pro Ile Val Ile Ser Asp Ser Pro
        355                 360                 365

Pro Ala Ser Pro His Arg Pro Pro Ala Ala Pro Met Pro Gly Ser Ala
    370                 375                 380

Pro Arg Pro Gly Pro Pro Ala Ser Ala Ala Ala Ser Gly Pro Ala Arg
385                 390                 395                 400

Pro Arg Ala Ala Val Ala Pro Cys Val Arg Ala Pro Pro Gly Pro
                405                 410                 415

Gly Pro Arg Ala Pro Ala Pro Gly Ala Glu Pro Ala Ala Arg Pro Ala
            420                 425                 430

Asp Ala Arg Arg Val Pro Gln Ser His Ser Ser Leu Ala Gln Ala Ala
        435                 440                 445

Asn Gln Glu Gln Ser Leu Cys Arg Ala Arg Ala Thr Val Ala Arg Gly
    450                 455                 460

Ser Gly Gly Pro Gly Val Glu Gly Gly His Gly Pro Ser Arg Gly Ala
465                 470                 475                 480

Ala Pro Ser Gly Ala Ala Pro Leu Pro Ser Ala Ala Ser Val Glu Gln
                485                 490                 495

Glu Ala Ala Val Arg Pro Arg Lys Arg Arg Gly Ser Gly Gln Glu Asn
            500                 505                 510

Pro Ser Pro Gln Ser Thr Arg Pro Pro Leu Ala Pro Ala Gly Ala Lys
        515                 520                 525

Arg Ala Ala Thr His Pro Pro Ser Asp Ser Gly Pro Gly Gly Arg Gly
    530                 535                 540

Gln Gly Gly Pro Gly Thr Pro Leu Thr Ser Ala Ala Ser Ala Ser
545                 550                 555                 560

Ser Ser Ser Ala Ser Ser Ser Ala Pro Thr Pro Ala Gly Ala Ala
                565                 570                 575

Ser Ser Ala Gly Ala Ala Ser Ser Ala Ser Ala Ser Ser Gly
            580                 585                 590

Gly Ala Val Gly Ala Leu Gly Gly Arg Gln Glu Glu Thr Ser Leu Gly
        595                 600                 605

Pro Arg Ala Ala Ser Gly Pro Arg Gly Pro Arg Lys Cys Ala Arg Lys
    610                 615                 620

Thr Arg His Ala Glu Thr Ser Gly Ala Val Pro Ala Gly Gly Leu Thr
625                 630                 635                 640

Arg Tyr Leu Pro Ile Ser Gly Val Ser Ser Val Val Ala Leu Ser Pro
                645                 650                 655
```

```
            Tyr Val Asn Lys Thr Ile Thr Gly Asp Cys Leu Pro Ile Leu Asp Met
                        660                 665                 670

Glu Thr Gly Asn Ile Gly Ala Tyr Val Val Leu Val Asp Gln Thr Gly
                        675                 680                 685

Asn Met Ala Thr Arg Leu Arg Ala Ala Val Pro Gly Trp Ser Arg Arg
                        690                 695                 700

Thr Leu Pro Glu Thr Ala Gly Asn His Val Met Pro Pro Glu Tyr
            705                 710                 715                 720

Pro Thr Ala Pro Ala Ser Glu Trp Asn Ser Leu Trp Met Thr Pro Val
                        725                 730                 735

Gly Asn Met Leu Phe Asp Gln Gly Thr Leu Val Gly Ala Leu Asp Phe
                        740                 745                 750

Arg Ser Leu Arg Ser Arg His Pro Trp Ser Gly Glu Gln Gly Ala Ser
                        755                 760                 765

Thr Arg Asp Glu Gly Lys Gln
                        770                 775

<210> SEQ ID NO 3
<211> LENGTH: 3298
<212> TYPE: DNA
<213> ORGANISM: herpes simplex virus 1
<220> FEATURE:
<221> NAME/KEY: CDS
<222> LOCATION: (3)..(59)
<220> FEATURE:
<221> NAME/KEY: CDS
<222> LOCATION: (866)..(1531)
<220> FEATURE:
<221> NAME/KEY: CDS
<222> LOCATION: (1670)..(3271)

<400> SEQUENCE: 3 cc atg gag ccc cgc ccc gga gcg agt acc cgc cgg cct gag ggc cgc        47
   Met Glu Pro Arg Pro Gly Ala Ser Thr Arg Arg Pro Glu Gly Arg
   1               5                  10                  15 ccc cag cgc gag gtgaggggcc gggcgccatg tctgggcgc catgtctggg             99
Pro Gln Arg Glu gcgccatgtc tgggcgccaa tgtctgggc gccatgttgg ggggcgccat gttgggggc       159 gccatgttgg gggaccccg accccttacac tggaaccggc cgccatgttg gggaccccc      219 actcatacac gggagccggg cgcccatgtt ggggcgccat gttaggggc gtggaaccc       279 gtgacactat atatacaggg accggggcg ccatgttagg gggcgcggaa ccccctgacc      339
ctatatatac agggaccggg gtcgccctgt tagggtcgc catgtgaccc cctgacttta     399
tatatacaga cccccaacac ctacacatgg ccccctttgac tcagacgcag ggcccggggt    459
cgccgtggga ccccctgac tcatacacag agacacgccc ccacaacaaa cacacaggga    519
ccggggtcgc cgtgttgggg gcgtggtccc cactgactca tacgcagggc cccttactc     579 acacgcatct agggggggtgg ggaggagccg ccgccatat ttgggggacg ccgtgggacc     639
cccgactccg gtgcgtctgg agggcgggag aagagggaag aagagggtc gggatccaaa     699 ggacggaccc agaccaccctt tggttgcaga cccctttctc ccccctcttc cgaggccagc   759
aggggggcag gactttgtga ggcgggggg gggaggggaa ctcgtgggcg ctgattgacg    819
cgggaaatcc ccccattctt acccgccccc ccttttttcc cctcag ccc gcc ccg       874
                                                   Pro Ala Pro
                                                            20 gat gtc tgg gtg ttt ccc tgc gac cga gac ctg ccg gac agc agc gac      922
Asp Val Trp Val Phe Pro Cys Asp Arg Asp Leu Pro Asp Ser Ser Asp
            25                  30                  35
```

```
tcg gag gcg gag acc gaa gtg ggg ggg cgg ggg gac gcc gac cac cat        970
Ser Glu Ala Glu Thr Glu Val Gly Gly Arg Gly Asp Ala Asp His His
    40                  45                  50 gac gac gac tcc gcc tcc gag gcg gac agc acg gac acg gaa ctg ttc       1018
Asp Asp Asp Ser Ala Ser Glu Ala Asp Ser Thr Asp Thr Glu Leu Phe
55                  60                  65                  70 gag acg ggg ctg ctg ggg ccg cag ggt gat ggg ggg gcg gtc tcg           1066
Glu Thr Gly Leu Leu Gly Pro Gln Gly Val Asp Gly Gly Ala Val Ser
                75                  80                  85 ggg ggg agc ccc ccc cgc gag gaa gac ccc ggc agt tgc ggg ggc gcc       1114
Gly Gly Ser Pro Pro Arg Glu Glu Asp Pro Gly Ser Cys Gly Gly Ala
            90                  95                 100 ccc cct cga gag gac ggg ggg agc gac gag ggc gac gtg tgc gcc gtg       1162
Pro Pro Arg Glu Asp Gly Gly Ser Asp Glu Gly Asp Val Cys Ala Val
            105                 110                 115 tgc acg gat gag atc gcg ccc cac ctg cgc tgc gac acc ttc ccg tgc       1210
Cys Thr Asp Glu Ile Ala Pro His Leu Arg Cys Asp Thr Phe Pro Cys
        120                 125                 130 atg cac cgc ttc tgc atc ccg tgc atg aaa acc tgg atg caa ttg cgc       1258
Met His Arg Phe Cys Ile Pro Cys Met Lys Thr Trp Met Gln Leu Arg
135                 140                 145                 150 aac acc tgc ccg ctg tgc aac gcc aag ctg gtg tac ctg ata gtg ggc       1306
Asn Thr Cys Pro Leu Cys Asn Ala Lys Leu Val Tyr Leu Ile Val Gly
                155                 160                 165 gtg acg ccc agc ggg tcg ttc agc acc atc ccg atc gtg aac gac ccc       1354
Val Thr Pro Ser Gly Ser Phe Ser Thr Ile Pro Ile Val Asn Asp Pro
            170                 175                 180 cag acc cgc atg gag gcc gag gag gcc gtc agg gcg ggc acg gcc gtg       1402
Gln Thr Arg Met Glu Ala Glu Glu Ala Val Arg Ala Gly Thr Ala Val
            185                 190                 195 gac ttt atc tgg acg ggc aat cag cgg ttc gcc ccg cgg tac ctg acc       1450
Asp Phe Ile Trp Thr Gly Asn Gln Arg Phe Ala Pro Arg Tyr Leu Thr
        200                 205                 210 ctg ggg ggg cac acg gtg agg gcc ctg tcg ccc acc cac cct gag ccc       1498
Leu Gly Gly His Thr Val Arg Ala Leu Ser Pro Thr His Pro Glu Pro
215                 220                 225                 230 acc acg gac gag gat gac gac gac ctg gac gac ggtgaggcgg ggggcggcg     1551
Thr Thr Asp Glu Asp Asp Asp Asp Leu Asp Asp
                235                 240 aggaccctgg gggaggagga ggaggggggg ggagggagga ataggcgggc gggcgggcga    1611
ggaaagggcg ggccggggag ggggcgtaac ctgatcgcgc ccccgttgt ctcttgca       1669 gca gac tac gta ccg ccc gcc ccc cgc cgg acg ccc cgc gcc ccc cca      1717
Ala Asp Tyr Val Pro Pro Ala Pro Arg Arg Thr Pro Arg Ala Pro Pro
            245                 250                 255 cgc aga ggc gcc gcc gcg ccc ccc gtg acg ggc ggg gcg tct cac gca      1765
Arg Arg Gly Ala Ala Ala Pro Pro Val Thr Gly Gly Ala Ser His Ala
        260                 265                 270 gcc ccc cag ccg gcc gcg gct cgg aca gcc ccc tcg gcg ccc atc          1813
Ala Pro Gln Pro Ala Ala Ala Arg Thr Ala Pro Pro Ser Ala Pro Ile
275                 280                 285 ggg cca cac ggc agc agt aac act aac acc acc acc aac agc agc ggc      1861
Gly Pro His Gly Ser Ser Asn Thr Asn Thr Thr Thr Asn Ser Ser Gly
290                 295                 300                 305 ggc ggc ggc tcc cgc cag tcg cga gcc gcg gtg ccg cgg ggg gcg tct      1909
Gly Gly Gly Ser Arg Gln Ser Arg Ala Ala Val Pro Arg Gly Ala Ser
            310                 315                 320
```

| | |
|---|---|
| ggc ccc tcc ggg ggg gtt ggg gtt gtt gaa gcg gag gcg ggg cgg ccg<br>Gly Pro Ser Gly Gly Val Gly Val Val Glu Ala Glu Ala Gly Arg Pro<br>325 330 335 | 1957 |
| agg ggc cgg acg ggc ccc ctt gtc aac aga ccc gcc ccc ctt gca aac<br>Arg Gly Arg Thr Gly Pro Leu Val Asn Arg Pro Ala Pro Leu Ala Asn<br>340 345 350 | 2005 |
| aac aga gac ccc ata gtg atc agc gac tcc ccg gcc tct ccc cac<br>Asn Arg Asp Pro Ile Val Ile Ser Asp Ser Pro Ala Ser Pro His<br>355 360 365 | 2053 |
| agg ccc ccc gcg gcg ccc atg cca ggc tcc gcc ccc cgc ccc ggt ccc<br>Arg Pro Pro Ala Ala Pro Met Pro Gly Ser Ala Pro Arg Pro Gly Pro<br>370 375 380 385 | 2101 |
| ccc gcg tcc gcg gcc gcg tcg ggc ccc gcg cgc ccc cgc gcg gcc gtg<br>Pro Ala Ser Ala Ala Ala Ser Gly Pro Ala Arg Pro Arg Ala Ala Val<br>390 395 400 | 2149 |
| gcc ccg tgt gtg cgg gcg ccg cct ccg ggg ccc ggc ccc cgc gcc ccg<br>Ala Pro Cys Val Arg Ala Pro Pro Pro Gly Pro Gly Pro Arg Ala Pro<br>405 410 415 | 2197 |
| gcc ccc ggg gcg gag ccg gcc gcc cgc ccc gcg gac gcg cgc cgt gtg<br>Ala Pro Gly Ala Glu Pro Ala Ala Arg Pro Ala Asp Ala Arg Arg Val<br>420 425 430 | 2245 |
| ccc cag tcg cac tcg tcc ctg gct cag gcc gcg aac caa gaa cag agt<br>Pro Gln Ser His Ser Ser Leu Ala Gln Ala Ala Asn Gln Glu Gln Ser<br>435 440 445 | 2293 |
| ctg tgc cgg gcg cgt gcg acg gtg gcg cgc ggc tcg ggg ggg ccg ggc<br>Leu Cys Arg Ala Arg Ala Thr Val Ala Arg Gly Ser Gly Gly Pro Gly<br>450 455 460 465 | 2341 |
| gtg gag ggt gga cac ggg ccc tcc cgc ggc gcc gcc ccc tcc ggc gcc<br>Val Glu Gly Gly His Gly Pro Ser Arg Gly Ala Ala Pro Ser Gly Ala<br>470 475 480 | 2389 |
| gcc ccc tcc ggc gcc ccc ccg ctc ccc tcc gcc tct gtc gag cag gag<br>Ala Pro Ser Gly Ala Pro Pro Leu Pro Ser Ala Ser Val Glu Gln Glu<br>485 490 495 | 2437 |
| gcg gcg gtg cgt ccg agg aag agg cgc ggg tcg ggc cag gaa aac ccc<br>Ala Ala Val Arg Pro Arg Lys Arg Arg Gly Ser Gly Gln Glu Asn Pro<br>500 505 510 | 2485 |
| tcc ccg cag tcc acg cgt ccc ccc ctc gcg ccg gca ggg gcc aag agg<br>Ser Pro Gln Ser Thr Arg Pro Pro Leu Ala Pro Ala Gly Ala Lys Arg<br>515 520 525 | 2533 |
| gcg gcg acg cac ccc ccc tcc gac tca ggg ccg ggg ggg cgc ggc cag<br>Ala Ala Thr His Pro Pro Ser Asp Ser Gly Pro Gly Gly Arg Gly Gln<br>530 535 540 545 | 2581 |
| gga ggg ccc ggg acc ccc ctg acg tcc tcg gcg gcc tcc gcc tct tcc<br>Gly Gly Pro Gly Thr Pro Leu Thr Ser Ser Ala Ala Ser Ala Ser Ser<br>550 555 560 | 2629 |
| tcc tcc gcc tct tcc tcc tcg gcc ccg act ccc gcg ggg gcc acc tct<br>Ser Ser Ala Ser Ser Ser Ala Pro Thr Pro Ala Gly Ala Thr Ser<br>565 570 575 | 2677 |
| tcc gcc acc ggg gcc gcg tcc tcc tct gct tcc gcc tcc tcg ggc ggg<br>Ser Ala Thr Gly Ala Ala Ser Ser Ser Ala Ser Ala Ser Ser Gly Gly<br>580 585 590 | 2725 |
| gcc gtc ggt gcc ctg gga ggg aga caa gag gaa acc tcc ctc ggc ccc<br>Ala Val Gly Ala Leu Gly Gly Arg Gln Glu Glu Thr Ser Leu Gly Pro<br>595 600 605 | 2773 |
| cgc gct gct tct ggg ccg cgg ggg ccg agg aag tgt gcc cgg aag acg<br>Arg Ala Ala Ser Gly Pro Arg Gly Pro Arg Lys Cys Ala Arg Lys Thr<br>610 615 620 625 | 2821 |
| cgc cac gcg gag act tcc ggg gcc gtc ccc gcg ggc ggc ctc acg cgc<br>Arg His Ala Glu Thr Ser Gly Ala Val Pro Ala Gly Gly Leu Thr Arg<br>630 635 640 | 2869 |

-continued

```
tac ctg ccc atc tcg ggg gtc tct agc gtg gtc gcc ctg tcg cct tac    2917
Tyr Leu Pro Ile Ser Gly Val Ser Ser Val Val Ala Leu Ser Pro Tyr
            645                 650                 655 gtg aac aag acg atc acg ggg gac tgc ctg ccc atc ctg gac atg gag    2965
Val Asn Lys Thr Ile Thr Gly Asp Cys Leu Pro Ile Leu Asp Met Glu
        660                 665                 670 acg ggg aac atc ggg gcg tac gtg gtc ctg gtg gac cag acg gga aac    3013
Thr Gly Asn Ile Gly Ala Tyr Val Val Leu Val Asp Gln Thr Gly Asn
    675                 680                 685 atg gcg acc cgg ctg cgg gcc gcg gtc ccc ggc tgg agc cgc cgc acc    3061
Met Ala Thr Arg Leu Arg Ala Ala Val Pro Gly Trp Ser Arg Arg Thr
690                 695                 700                 705 ctg ctc ccc gag acc gcg ggt aac cac gtg acg ccc ccc gag tac ccg    3109
Leu Leu Pro Glu Thr Ala Gly Asn His Val Thr Pro Pro Glu Tyr Pro
                710                 715                 720 acg gcc ccc gcg tcg gag tgg aac agc ctc tgg atg acc ccc gtg ggg    3157
Thr Ala Pro Ala Ser Glu Trp Asn Ser Leu Trp Met Thr Pro Val Gly
            725                 730                 735 aac atg ctg ttc gac cag ggc acc cta gtg ggc gcc ctg gac ttc cgc    3205
Asn Met Leu Phe Asp Gln Gly Thr Leu Val Gly Ala Leu Asp Phe Arg
        740                 745                 750 agc ctg cgg tct cgg cac ccg tgg tcc ggg gag cag ggg gcg tcg acc    3253
Ser Leu Arg Ser Arg His Pro Trp Ser Gly Glu Gln Gly Ala Ser Thr
    755                 760                 765 cgg gac gag gga aaa caa taagggacgc ccccgtgttt gtggga           3298
Arg Asp Glu Gly Lys Gln
770                 775

<210> SEQ ID NO 4
<211> LENGTH: 775
<212> TYPE: PRT
<213> ORGANISM: herpes simplex virus 1

<400> SEQUENCE: 4

Met Glu Pro Arg Pro Gly Ala Ser Thr Arg Arg Pro Glu Gly Arg Pro
 1               5                   10                  15

Gln Arg Glu Pro Ala Pro Asp Val Trp Val Phe Pro Cys Asp Arg Asp
            20                  25                  30

Leu Pro Asp Ser Ser Asp Ser Glu Ala Glu Thr Glu Val Gly Gly Arg
        35                  40                  45

Gly Asp Ala Asp His His Asp Asp Ser Ala Ser Glu Ala Asp Ser
    50                  55                  60

Thr Asp Thr Glu Leu Phe Glu Thr Gly Leu Leu Gly Pro Gln Gly Val
65                  70                  75                  80

Asp Gly Gly Ala Val Ser Gly Gly Ser Pro Arg Glu Glu Asp Pro
                85                  90                  95

Gly Ser Cys Gly Gly Ala Pro Pro Arg Glu Asp Gly Gly Ser Asp Glu
            100                 105                 110

Gly Asp Val Cys Ala Val Cys Thr Asp Glu Ile Ala Pro His Leu Arg
        115                 120                 125

Cys Asp Thr Phe Pro Cys Met His Arg Phe Cys Ile Pro Cys Met Lys
    130                 135                 140

Thr Trp Met Gln Leu Arg Asn Thr Cys Pro Leu Cys Asn Ala Lys Leu
145                 150                 155                 160

Val Tyr Leu Ile Val Gly Val Thr Pro Ser Gly Ser Phe Ser Thr Ile
                165                 170                 175
```

```
Pro Ile Val Asn Asp Pro Gln Thr Arg Met Glu Ala Glu Glu Ala Val
            180                 185                 190

Arg Ala Gly Thr Ala Val Asp Phe Ile Trp Thr Gly Asn Gln Arg Phe
        195                 200                 205

Ala Pro Arg Tyr Leu Thr Leu Gly Gly His Thr Val Arg Ala Leu Ser
    210                 215                 220

Pro Thr His Pro Glu Pro Thr Thr Asp Glu Asp Asp Asp Leu Asp
225                 230                 235                 240

Asp Ala Asp Tyr Val Pro Pro Ala Pro Arg Arg Thr Pro Arg Ala Pro
                245                 250                 255

Pro Arg Arg Gly Ala Ala Ala Pro Pro Val Thr Gly Gly Ala Ser His
            260                 265                 270

Ala Ala Pro Gln Pro Ala Ala Arg Thr Ala Pro Pro Ser Ala Pro
        275                 280                 285

Ile Gly Pro His Gly Ser Ser Asn Thr Asn Thr Thr Asn Ser Ser
    290                 295                 300

Gly Gly Gly Gly Ser Arg Gln Ser Arg Ala Ala Val Pro Arg Gly Ala
305                 310                 315                 320

Ser Gly Pro Ser Gly Gly Val Gly Val Val Glu Ala Glu Ala Gly Arg
                325                 330                 335

Pro Arg Gly Arg Thr Gly Pro Leu Val Asn Arg Pro Ala Pro Leu Ala
            340                 345                 350

Asn Asn Arg Asp Pro Ile Val Ile Ser Asp Ser Pro Pro Ala Ser Pro
        355                 360                 365

His Arg Pro Pro Ala Ala Pro Met Pro Gly Ser Ala Pro Arg Pro Gly
    370                 375                 380

Pro Pro Ala Ser Ala Ala Ala Ser Gly Pro Ala Arg Pro Arg Ala Ala
385                 390                 395                 400

Val Ala Pro Cys Val Arg Ala Pro Pro Gly Pro Gly Pro Arg Ala
                405                 410                 415

Pro Ala Pro Gly Ala Glu Pro Ala Ala Arg Pro Ala Asp Ala Arg Arg
            420                 425                 430

Val Pro Gln Ser His Ser Ser Leu Ala Gln Ala Ala Asn Gln Glu Gln
        435                 440                 445

Ser Leu Cys Arg Ala Arg Ala Thr Val Ala Arg Gly Ser Gly Gly Pro
    450                 455                 460

Gly Val Glu Gly Gly His Gly Pro Ser Arg Gly Ala Ala Pro Ser Gly
465                 470                 475                 480

Ala Ala Pro Ser Gly Ala Pro Pro Leu Pro Ser Ala Ser Val Glu Gln
                485                 490                 495

Glu Ala Ala Val Arg Pro Arg Lys Arg Arg Gly Ser Gly Gln Glu Asn
            500                 505                 510

Pro Ser Pro Gln Ser Thr Arg Pro Pro Leu Ala Pro Gly Ala Lys
        515                 520                 525

Arg Ala Ala Thr His Pro Pro Ser Asp Ser Gly Pro Gly Gly Arg Gly
    530                 535                 540

Gln Gly Gly Pro Gly Thr Pro Leu Thr Ser Ser Ala Ala Ser Ala Ser
545                 550                 555                 560

Ser Ser Ser Ala Ser Ser Ser Ala Pro Thr Pro Ala Gly Ala Thr
                565                 570                 575

Ser Ser Ala Thr Gly Ala Ala Ser Ser Ser Ala Ser Ala Ser Ser Gly
            580                 585                 590
```

-continued

```
Gly Ala Val Gly Ala Leu Gly Gly Arg Gln Glu Glu Thr Ser Leu Gly
            595                 600                 605

Pro Arg Ala Ala Ser Gly Pro Arg Gly Pro Arg Lys Cys Ala Arg Lys
    610                 615                 620

Thr Arg His Ala Glu Thr Ser Gly Ala Val Pro Ala Gly Gly Leu Thr
625                 630                 635                 640

Arg Tyr Leu Pro Ile Ser Gly Val Ser Val Val Ala Leu Ser Pro
                645                 650                 655

Tyr Val Asn Lys Thr Ile Thr Gly Asp Cys Leu Pro Ile Leu Asp Met
            660                 665                 670

Glu Thr Gly Asn Ile Gly Ala Tyr Val Leu Val Asp Gln Thr Gly
            675                 680                 685

Asn Met Ala Thr Arg Leu Arg Ala Ala Val Pro Gly Trp Ser Arg Arg
690                 695                 700

Thr Leu Leu Pro Glu Thr Ala Gly Asn His Val Thr Pro Pro Glu Tyr
705                 710                 715                 720

Pro Thr Ala Pro Ala Ser Glu Trp Asn Ser Leu Trp Met Thr Pro Val
                725                 730                 735

Gly Asn Met Leu Phe Asp Gln Gly Thr Leu Val Gly Ala Leu Asp Phe
            740                 745                 750

Arg Ser Leu Arg Ser Arg His Pro Trp Ser Gly Glu Gln Gly Ala Ser
    755                 760                 765

Thr Arg Asp Glu Gly Lys Gln
    770                 775

<210> SEQ ID NO 5
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgggggggc acacggtgag ggccctagcg ccggcccacc ctgagccggc cgcggacgag    60
gatgacgacg acctggac                                                 78

<210> SEQ ID NO 6
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaaacaaca gagacccat agtgatcgcc gatgcccccc cggccgctcc cacaggcccc     60
ccgcggcgcc c                                                        71

<210> SEQ ID NO 7
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcggtgcgtc cgaggaagag gcgcggggcc ggccaggaaa accccgcccc gcaggccgcg    60
``` cgtcccccccc tcgcgccggc agggg                                                                          85

<210> SEQ ID NO 8
<211> LENGTH: 825
<212> TYPE: PRT
<213> ORGANISM: herpes simplex virus 2

<400> SEQUENCE: 8

Met Glu Pro Arg Pro Gly Thr Ser Ser Arg Ala Asp Pro Gly Pro Glu
1               5                   10                  15

Arg Pro Pro Arg Gln Thr Pro Gly Thr Gln Pro Ala Ala Pro His Ala
            20                  25                  30

Trp Gly Met Leu Asn Asp Met Gln Trp Leu Ala Ser Ser Asp Ser Glu
        35                  40                  45

Glu Glu Thr Glu Val Gly Ile Ser Asp Asp Asp Leu His Arg Asp Ser
    50                  55                  60

Thr Ser Glu Ala Gly Ser Thr Asp Thr Glu Met Phe Glu Ala Gly Leu
65                  70                  75                  80

Met Asp Ala Ala Thr Pro Pro Ala Arg Pro Pro Ala Glu Arg Gln Gly
                85                  90                  95

Ser Pro Thr Pro Ala Asp Ala Gln Gly Ser Cys Gly Gly Gly Pro Val
            100                 105                 110

Gly Glu Glu Ala Glu Ala Gly Gly Gly Asp Val Cys Ala Val
        115                 120                 125

Cys Thr Asp Glu Ile Ala Pro Pro Leu Arg Cys Gln Ser Phe Pro Cys
130                 135                 140

Leu His Pro Phe Cys Ile Pro Cys Met Lys Thr Trp Ile Pro Leu Arg
145                 150                 155                 160

Asn Thr Cys Pro Leu Cys Asn Thr Pro Val Ala Tyr Leu Ile Val Gly
                165                 170                 175

Val Thr Ala Ser Gly Ser Phe Ser Thr Ile Pro Ile Val Asn Asp Pro
            180                 185                 190

Arg Thr Arg Val Glu Ala Glu Ala Val Arg Ala Gly Thr Ala Val
        195                 200                 205

Asp Phe Ile Trp Thr Gly Asn Pro Arg Thr Ala Pro Arg Ser Leu Ser
210                 215                 220

Leu Gly Gly His Thr Val Arg Ala Leu Ser Pro Thr Pro Pro Trp Pro
225                 230                 235                 240

Gly Thr Asp Asp Glu Asp Asp Leu Ala Asp Val Asp Tyr Val Pro
                245                 250                 255

Pro Ala Pro Arg Arg Ala Pro Arg Arg Gly Gly Gly Ala Gly Ala
            260                 265                 270

Thr Arg Gly Thr Ser Gln Pro Ala Ala Thr Arg Pro Ala Pro Pro Gly
        275                 280                 285

Ala Pro Arg Ser Ser Ser Gly Gly Ala Pro Leu Arg Ala Gly Val
            290                 295                 300

Gly Ser Gly Ser Gly Gly Pro Ala Val Ala Ala Val Pro Arg
305                 310                 315                 320

Val Ala Ser Leu Pro Pro Ala Ala Gly Gly Arg Ala Gln Ala Arg
                325                 330                 335

Arg Val Gly Glu Asp Ala Ala Ala Glu Gly Arg Thr Pro Pro Ala
            340                 345                 350

Arg Gln Pro Arg Ala Ala Gln Glu Pro Pro Ile Val Ile Ser Asp Ser
        355                 360                 365

```
Pro Pro Pro Ser Pro Arg Arg Pro Ala Gly Pro Gly Pro Leu Ser Phe
    370                 375                 380

Val Ser Ser Ser Ala Gln Val Ser Gly Pro Gly Gly Gly Gly
385                 390                 395                 400

Leu Pro Gln Ser Ser Gly Arg Ala Ala Arg Pro Arg Ala Ala Val Ala
                405                 410                 415

Pro Arg Val Arg Ser Pro Pro Arg Ala Ala Ala Pro Val Val Ser
            420                 425                 430

Ala Ser Ala Asp Ala Ala Gly Pro Ala Pro Ala Val Pro Val Asp
        435                 440                 445

Ala His Arg Ala Pro Arg Ser Arg Met Thr Gln Ala Gln Thr Asp Thr
    450                 455                 460

Gln Ala Gln Ser Leu Gly Arg Ala Gly Ala Thr Asp Ala Arg Gly Ser
465                 470                 475                 480

Gly Gly Pro Gly Ala Glu Gly Gly Pro Gly Val Pro Arg Gly Thr Asn
                485                 490                 495

Thr Pro Gly Ala Ala Pro His Ala Ala Glu Gly Ala Ala Ala Arg Pro
            500                 505                 510

Arg Lys Arg Arg Gly Ser Asp Ser Gly Pro Ala Ala Ser Ser Ser Ala
    515                 520                 525

Ser Ser Ser Ala Ala Pro Arg Ser Pro Leu Ala Pro Gln Gly Val Gly
530                 535                 540

Ala Lys Arg Ala Ala Pro Arg Arg Ala Pro Asp Ser Asp Ser Gly Asp
545                 550                 555                 560

Arg Gly His Gly Pro Leu Ala Pro Ala Ser Ala Gly Ala Ala Pro Pro
                565                 570                 575

Ser Ala Ser Pro Ser Ser Gln Ala Ala Val Ala Ala Ser Ser Ser
            580                 585                 590

Ser Ala Ser Ser Ser Ser Ala Ser Ser Ser Ala Ser Ser Ser Ser
            595                 600                 605

Ala Ser Ser Ser Ala Ser Ser Ser Ala Ser Ser Ser Ala
    610                 615                 620

Ser Ser Ser Ala Gly Gly Ala Gly Gly Ser Val Ala Ser Ala Ser Gly
625                 630                 635                 640

Ala Gly Glu Arg Arg Glu Thr Ser Leu Gly Pro Arg Ala Ala Ala Pro
                645                 650                 655

Arg Gly Pro Arg Lys Cys Ala Arg Lys Thr Arg His Ala Glu Gly Gly
            660                 665                 670

Pro Glu Pro Gly Ala Arg Asp Pro Ala Pro Gly Leu Thr Arg Tyr Leu
        675                 680                 685

Pro Ile Ala Gly Val Ser Ser Val Val Ala Leu Ala Pro Tyr Val Asn
    690                 695                 700

Lys Thr Val Thr Gly Asp Cys Leu Pro Val Leu Asp Met Glu Thr Gly
705                 710                 715                 720

His Ile Gly Ala Tyr Val Leu Val Asp Gln Thr Gly Asn Val Ala
                725                 730                 735

Asp Leu Leu Arg Ala Ala Pro Ala Trp Ser Arg Arg Thr Leu Leu
            740                 745                 750

Pro Glu His Ala Arg Asn Cys Val Arg Pro Pro Asp Tyr Pro Thr Pro
    755                 760                 765

Pro Ala Ser Glu Trp Asn Ser Leu Trp Met Thr Pro Val Gly Asn Met
770                 775                 780
```

-continued

```
Leu Phe Asp Gln Gly Thr Leu Val Gly Ala Leu Asp Phe His Gly Leu
785                 790                 795                 800

Arg Ser Arg His Pro Trp Ser Arg Glu Gln Gly Ala Pro Ala Pro Ala
                805                 810                 815

Gly Asp Ala Pro Ala Gly His Gly Glu
            820                 825
```